US009005628B2

(12) United States Patent
Dolly et al.

(10) Patent No.: US 9,005,628 B2
(45) Date of Patent: Apr. 14, 2015

(54) BIOTHERAPY FOR PAIN

(71) Applicants: James Oliver Dolly, Dublin (IE); Jiafu Wang, Dublin (IE); Jianghui Meng, Dublin (IE)

(72) Inventors: James Oliver Dolly, Dublin (IE); Jiafu Wang, Dublin (IE); Jianghui Meng, Dublin (IE)

(73) Assignee: Dublin City University, Dublin (IE)

( * ) Notice: Subject to any disclaimer, the term of this patent is extended or adjusted under 35 U.S.C. 154(b) by 0 days.

(21) Appl. No.: 13/644,386

(22) Filed: Oct. 4, 2012

(65) Prior Publication Data
US 2014/0099294 A1    Apr. 10, 2014

(30) Foreign Application Priority Data

Oct. 4, 2012  (EP) ..................................... 12187163

(51) Int. Cl.
*A61K 39/00* (2006.01)
*A61K 39/38* (2006.01)
*A61K 39/08* (2006.01)
*A61K 39/02* (2006.01)
*C12N 9/96* (2006.01)
*A61K 38/48* (2006.01)
*C12N 9/52* (2006.01)

(52) U.S. Cl.
CPC .............. *C12N 9/96* (2013.01); *A61K 38/4893* (2013.01); *C07K 2319/00* (2013.01); *C07K 2319/55* (2013.01); *C12N 9/52* (2013.01); *C07K 2319/01* (2013.01); *C07K 2319/33* (2013.01)

(58) Field of Classification Search
CPC ........... A61K 2300/00; A61K 38/4893; A61K 38/00; A61K 39/08; C07K 14/33; C07K 2319/00; C07K 2319/33; C12N 9/52; G01N 2333/33; G01N 33/56911
See application file for complete search history.

(56) References Cited

U.S. PATENT DOCUMENTS

| | | | |
|---|---|---|---|
| 6,395,513 B1 | 5/2002 | Foster et al. | |
| 8,455,203 B2 * | 6/2013 | Wang et al. | ..................... 435/7.1 |
| 2008/0032931 A1 * | 2/2008 | Steward et al. | .................. 514/12 |
| 2009/0018081 A1 * | 1/2009 | Steward et al. | .................. 514/12 |
| 2009/0069238 A1 * | 3/2009 | Steward et al. | .................. 514/12 |
| 2011/0091437 A1 * | 4/2011 | Foster et al. | .................. 424/94.3 |
| 2014/0099294 A1 * | 4/2014 | Dolly et al. | .................. 424/94.3 |

FOREIGN PATENT DOCUMENTS

| | | |
|---|---|---|
| WO | 2006099590 A2 | 9/2006 |
| WO | 2007138336 A2 | 12/2007 |

OTHER PUBLICATIONS

Wang Jiafu et al. "Longer-acting and highly potent chimeric inhibitors of excessive exocytosis created with domains from botulinum neurotoxin A and B" Biochem. Journal vol. 444, No. part 1, (2012), pp. 59-67.
Moulsdale H et al. "Retargeted endopeptidase-dependent inhibition of neurotransmitters from neurons involved in nociception" Abstracts of International Conference 2002 Basic and Therapeutic Aspects of Botulinum and Tetanus Toxins, Abstract 86.
Rummel Andreas et al, "Exchange of the HCC domain mediating double receptor recognition improves the pharmacodynamic properties of botulinum neurotoxin" FEBS Journal vol. 278, No. 23, Sp. Iss. SI, 2011, pp. 4506-4516.
Lawrence Gary W et al. "Excitatory Cholinergic and Purinergic Signaling in Bladder are Equally Susceptible to Botulinum Neurotoxin A Consistent with Co-Release of Transmitters from Efferent Fibers", Journal of Pharmacology and Experimental Therapeutics vol. 334, No. 3, 2010, pp. 1080-1086.
Extended European Search Report, mailed Feb. 7, 2013.

* cited by examiner

*Primary Examiner* — Nita M Minnifield
(74) *Attorney, Agent, or Firm* — Carlos A. Fisher

(57) ABSTRACT

The present invention is directed to analgesic Clostridial neurotoxin derivatives comprising polypeptides having a long-lasting SNARE protein-selective endopeptidase activity. These derivatives selectively bind to and are internalized by non-neuronal cells secreting cytokines or sensory neurons in preference to motor neurons or autonomic neurons. The invention is also directed to nucleic acid constructs encoding such polypeptides, and methods of making such derivatives and nucleic acid constructs, and methods of treating pain, such as chronic pain, by administering such derivatives to a patient suffering from, or at risk of suffering from such pain.

59 Claims, 8 Drawing Sheets

FIG. 1

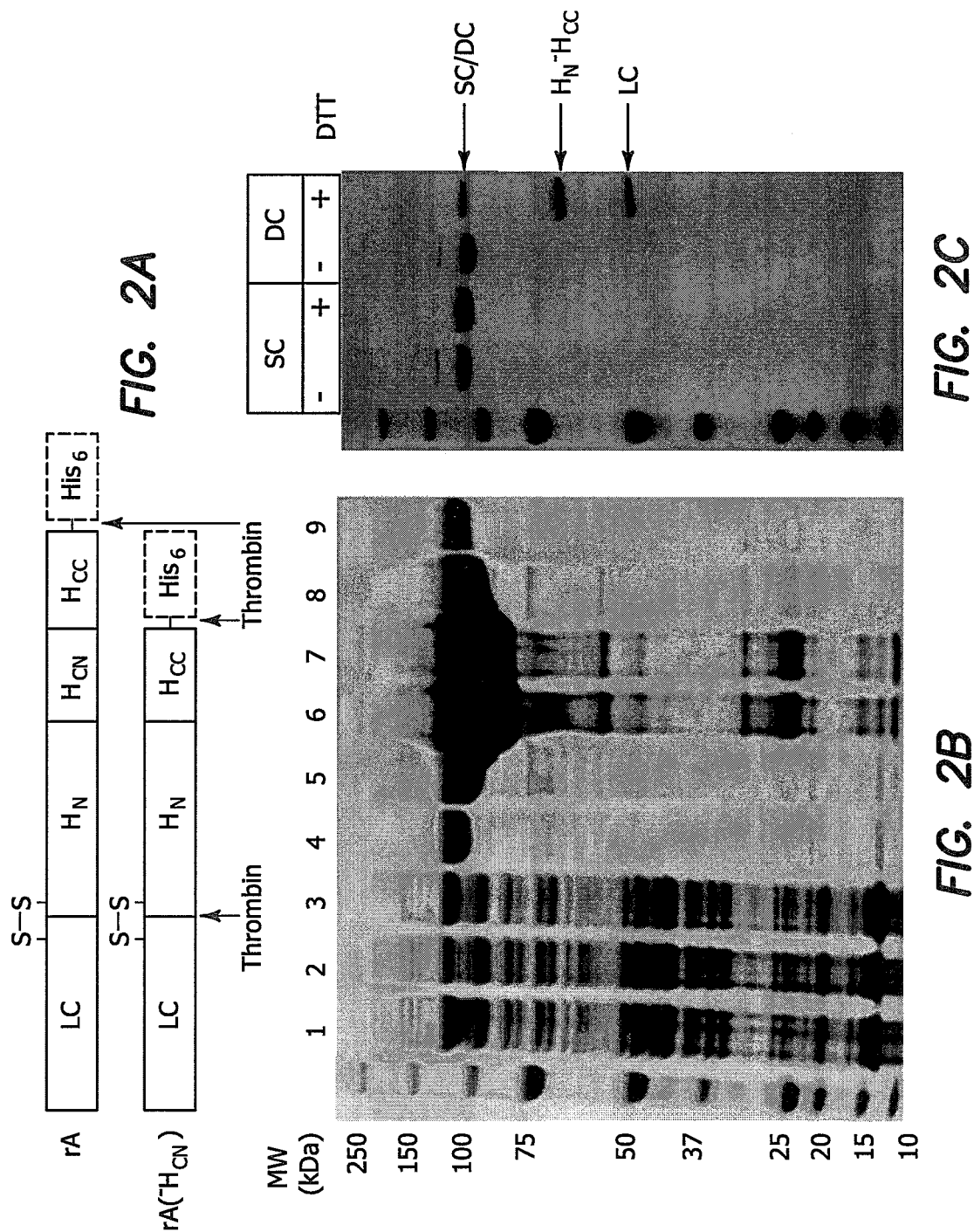

| Toxin | Specific neurotoxicity (mLD$_{50}$/mg) |
|---|---|
| rA | $2 \times 10^8$ |
| rA($^-$H$_{CN}$) | $\sim 3 \times 10^3$ |

FIG. 4

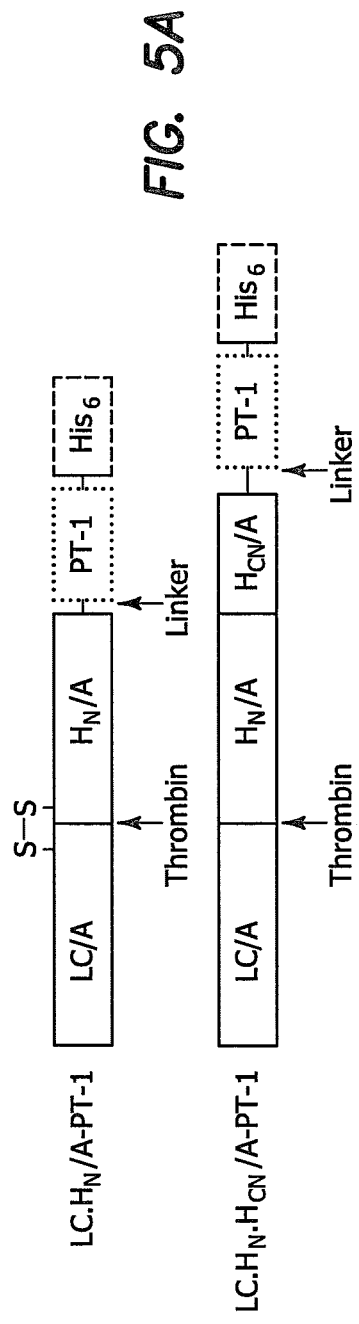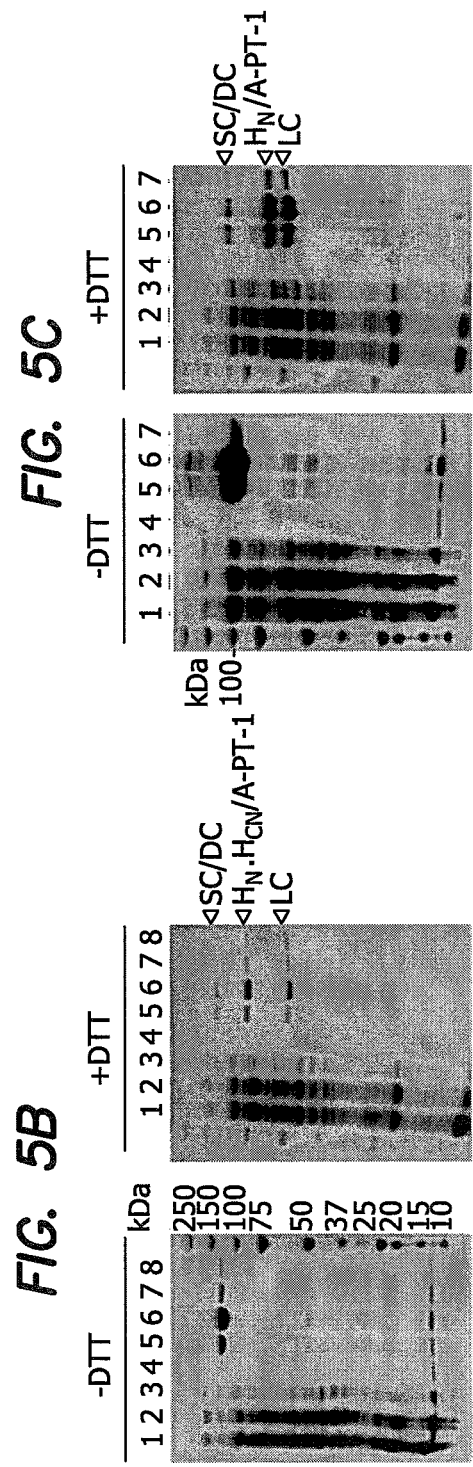

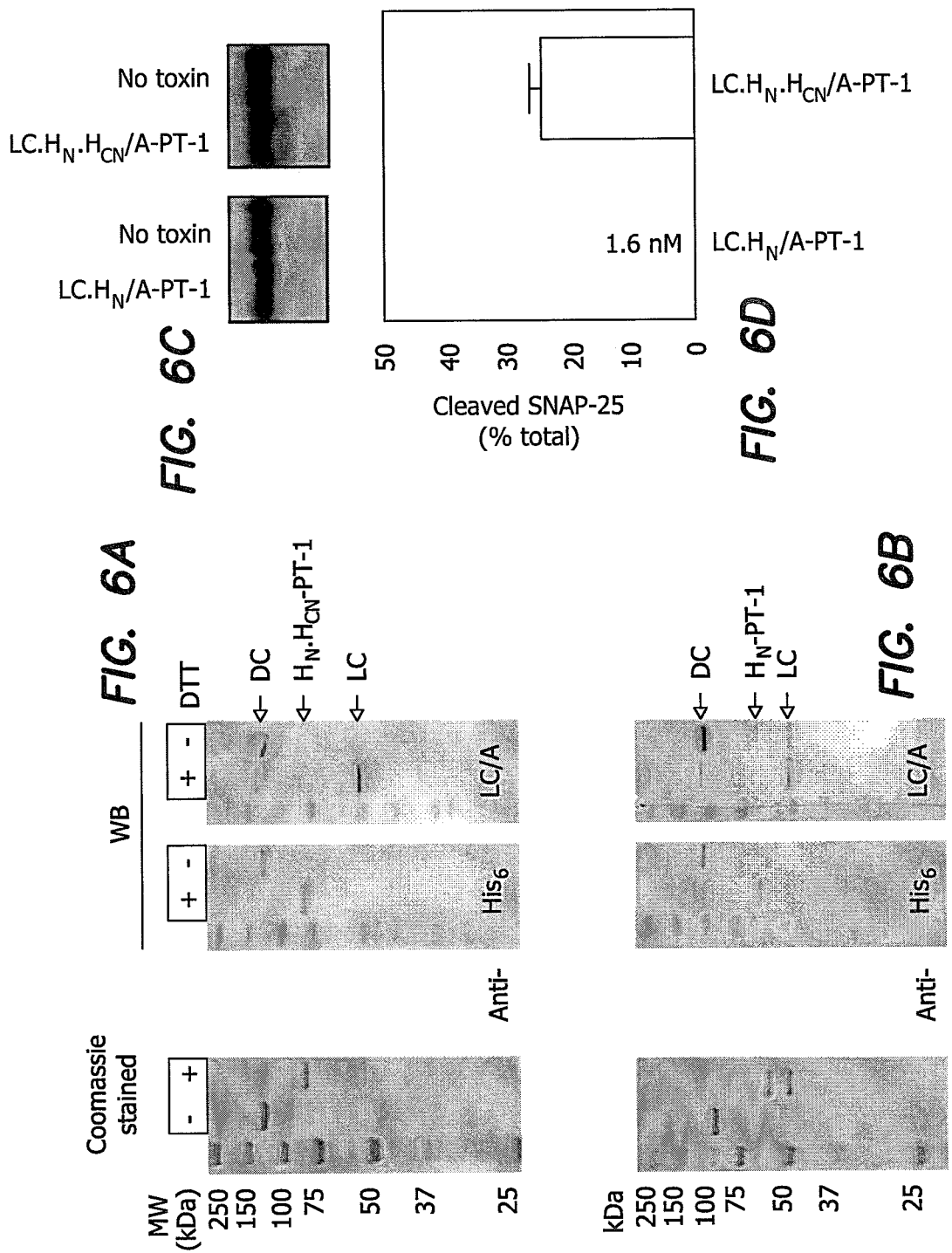

KD SNAP-23 (☐)
(% of control)

KD VAMP-3 (☐)
(% of control)

BIOTHERAPY FOR PAIN

SEQUENCE LISTING

The instant application contains a Sequence Listing which has been submitted in ASCII format via EFS-Web and is hereby incorporated by reference in its entirety. Said ASCII copy, created on Oct. 3, 2012, is named A-05027.txt and is 151,346 bytes in size.

The present invention is drawn to methods and composition involving Clostridial neurotoxin derivatives having an enhanced ability to disrupt exocytosis of pain and/or inflammatory mediators from nociceptors or inducers of inflammation, thus preventing pain.

The ability of Clostridial toxins such as, e.g., *Botulinum* neurotoxins (BoNTs) (including the serotypes BoNT/A, BoNT/B, BoNT/C1, BoNT/D, BoNT/E, BoNT/F and BoNT/G,) to inhibit neuronal transmission are being exploited in a wide variety of therapeutic and cosmetic applications, see e.g., Ward A B and Barnes M P, 2007, Clinical Users of *Botulinum* Toxins (Cambridge University Press, Cambridge). As an example, the BoNT/A-derived agent BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

There are Clostridial toxins other than the *C. botulinum* and *C. tetanus* derived toxins; these include, without limitation, the toxins of *C. perfringins, C. septicum, C. difficile, C. spiroforme, C. butyricum* and *C. barati*. However, it will be understood that in this specification a reference to "Clostridial toxins" or a similar reference, concerns the neurotoxins of *C. botulinum* subtypes and *C. tetani* subtypes, unless specifically or contextually indicated otherwise.

In addition, Clostridial toxin therapies are used or are proposed for treating:

a) neuromuscular disorders, see e.g., Kei Roger Aoki et al., Method for Treating Neuromuscular Disorders and Conditions with *Botulinum* Toxin Types A and B, U.S. Pat. No. 6,872,397 (Mar. 29, 2005); Rhett M. Schiffman, Methods for Treating Uterine Disorders, U.S. Patent Publication No. 2004/0175399 (Sep. 9, 2004); Richard L. Barron, Methods for Treating Ulcers and Gastroesophageal Reflux Disease, U.S. Patent Publication No. 2004/0086531 (May 7, 2004); and Kei Roger Aoki, et al., Method for Treating Dystonia with *Botulinum* Toxin C to G, U.S. Pat. No. 6,319,505 (Nov. 20, 2001);

b) eye disorders, see e.g., Eric R. First, Methods and Compositions for Treating Eye Disorders, U.S. Patent Publication No. 2004/0234532 (Nov. 25, 2004); Kei Roger Aoki et al., *Botulinum* Toxin Treatment for Blepharospasm, U.S. Patent Publication No. 2004/0151740 (Aug. 5, 2004); and Kei Roger Aoki et al., *Botulinum* Toxin Treatment for Strabismus, U.S. Patent Publication No. 2004/0126396 (Jul. 1, 2004);

c) pain, see e.g., Kei Roger Aoki et al., Pain Treatment by Peripheral Administration of a Neurotoxin, U.S. Pat. No. 6,869,610 (Mar. 22, 2005); Stephen Donovan, Clostridial Toxin Derivatives and Methods to Treat Pain, U.S. Pat. No. 6,641,820 (Nov. 4, 2003); Kei Roger Aoki, et al., Method for Treating Pain by Peripheral Administration of a Neurotoxin, U.S. Pat. No. 6,464,986 (Oct. 15, 2002); Kei Roger Aoki and Minglei Cui, Methods for Treating Pain, U.S. Pat. No. 6,113,915 (Sep. 5, 2000); Martin A. Voet, Methods for Treating Fibromyalgia, U.S. Pat. No. 6,623,742 (Sep. 23, 2003); Martin A. Voet, *Botulinum* Toxin Therapy for Fibromyalgia, U.S. Patent Publication No. 2004/0062776 (Apr. 1, 2004); and Kei Roger Aoki et al., *Botulinum* Toxin Therapy for Lower Back Pain, U.S. Patent Publication No. 2004/0037852 (Feb. 26, 2004);

d) muscle injuries, see e.g., Gregory F. Brooks, Methods for Treating Muscle Injuries, U.S. Pat. No. 6,423,319 (Jul. 23, 2002);

e) headache, see e.g., Martin Voet, Methods for Treating Sinus Headache, U.S. Pat. No. 6,838,434 (Jan. 4, 2005); Kei Roger Aoki et al., Methods for Treating Tension Headache, U.S. Pat. No. 6,776,992 (Aug. 17, 2004); and Kei Roger Aoki et al., Method for Treating Headache, U.S. Pat. No. 6,458,365 (Oct. 1, 2002); William J. Binder, Method for Reduction of Migraine Headache Pain, U.S. Pat. No. 5,714,469 (Feb. 3, 1998);

f) cardiovascular diseases, see e.g., Gregory F. Brooks and Stephen Donovan, Methods for Treating Cardiovascular Diseases with *Botulinum* Toxin, U.S. Pat. No. 6,767,544 (Jul. 27, 2004);

e) neurological disorders, see e.g., Stephen Donovan, Parkinson's Disease Treatment, U.S. Pat. No. 6,620,415 (Sep. 16, 2003); and Stephen Donovan, Method for Treating Parkinson's Disease with a *Botulinum* Toxin, U.S. Pat. No. 6,306,403 (Oct. 23, 2001);

g) neuropsychiatric disorders, see e.g., Stephen Donovan, *Botulinum* Toxin Therapy for Neuropsychiatric Disorders, U.S. Patent Publication No. 2004/0180061 (Sep. 16, 2004); and Steven Donovan, Therapeutic Treatments for Neuropsychiatric Disorders, U.S. Patent Publication No. 2003/0211121 (Nov. 13, 2003);

f) endocrine disorders, see e.g., Stephen Donovan, Method for Treating Endocrine Disorders, U.S. Pat. No. 6,827,931 (Dec. 7, 2004); Stephen Donovan, Method for Treating Thyroid Disorders with a *Botulinum* Toxin, U.S. Pat. No. 6,740,321 (May 25, 2004); Kei Roger Aoki et al., Method for Treating a Cholinergic Influenced Sweat Gland, U.S. Pat. No. 6,683,049 (Jan. 27, 2004); Stephen Donovan, Neurotoxin Therapy for Diabetes, U.S. Pat. No. 6,416,765 (Jul. 9, 2002); Stephen Donovan, Methods for Treating Diabetes, U.S. Pat. No. 6,337,075 (Jan. 8, 2002); Stephen Donovan, Method for Treating a Pancreatic Disorder with a Neurotoxin, U.S. Pat. No. 6,261,572 (Jul. 17, 2001); Stephen Donovan, Methods for Treating Pancreatic Disorders, U.S. Pat. No. 6,143,306 (Nov. 7, 2000);

g) cancers, see e.g., Stephen Donovan, Methods for Treating Bone Tumors, U.S. Pat. No. 6,565,870 (May 20, 2003); Stephen Donovan, Method for Treating Cancer with a Neurotoxin to Improve Patient Function, U.S. Pat. No. 6,368,605 (Apr. 9, 2002); Stephen Donovan, Method for Treating Cancer with a Neurotoxin, U.S. Pat. No. 6,139,845 (Oct. 31, 2000); and Mitchell F. Brin and Stephen Donovan, Methods for Treating Diverse Cancers, U.S. Patent Publication No. 2005/0031648 (Feb. 10, 2005);

h) otic disorders, see e.g., Stephen Donovan, Neurotoxin Therapy for Inner Ear Disorders, U.S. Pat. No. 6,358,926 (Mar. 19, 2002); and Stephen Donovan, Method for Treating Otic Disorders, U.S. Pat. No. 6,265,379 (Jul. 24, 2001);

i) autonomic disorders, see, e.g., Pankai J. Pasricha and Anthony N. Kalloo, Method for Treating Gastrointestinal Muscle Disorders and Other Smooth Muscle Dysfunction, U.S. Pat. No. 5,437,291 (Aug. 1, 1995);

j) as well as other disorders, see e.g., William J. Binder, Method for Treatment of Skin Lesions Associated with Cutaneous Cell-proliferative Disorders, U.S. Pat. No. 5,670,484 (Sep. 23, 1997); Eric R. First, Application of *Botulinum* Toxin to the Management of Neurogenic Inflammatory Disorders, U.S. Pat. No. 6,063,768 (May 16, 2000); Marvin Schwartz and Brian J. Freund, Method to Reduce Hair Loss and Stimulate Hair Growth, U.S. Pat. No. 6,299,893 (Oct. 9, 2001); Jean D. A. Carruthers and Alastair Carruthers, Cosmetic Use of *Botulinum* Toxin for Treatment of Downturned Mouth, U.S. Pat. No. 6,358,917 (Mar. 19, 2002); Stephen Donovan, Use of a Clostridial Toxin to Reduce Appetite, U.S. Patent Publication No. 2004/40253274 (Dec. 16, 2004); and Howard I. Katz and Andrew M. Blumenfeld, *Botulinum* Toxin Dental Therapies and Procedures, U.S. Patent Publication No. 2004/0115139 (Jun. 17, 2004); Kei Roger Aoki, et al., Treatment of Neuromuscular Disorders and Conditions with Different *Botulinum*, U.S. Patent Publication No. 2002/0010138 (Jan. 24, 2002); and Kei Roger Aoki, et al., Use of *Botulinum* Toxins for Treating Various Disorders and Conditions and Associated Pain, U.S. Patent Publication No. 2004/0013692 (Jan. 22, 2004).

Table 2, below, provides the amino acid sequences of isotypes of various currently known *botulinum*-related (BoNT and TeTX) Clostridial toxins. These toxins possess a minimum of approximately 35% amino acid identity with each other and share the same general functional domain organization and overall structural architecture. These Clostridial toxins are each naturally translated as a single chain polypeptide of approximately 150 kDa that is subsequently cleaved by proteolytic scission within a disulfide loop by a naturally-occurring protease, such as, e.g., an endogenous Clostridial toxin protease or a naturally-occurring protease produced in the environment. This posttranslational processing yields a mature di-chain molecule comprising an approximately 50 kDa light chain (LC) and an approximately 100 kDa heavy chain (HC) held together by a single inter-chain disulfide bond and noncovalent interactions.

Each mature di-chain Clostridial toxin molecule comprises three functionally distinct domains: 1) an enzymatic domain located in the LC that includes a metalloprotease region containing a zinc-dependent endopeptidase activity which specifically targets core components of the neurotransmitter release apparatus (the so-called SNARE ("Soluble NSF Attachment Protein Receptors") proteins that mediate the fusion of the synaptic vesicle with the cell membrane); 2) a translocation domain contained within the amino-terminal half of the H chain (termed "$H_N$") that facilitates release of at least the LC chain of the toxin from an endosome into the cytoplasm of the target cell; and 3) a binding domain found within the carboxyl-terminal half of the H chain ($H_C$) that determines the binding activity and binding specificity of the toxin. $H_C$ comprises $H_{CN}$ and $H_{CC}$ sub-domains (the N- and C-terminal portions of $H_C$, respectively). There is now substantial evidence that most or all BoNT/X toxins bind a target cell using a "dual receptor", wherein the $H_C$ portion of the toxin comprising both $H_{CN}$ and $H_{CC}$ subdomains binds certain cell surface gangliosides and a protein receptor (perhaps glycosylated); binding of the protein receptor facilitates the internalization of the toxin within the cell. By "X" is meant any serotype of *botulinum* toxin. Although the term "BoNT/X" is generally used to indicate subtypes of *botulinum* toxin, the term may also include TeTX regions thereof. $H_{CC}$ binds the receptor complex located at the surface of the target cell.

It will be understood that there exist strains of each of these toxins that may vary somewhat in their amino acid sequences in non-critical (so called variable) regions without a substantial change in the identity or activity characteristic of the indicated toxin or toxin domain.

In Table 1 below, the one-letter and three letter amino acid codes are provided:

TABLE 1

| Amino Acid | Three letter code | One letter code |
|---|---|---|
| alanine | Ala | A |
| arginine | Arg | R |
| asparagine | Asn | N |
| aspartic acid | Asp | D |
| asparagine or aspartic acid | Asx | B |
| cysteine | Cys | C |
| glutamic acid | Glu | E |
| glutamine | Gln | Q |
| glutamine or glutamic acid | Glx | Z |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Try | W |
| tyrosine | Tyr | Y |
| valine | Val | V |

TABLE 2

Clostridial Toxin Reference Sequences and Regions (identified from amino to carboxy direction; amino acid number to amino acid number)

| Toxin | SEQ ID NO: | LC | $H_N$ | $H_C$ |
|---|---|---|---|---|
| BoNT/A | 1 | M1-K448 | A449-K871 | N872-L1296 |
| BoNT/B | 2 | M1-K441 | A442-S858 | E859-E1291 |
| BoNT/C1 | 3 | M1-K449 | T450-N866 | N867-E1291 |
| BoNT/D | 4 | M1-R445 | D446-N862 | S863-E1276 |
| BoNT/E | 5 | M1-R422 | K423-K845 | R846-K1252 |
| BoNT/F | 6 | M1-K439 | A440-K864 | K865-E1274 |
| BoNT/G | 7 | M1-K446 | S447-S863 | N864-E1297 |
| TeNT | 8 | M1-A457 | S458-V879 | I880-D1315 |

Those of ordinary skill in the art recognize that naturally occurring Clostridial domain variants having variations in the amino acid shown above (or in the nucleotide sequences encoding these amino acid sequences) may occur in nature. As used herein, the term "naturally-occurring Clostridial domain variant" means any Clostridial domain (endopeptidase, translocation, and/or binding domains) produced by a naturally-occurring process, including, without limitation, Clostridial domain isoforms produced from alternatively-spliced transcripts, Clostridial domain isoforms produced by spontaneous mutations and Clostridial domain subtypes. As used herein, a naturally-occurring Clostridial domain variant functions in substantially the same manner as the reference Clostridial domain on which the naturally-occurring Clostridial domain variant is based, and can be substituted for the reference Clostridial domain in any aspect of the present invention. A naturally-occurring Clostridial domain variant may substitute one or more amino acids, two or more amino acids, three or more amino acids, four or more amino acids, five or more amino acids, ten or more amino acids, 20 or more amino, acids, 30 or more amino acids, 40 or more amino acids, 50 or more amino acids or 100 or more amino acids from the reference Clostridial domain on which the naturally-occurring Clostridial domain variant is based. A naturally-occurring Clostridial domain variant can also substitute at least 10 contiguous amino acids, at least 15 contiguous amino acids, at least 20 contiguous amino acids, or at least 25 contiguous amino acids from the reference Clostridial domain on which the naturally-occurring Clostridial domain variant is based, that possess at least 50% amino acid identity, 65% amino acid identity, 75% amino acid identity, 85% amino acid identity or 95% amino acid identity to the reference Clostridial domain on which the naturally-occurring Clostridial domain variant is based. It will also be understood that conservative amino acid insertions and deletions can also be made so long as the characteristic function and identity of the domain is not substantially altered.

Due to the degeneracy of the genetic code, one of ordinary skill in the art will recognize that these amino acid sequences may be encoded by a finite set of different DNA molecules having different, but defined, nucleotide sequences. For example, degenerate nucleotide sequences encoding a given peptide or protein may have different codons adapted or selected to favor expression in a particular host cell. Using this information one can construct an expressible open nucleic acid reading frame for assembly of a nucleic acid molecule comprising any combination of these amino acid domain-encoding regions, either alone or with additional nucleic acid sequences, inserted into a suitable expression vector and subsequent expression within a chosen host cell. For example, International Patent Publication WO01/14570 discloses methods of making single-chain, cleavable recombinant modified or unmodified Clostridial neurotoxin derivatives and chimeric and hybrid forms thereof using such methods. Additional publications disclosing methods of making expressible recombinant neurotoxins and derivatives thereof include U.S. Pat. Nos. 5,989,545; 6,203,794; 6,395,513; U.S. Publication Numbers U.S. 2003/0166238; U.S. 2002/169942; U.S. 2004/176299; U.S. 2004/126397; U.S. 2005/035730; U.S. 2005/068494; U.S. 2006/011966; International Patent Applications WO95/32738; WO 99/55359; WO96/33273; WO98/07864; WO99/17806; WO98/07864; WO02/44199; WO02/40506. These and all other patents, patent publications, and non-patent publications cited in this patent application, whether or not specifically indicated as such, are hereby individually incorporated by reference as part of this specification.

The use of recombinant DNA techniques permits the construction of modified Clostridial neurotoxins having different or modified functional properties from the naturally-occurring toxin subtypes and strains thereof. For example, altering the naturally-occurring amino acid sequence of the native neurotoxin light chain and/or adding a different therapeutic moiety permits the construction of transport proteins designed to carry a therapeutic agent within a neuron. See U.S. Pat. No. 6,203,794 (hereby incorporated by reference herein). Altering the targeting (cell-binding) domain permits the toxin to be transported within pancreatic cells, such as acinar cells, thereby preventing secretion of activated digestive enzymes by such cells, See U.S. Pat. No. 6,843,998 (hereby incorporated by reference herein), or sensory afferent neurons, thereby preventing neurotransmitter release and thus providing relief from pain; see U.S. Pat. No. 6,395,513 (hereby incorporated by reference herein.)

In addition, U.S. Pat. No. 7,422,877 (hereby incorporated by reference herein) discloses the creation of chimeric neurotoxin derivatives comprising, for example, the binding domain and the translocation domain (or modified versions thereof) of one neurotoxin subtype for example, BoNT/A, and the light chain region of another neurotoxin subtype, for example, BoNT/E. It will be seen that given the general structural homology between the neurotoxin subtypes, any combination of the three basic Clostridial neurotoxin domains, may be made in a single amino acid chain (or in cleaved di-chain molecules). Therefore, for example, a binding domain from any of neurotoxin subtypes A, B, C1, D, E, F, G, or TeTX may be independently combined with a translocation domain from neurotoxin subtypes A, B, C1, D, E, F, G, or TeTX, and further independently combined with a endopeptidase domain from any of neurotoxin subtypes A, B, C1, D, E, F, G or TeTX. This can be done, for example, by recombinant construction and expression of a single chimeric chain which is subsequently cleaved to yield the dichain toxin, or by separate expression of single H and L chains, which are then combined by, for example, creation of an interchain disulfide bond and subsequently purified. Furthermore, using such techniques, the activity of various domains may be altered (for example, mutations can be introduced in an LC domain to destroy the protease activity of the LC), or the naturally-occurring domains may be replaced with other moieties, as described elsewhere herein, where for example, the HC domain of BoNT/A (or a portion thereof) is mutated or deleted and a targeting ligand (TL) appended.

When discussing the three general neurotoxin domains of each Clostridial neurotoxin subtype (binding, translocation and endopeptidase), it will be understood that Clostridial neurotoxin research is a well-developed field, and the correlation of the amino acid sequences comprising each of these domains with their functions is well known. Additionally, the subdivision of these general domains into subdomains is also known. For example, the subdivision of binding domain $H_C$ into subdomains $H_{CN}$ (the amino-terminal portion of the domain, corresponding approximately to amino acids 871-1091 of BoNT/A) and $H_{CC}$ (the carboxy-terminal portion of the $H_C$ domain, corresponding approximately to amino acids 1092-1296 of BoNT/A) is also well known. See e.g., Lacy D B and Stevens R C, Sequence Homology and Structural Analysis of the Clostridial Neurotoxins, 1999, J. Mol. Biol. 291:1091-1104. Subdomain $H_{CN}$ is highly conserved among *botulinum* toxin subtypes, however, little is known about its function. The $H_{CC}$ subdomain is less conserved.

Additionally, the nucleotide and amino acid sequences of each of these domains and subdomains are known and have been disclosed in this specification, and therefore using this disclosure in combination with knowledge of the genetic code, nucleotide sequences encoding a protein to be expressed can be made. It would, of course, be a matter of routine for a person of ordinary skill in the art to immediately envision other nucleotide sequences encoding the indicated polypeptides. Also, due to the redundancy of the genetic code, a finite number of nucleotide sequences are possible for each polypeptide. Further, it is clear that nucleic acids can be synthesized that comprise conservatively modified variants of these nucleotide sequences (or unique portions of them) in the region of homology containing no more than 10%, 8% or 5% base pair differences from a reference sequence.

Further, it will be understood that the amino acid sequences set forth in Table 2 and elsewhere in this specification (SEQ ID NO: 1-8, 10, 12, 14, 16 and 18) provide a full disclosure of any and all nucleotide sequences encoding these amino acid sequences and indicated regions thereof. A nucleotide sequence encoding an endopeptidase domain, translocation domain, or binding domain (including any subdomain) of a given neurotoxin subtype may respectively have 60% or greater, or 65% or greater, or 70% or greater, or 75% or greater, or 80% or greater, or 85% or greater, or 90% or greater, or 95% or greater, or 100% identity to any of such reference amino acid sequence regions listed in Table 2 and/or SEQ ID NO: 1-8, 10, 12, 14, 16 and 18.

BRIEF DESCRIPTION OF THE DRAWINGS

FIG. 1 is a diagram showing various general embodiments of the present invention, beginning from a BoNT/X dichain toxin (which may be created by proteolyic cleavage of a recombinant single chain (SC) toxin), and showing pathways A or B, respectively. These involve the excision from BoNT/X of the $H_{CC}$ subdomain (pathway A), or mutation of the $H_{CC}$ subdomain (pathway B), and the addition of a targeting ligand (TL) selective to bind to sensory neurons and/or non-neuronal cells to block release of affectors in the chronic pain and/or inflammatory pathways to form novel genera of therapeutic biologics BoNT/X($^-H_{CC}$)-TL and BoNT/X (PrR$^-$)-TL. A member of either genus may be further modified as shown in pathway C by the addition of an active type E light chain protease domain (LC/E) to extend the time period of SNARE protein proteolysis; see LC/E-BoNT/X($^-H_{CC}$)-TL and LC/E-BoNT/X(PrR$^-$)-TL. For example, in the first instance, key residues ($Lys^{1192}$ and/or $Ala^{1196}$ in $H_{CC}$ of BoNT/B) identified as being essential for binding to its protein receptor (synaptotagmin) could be mutated to $Glu^{1192}$ and $Lys^{1196}$ to ablate their interaction, as data have shown a greater than 300-fold drop of its neuromuscular paralytic activity upon mutation of either of the key residues (Rummel et al., Proc. Nat. Acad. Sci. USA, 2007, 104:359-364 and Jin et al., Nature, 2006, 444:1092-1095).

FIG. 2A shows schematic diagrammatical structures of recombinant BoNT/A (rA) and a variant (rA($^-H_{CN}$)) lacking the $H_{CN}$ subdomain. Both structures illustrate a C-terminal 6 residue histidine tag ($H_6$) (SEQ ID NO: 19), appended during the construction of the recombinant nucleic acid to aid in purification of the protein by immobilized metal affinity chromatography (IMAC), as well as two thrombin cleavage sites, also inserted during the construction of the recombinant nucleic acid. The first (leftmost) thrombin cleavage site permits post-expression proteolytic conversion of single chain to the active di-chain form; the second thrombin site permits the removal of the $H_6$ "tag" (SEQ ID NO: 19) after purification of the polypeptide.

FIG. 2B shows the purification from a cell lysate of rA$^-H_{CN}$ by IMAC on a Coomassie blue-stained SDS-PAGE gel.

FIG. 2C shows a Coomassie blue-stained SDS-PAGE gel of IMAC-purified SC and DC proteins under reducing and non-reducing conditions.

FIG. 3A shows Western blots of SDS-PAGE gels. The lanes of the two blots on the right are samples of eluates in binding assays between an immobilized recombinantly expressed fragment of the BoNT/A protein receptor (SV2C) and recombinant proteins BoNT/A (rA), rA$^-H_{CN}$, and rE (recombinant BoNT/E). Two blots on the left are samples of rA, rA$^-H_{CN}$ and rE (40 ng/lane) to confirm the specificity of antibodies used. Blots were developed using antibodies against the light chain of either BoNT/A (anti-LC/A) or BoNT/E (anti-LC/E).

FIG. 3B shows Western blots of SDS-PAGE gels in which rat cerebellar granule neurons (CGNs) pre-treated with varying concentrations (expressed in the upper axis legend in units of picomolarity (pM)) of either toxin derivative rA or rA$^-H_{CN}$. The gels show protein bands comprising the SNARE proteins syntaxin 1, SNAP-25, or SNAP-$25_A$ (a cleavage product of BoNT/A digestion). The results show that, as expected, the non-target SNARE syntaxin 1 is not cleaved by either toxin protein; SNAP-25 is only digested by rA (and not by rA$^-H_{CN}$, except at very high concentrations (1 nM) of the toxin). The results suggest the inability of rA$^-H_{CN}$ to effectively internalize into the CGN cells.

FIG. 3C is a table showing the toxicity of rA and rA$^-H_{CN}$ upon intraperitoneal injection of each toxin into mice, expressed as $mLD_{50}$—the lowest dose of toxin sufficient to kill 50% of injected mice within 4 days. The table indicates that rA has an $mLD_{50}$ $6.7 \times 10^4$ times greater than does rA$^-H_{CN}$ in this experiment.

FIG. 4 shows a diagrammatic view of various exemplary targeting ligands (TLs) that may be combined with individual members of the toxin-derived therapeutic genera shown in FIG. 1 to make therapeutic embodiments of the invention targeted to pain-sensing nerves or to non-neuronal cells that secrete inflammatory mediators and contribute to pain.

FIG. 5A shows schematic diagrammatical structures of recombinant proteins LC.$H_N$/A-PT-1 and LC.$H_N$.$H_{CN}$/A-PT-1; both proteins contain a C-terminal portion comprising a $His_6$ tag (SEQ ID NO: 19) for use in affinity purification, and a purotoxin-1 (PT-1) fragment for use as a targeting ligand (TL) of the toxin to the P2X purinoceptor 3 receptor of purinergic neurons. The LC.$H_N$/A-PT-1 protein comprises recombinant BoNT/A lacking the entire $H_C$ region; the LC.$H_N$.$H_{CN}$/A-PT-1 protein comprises the LC.$H_N$/A-PT-1 plus the BoNT/A $H_{CN}$ region (but not the $H_{CC}$ region) linked to the C terminus thereof, and thence to the TL-$His_6$ portion ("$His_6$" disclosed as SEQ ID NO: 19). A single thrombin cleavage site separates LC/A from the remainder of the chain, although it remains linked by the disulfide bond.

FIG. 5B shows reducing and non-reducing Coomassie blue-stained SDS-PAGE gels of lysate (1), flow-through (2), wash (3) and eluate (4-8) fractions of IMAC chromatography of *E. coli* cells expressing LC.$H_N$.$H_{CN}$/A-PT-1.

FIG. 5C shows reducing and non-reducing Coomassie blue-stained SDS-PAGE gels of lysate (1), flow-through (2), wash (3) and eluate (4-7) fractions of IMAC of *E. coli* cells expressing LC.$H_N$/A-PT-1.

FIG. 6A shows the results of a Coomassie blue-stained SDS-PAGE gel (left) of purified LC.$H_N$.$H_{CN}$/A-PT-1 under reducing and non-reducing conditions, and Western blots of the same sample under reducing and non-reducing conditions developed using anti-$His_6$ antibody (middle) ("$His_6$" disclosed as SEQ ID NO: 19), or anti-LC/A antibody (right). The gels show that under non-reducing conditions the protein exists as a disulfide-linked dichain; when reduced, the dissociated LC/A can be visualized with anti-LC/A antibody, and the remainder of the recombinant toxin can be seen with the anti-$His_6$ antibody ("$His_6$" disclosed as SEQ ID NO: 19).

FIG. 6B shows the results of a Coomassie blue-stained SDS-PAGE gel (left) of purified LC.$H_N$/A-PT-1 under reducing and non-reducing conditions, and Western blots of the same sample developed using anti-$His_6$ antibody (middle) ("$His_6$" disclosed as SEQ ID NO: 19), or anti-LC/A antibody (right). The gels show that under non-reducing conditions the protein exists as a disulfide-linked dichain; when reduced, the dissociated LC/A can be visualized with anti-LC/A antibody, and the remainder of the recombinant toxin can be seen with the anti-$His_6$ antibody ("$His_6$" disclosed as SEQ ID NO: 19).

FIG. 6C shows Western blots of SDS-PAGE gels in which rat trigeminal ganglionic neurons (TGNs) were pre-treated with 1.6 nM of either toxin derivative LC.$H_N$/A-PT-1 (left) or LC.$H_N$.$H_{CN}$/A-PT-1, then lysed and electrophoresed. The gels show protein bands comprising the SNARE proteins SNAP-25 (upper band), or the LC/A cleavage product SNAP-$25_A$ (lower band on right Western blot). The results show that SNAP-25 is only digested by LC.$H_N$.$H_{CN}$/A-PT-1, (and not by LC.$H_N$/A-PT-1). The results are consistent with the ability of LC.$H_N$.$H_{CN}$/A-PT-1 to effectively bind to enter the TGN cells.

FIG. 6D is a graph showing the results of the assay shown visually in FIG. 6C. The percentage of SNAP-25 cleaved by 1.6 nM of LC.$H_N$.$H_{CN}$/A-PT-1 is about 25%, and the percentage of SNAP-25 cleaved by LC.$H_N$/A-PT-1 is approximately 0%.

DESCRIPTION OF THE FIELD

Figure 7A:
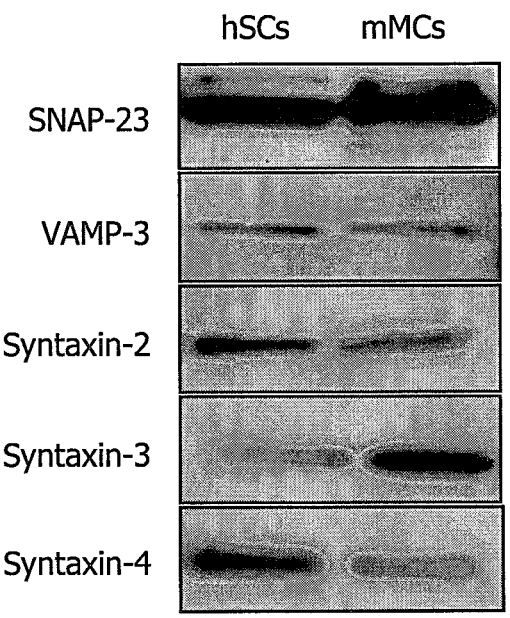
FIG. 7A shows Western blots of SDS-PAGE gels from lysates of: human synovial cell line (hSC) (which contains SNAP-23, VAMP3, syntaxin 2, 3 and 4 as found in mouse macrophase cells line RAW264.9 (mMC).

Chronic pain is a major challenge for patients and health providers alike. Patients suffering from chronic pain represent approximately 20% of the adult population.

There are two general types of chronic pain: inflammatory nociceptive pain and neuropathic pain. Inflammatory nociceptive pain usually arises from an insult to tissue and the resultant activation of inflammatory cascades and chemoreceptors. On the other hand, neuropathic pain (for example, without limitation, chronic pain, such as cancer pain, post-operative pain, neuropathic pain, allodynia, post-herpetic neuralgia, irritable bowel syndrome, and other visceral pain, bone pain, peripheral neuropathy, circulatory system-affiliated pain, and some types of headache pain) results from neuronal damage in the peripheral or central nervous systems and involves sensitization (such as allodynia), i.e. increased stimulation of peripheral nociceptors that amplifies pain signals relayed to the brain.

There remains an unmet need for effective treatment of chronic pain because non-steroidal anti-inflammatory drugs, traditionally used for inflammatory nociceptive pain, are short-acting and can have serious side effects. Similarly, while pain involving an inflammatory nociceptive mechanism usually is limited in duration to the period of tissue repair and generally is relieved by available analgesic agents or opioids (Myers, REGIONAL ANESTHESIA 20:173-184 (1995)), the side and deleterious effects of long-term treatment with opioids is well known.

Likewise, despite the fact that approximately 3% of the population suffers from neuropathic pain at any given time, there is no satisfactory existing treatment; available therapies work poorly, are not effective for a significant segment of patients, or cause unacceptable adverse effects.

Encouragingly, at least some sufferers of chronic pain respond to the long-acting *botulinum* neurotoxin (BoNT) type A (one of 7 toxin serotypes (/A-G) produced by *Clostridium botulinum*) due to specific and persistent inhibition of the release of transmitters from peripheral nerves. This blockade results from the proteolytic cleavage of the SNARE proteins; proteins essential for $Ca^{2+}$-stimulated exocytosis of neurotransmitters and other agents via membrane-vesicle fusion.

The unique profile of activities provided by Clostridial neurotoxins (detailed below) has been exploited successfully for treating numerous human disorders (~100 conditions) arising from over-activity of nerves innervating skeletal/smooth muscles or glands; reviewed in Ward, A. B. & Barnes, M. P., CLINICAL USES OF BOTULINUM TOXINS, Cambridge University Press (2007).

In vivo, Clostridial bacteria produce a toxin complex (the "hemagglutinin complex") that comprises the approximately 150-kDa di-chain Clostridial toxin along with other proteins. These other, non-toxin proteins are collectively called non-toxic associated proteins (NAPs). Identified NAPs include proteins possessing hemaglutination activity, such, e.g., a hemagglutinin of approximately 17-kDa (HA-17), a hemagglutinin of approximately 33-kDa (HA-33) and a hemagglutinin of approximately 70-kDa (HA-70); as well as a non-toxic non-hemagglutinin (NTNH), a protein of approximately 130-kDa, see, e.g., Eric A. Johnson and Marite Bradshaw, *Clostridial botulinum* and its Neurotoxins: A Metabolic and Cellular Perspective, 39 TOXICON 1703-1722 (2001); Stephanie Raffestin et al., *Organization and Regulation of the Neurotoxin Genes in Clostridium botulinum and Clostridium tetani,* 10 Anaerobe 93-100 (2004) and Gu et al., *Botulinum* Neurotoxin is Shielded by NTNHA in an Interlocked Complex, 335 Science 977-81 (2012).

In nature, the toxin complex is believed to be important for the intoxication process at least in part because it appears to provide protection to the toxin molecule from adverse environmental conditions and resistance to protease digestion. Importantly, certain domains of the HA and NTNH proteins appear to coordinate with toxin binding and bind to locations on the cell surface (and may bind to the natural Clostridial neurotoxin cell surface receptor at sites other than or additional to the toxin binding site), thus facilitating binding, internalization, and activation of the toxin.

BoNT/A (and, to a lesser degree, BoNT/B) hemagglutinin complexes are presently in clinical use for a variety of medical conditions. All 7 BoNT serotypes contain a light chain protease domain (LC), which is linked to a heavy chain cell-binding and transport domain (HC) through a single disulfide bond and non-covalent bonds. A C-terminal moiety of HC ($H_C$) binds to the specific acceptors expressed on various nerve types (including motor, autonomic and sensory neurons), whereas the N-terminal half of HC ($H_N$) forms a channel that allows the attached LC to translocate from 'endosomal-like' membrane vesicles through the $H_N$ pore into the cytosol (Dolly et al., CURR. OPIN. PHARMACOL. 9:326-35, 2009). Thereafter, with a selectivity depending on the toxin serotype, the LC cleaves a specific SNARE substrate and negates its role in neurotransmitter release. For example, the LC of BONT/A (LC/A) removes 9 amino acids from the C-terminal of the SNARE protein SNAP-25, whereas the LC/E deletes a further 17 C-terminal residues from the same SNARE and, thus, gives a more disruptive blockade of neuro-exocytosis; Meng et al., J. NEUROSCI. 29:4981-4192 (2009) (hereinafter "Meng et al. 2009"). Other Clostridial toxins cleave other SNARE proteins: for example, and without limitation, BoNT/C cleaves the SNARE proteins SNAP-25 and syntaxin 1, and TeTx, BoNT/B, BoNT/D, BoNT/F, and BoNT/G cleave the SNARE protein synaptobrevin (also known as VAMP). An example of this selective disruption, the inhibition of transmitter release by LC/A can usually be reversed, at least transiently, by elevating $Ca^{2+}$ influx, but not to such an extent in the case of LC/E (Dolly et al., FEBS J. 278:4454-66, 2011). However, the short transient paralysis induced by LC/E limits its usefulness in clinical applications.

BoNT/A hemagglutinin complex ("BoNT/A complex") has been found to be effective in some, but not all, migraine sufferers; see e.g., Naumann et al., NEUROLOGY 70:1707-1714 (2008), Jackson et al., JAMA 307:1736-1745 (2012), and Dodick et al., Headache 50:921-936 (2010). Moreover, BoNT/A is unable to block the release of pain-mediating peptides (such as calcitonin gene-related peptide (CGRP) and substance P) from sensory neurons when elicited by activating TRPV1 (transient receptor potential vanilloid type 1), non-selective cation channels which are sensitive to capsaicin (Meng et al., 2009; Meng et al., J. Cell Sci. 120:2864-2874 (2007) (hereinafter Meng et al., 2007).

A chimeric Clostrial neurotoxin derivative comprising BoNT/E LC protease (LC/E) and translocation domain ($H_N$/E) synthetically retargeted via the $H_C$ of type A (Wang et al., J. BIOL. CHEM. 283:16993-17002 (2008) (hereinafter Wang et al., 2008")), potently blocks CGRP release from nociceptive neurons and attenuates their firing elicited by CGRP or TRPV1-activation (Meng et al 2009). Furthermore, a synthetic variant of LC/E protease engineered to be long-acting by appending the more robust LC/E protease to a mutated inactive form of the long-lived protease in BoNT/A has proved to be a very effective therapeutic both in cultured sensory neurons and in an animal model of inflammatory pain (Wang et al., J. BIOL. CHEM. 286:6375-85, 2011) (hereinafter "Wang et al., 2011").

Additionally, another long-acting toxin serotype, BoNT/C1, blocks CGRP release from sensory trigeminal ganglionic neurons (TGNs) establishing its anti-nociceptive potential (Meng et al 2007). Although BoNT/D (having a long-lasting protease activity) is also effective in blocking CGRP release, it cannot be used as therapy for human patients in its wild-type form because BoNT/D does not bind human muscle or block neurotransmission; Coffield et al., J. PHARMACOL. EXP. THER. 280:1489-1498 (1997) (hereinafter "Coffield et al., 1997"). This notable finding highlights some difference between the response to BoNT/D in human and rodent because one group has recently claimed that the natural BoNT/A receptor synaptic vesicle protein 2 (SV2), can act as a protein receptor for BoNT/D in rat and mouse (Peng et al., PLoS PATHOGENS 7:e1002008, (2011)).

However, all these BoNT variants suffer from the disadvantage of non-selectivity; they block the release of transmitters and mediators from motor and autonomic nerves, as well as sensory neurons. This lack of specificity could lead to serious side effects in clinical use for treatment of pain.

DESCRIPTION AND EXAMPLES

The present invention is directed to methods and compositions having several aspects and embodiments which are encompassed by the claims. Thus, and without limitation, in one embodiment the present invention is directed to novel biotherapeutics for the treatment of chronic and/or inflammatory pain; such agents may be designed by ablating the normal tropism of Clostridial neurotoxins and their derivatives. Specifically, the biologics may be retargeted by deleting or modifying $H_{CC}$ which possesses binding sites for the protein and ganglioside receptors, and appending one of several possible targeting ligands (hereinafter referred to as "TL"s) to the *C terminus* of the HC. The TLs are preferably chosen to restrict the action of Clostridial toxin derivatives selectively to pain-sensing neurons, thereby leaving other neuron types unaffected. Retention of the $H_{CN}$ second subdomain is a novel advance due to our discovery of its importance for internalization of the LC of the toxin into neurons (or non-neural cells), with subsequent cleavage of SNAP-25 and inhibition of exocytosis; see, e.g., FIG. 2, FIG. 3 and Example 1.

Figure 1:
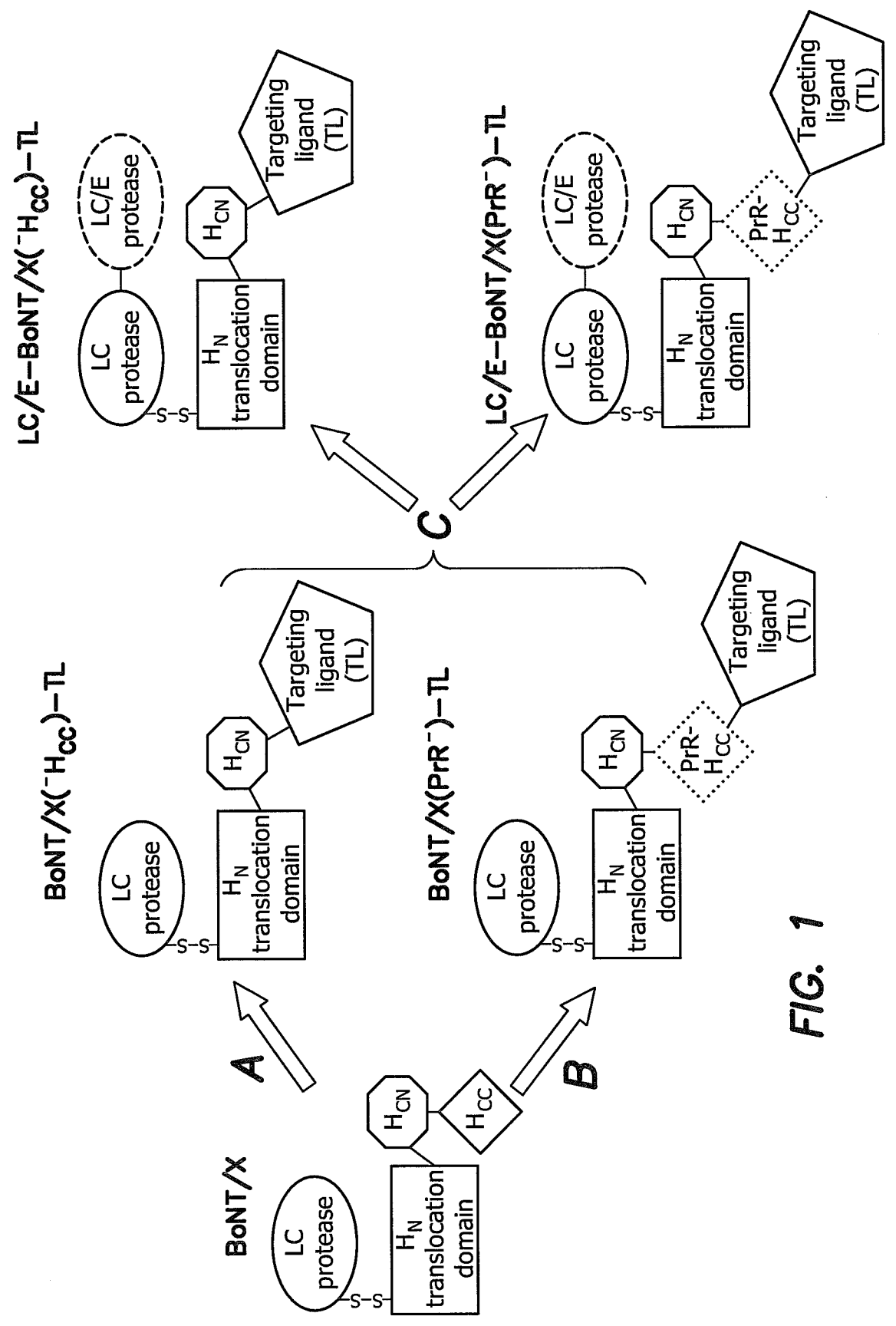

As shown in FIG. 1 and described herein, in certain embodiments of the invention both of the $H_C$ subdomains ($H_{CN}$ and $H_{CC}$) are retained (including the ganglioside binding region(s) of $H_{CC}$), but the ability to bind the protein receptor, e.g. synaptotagmin, is ablated by mutating residues identified as being essential for the latter interaction. For example, mutating either $Lys^{1192}$ to Glu or $Ala^{1196}$ to Lys in BoNT/B $H_{CC}$ decreased its potency by >300-fold on neuromuscular junction (Rummel et al., PROC. NAT. ACAD. SCI. USA 104:359-64, 2007; Jin et al., NATURE 444:1092-95, 2006). Thus this strategy has the advantage of exploiting the neurotoxin's ability to bind a "dual receptor" for TL to more effectively bind its target; binding to the gangliosides through the mutated $H_{CC}$ portion appears to increase the local concentration of the therapeutic at the cell surface near putative protein receptors and, thus, enhance interaction of each TL with its own requisite protein ectoreceptor on the target cell surface. Thus, the efficacy of the therapeutic is increased by this dual binding modality.

In a third non-limiting set of embodiments also shown in FIG. 1, additional novel therapeutics may be made by creating proteins recombinantly in which the light chain protease of BoNT/E, a robust inhibitor of neuro-exocytosis, is attached to BoNT/A or one or more of the constructs described above. This exerts a stabilizing influence to yield a long-lasting protease activity on target SNARE proteins. The ability to make and use such a selective and long-acting family of biotherapeutics represents a milestone advance that should revolutionize the development of future generations of effective and selective drugs for chronic and inflammatory pain.

As used herein the term "specific", when used with regard to ligand:target interactions, means that the ligand preferentially binds and/or catalyzes the target with an avidity of at least $10^2:1$, $10^3:1$, $10^4:1$, or at least about $10^5:1$ or at least about $10^6:1$ over non-target substances under substantially physiological conditions. The term "selective", when used with regard to ligand:target interactions, means that the ligand preferentially binds and/or catalyzes the target with an avidity of 10:1, or at least about $10^2$:1, or at least about $10^3$:1 or up to $10^4$:1 over non-target substances under substantially physiological conditions.

Thus, in one aspect, the present invention concerns the design, preparation, and use of one or more gene constructs encoding polypeptides comprising analgesic core therapeutics that inhibit neurotransmission (SNARE-selective proteases) and possess an analgesic activity. These may include, consist of, or consist essentially of, without limitation, derivatives of TeTx or BoNT/X (serotypes A, B, C1, D, E, F or G), but either contain a mutated $H_{CC}$ (substantially lacking the ability to bind the protein receptor but capable of interacting with gangliosides, see above) or are substantially devoid of the $H_{CC}$ region (see FIG. 1).

In another, supplementary approach, the LC/E coding region, which encodes a protease that acts as an effective inhibitor of CGRP release from sensory neurons (see, e.g., Want et al., 2011; Meng et al., 2009) may be joined to one or more of the above-mentioned oligonucleotide candidates, preferably prior to the next step.

In some embodiments, the oligonucleotide may comprise an LC/X that is mutated so as to substantially lack neuronal SNARE-selective protease activity compared to the expressed unmutated protein. For example, mutating residue Lys224 in LC/E moiety to Asp significantly increased its cleavage to human SNAP-23 with reduced activity towards neuronal SNAP-25 (Chen and Barbierio, Proc. Nat. Acad. Sci. USA, 106:9180-9184, 2009). In such a case, it will be understood that such an oligonucleotide can be referred to using the nomenclature mLC.BoNT/X (where "X" is any toxin serotype) generally refers to a BoNT/X in which the light chain protease has been mutated to have substantially no proteolytic activity towards neuronal SNARE proteins, while substantially maintaining the steric structure of the original BoNT/X toxin.

In either event, attachment of a gene encoding the requisite TL to these molecules will endow the translated polypeptide with the ability to selectively target sensory neurons or cytokine-releasing cells (shown diagrammatically in FIG. 1). Clearly, one of the advantages of the present invention is that it provides an array of different gene constructs, from which may be designed or chosen to fit one or more construct expressing therapeutic proteins possessing the capacity to effectively inhibit the release of pain mediators from nociceptors or cells releasing inducers of inflammation.

The invention, thus, also concerns the therapeutic Clostridial proteins produced using the oligonucleotides, methods of making the oligonucleotides and proteins, methods for the in vivo and/or in vitro expression of proteins encoded by these constructs, the purification of such proteins, and assays for their activity and physiochemical characterization, as well as methods to treat a patient suffering from, or at risk of suffering from chronic or inflammatory pain employing such proteins.

In a preferred embodiment, the construction of gene constructs according to the invention entails the steps (not necessarily in this order) modifying a nucleic acid encoding a single chain BoNT/X (for example, serotype /A, /B, /C1, /D, /E, /F and /G, or chimeric toxins comprising fragments from a plurality of toxin subtypes), removing or mutating the heavy chain $H_{CC}$ region (see above) and linking of a targeting ligand (TL) selective for sensory neurons or inflammation-mediating cells. Depending upon the identity of the toxin serotype, the LC of a more robust BoNT serotype (such as LC/E) can be appended to the LC/A to extend its longevity. These approaches are shown diagrammatically in FIG. 1.

Targeting ligands used in the present invention act to selectively direct the therapeutic biologic molecules of the present invention to sensory neurons and/or cells capable of secreting inflammation-mediating factors. Thus, for example, a nucleic acid encoding a TL is attached to the 3' end of a nucleic acid encoding a modified Clostridial toxin, such as one of those constructs described above, in order to permit the expressed proteins to selectively bind protein receptors of the nociceptive C-fibers, which are involved in chronic pain pathways. Exemplary TLs exhibiting the required selectivity against sensory neurons may include, without limitation: purotoxin-1 (PT-1) (an antagonist of the P2X3 purinergic receptor) or active fragments thereof; and antibodies or antibody fragments (such as single-chain variable fragments (scFv) of antibodies) reactive with P2X3 or transient receptor potential vanillinoid receptor 1 (TRPV1).

With respect to the purotoxin 1 receptor P2X3, this receptor is selectively expressed on sensory fibers of primary afferent neurons as both homo- and hetero-trimeric membrane channels, some of which are also sensitive to capsaicin (North R A, J. PHYSIOL. 554, 301-308, 2004). Peripheral nerve injury has been reported to alter the functional expression of P2X3 (Brederson et al., CURR. OPIN. INVESTIG. DRUGS 9, 716-725, 2008). Moreover, up-regulation of P2X3 receptor occurs during stretch of bladder urothelial cells (Sun and Chai. J. Urol. 171:448-452, 2004).

Importantly, inhibition of the P2X3 receptor's activity relieves the symptoms of inflammatory and neuropathic pain (North R A, J. PHYSIOL. 554, 301-308, 2004; Burnstock, G. PHARMACOL. THER. 110, 433-454, 2006). The beneficial antinociceptive effects of P2X3 antagonists, and characteristics of P2X3 knock-out mice, highlight a role in inflammatory and neuropathic pain for the neural fibers that express this receptor (Cockayne et al., NATURE 407, 1011-1015, 2000). Hence, a TL for use as a targeting element of an embodiment of the present invention may comprise the specific affinity of a P2X3 antagonist, PT-1 or derivative thereof. This P2X3 antagonist is derived from the central Asian spider *Geolycosa* (Grishin et al., ANN. NEUROL. 67, 680-683, 2010). The nucleic acid encoding this TL may comprise, consist essentially of, or consist of nucleic acid encoding a 35 residue peptide (SEQ. ID. No: 10); the amino acid sequence of this 35-residue peptide is disclosed herein as SEQ. ID. No. 9.

As disclosed in Example 2 of this application, an embodiment of this TL has been prepared by recombinant means in active form; and may be used to target the therapeutic biological molecules of the present invention selectively to neurons carrying the purotoxin 1 receptor P2X3. In this way a selective, long-lasting analgesic may be made and used that lacks the adverse effects and addictive properties of conventional chronic pain medications. These therapeutics also offer the major advantage that they do not affect, or do not substantially affect the secretion of cholinergic neurotransmitters in neuromuscular and autonomic nerves, unlike the unmodified BoNTs.

In other embodiments of the invention, a TL based upon the human CGRP (calcitonin gene-related peptide) protein fragment $CGRP_{8-37}$, an antagonist of the cell surface receptor CGRP receptor 1, may be used as a targeting ligand to direct the therapeutic of the present invention to sensory neurons and/or non-neuronal cells that secrete inflammatory mediators. Also useful as a TL for targeting the biotherapeutics to the latter cells, genes encoding the human interleukin-1 receptor antagonist (IL-1RA) (or a selectively functional derivative thereof) may also be employed in constructing the expressible nucleic acid.

Additional or alternative TLs may comprise, consist essentially of, or consist of single-chain antibodies (or derivatives thereof), or other ligands capable of selective binding to TRPV1 or P2X3 receptors; for example, a bivalent tarantula toxin by targeting the outer pore domain of TRPV1 (Bohlen et al., Cell. 141:834-845, 2010). Thus, targeting the biotherapeutic molecule to nociceptive neurons by exploiting the receptors' presence on these neurons (e.g. in TGNs) (Meng et al., 2007) and their roles in signaling of chronic inflammatory and neuropathic pain (North R A J. PHYSIOL. 554, 301-308, 2004). An attractive feature of TRPV1 targeting is that the trafficking of this cation-channel protein to the plasma membrane is partly SNARE-dependent, involving protein kinase C-controlled exocytosis, and the receptor is up-regulated in response to chronic pain (Morenilla-Palao et al., J BIOL CHEM 279, 25665-72, 2004; Szallasi et al., TRENDS MOL MED 12, 545-54, 2006). Thus, selectively targeting toxin derivatives to TRPV1-positive neurons may not only block release of pain neurotransmitters from these neurons but also down-regulate the expression of TRPV1, thus decreasing the sensitivity to hyperalgesia.

An αCGRP antagonist (residues 8-37), truncated version of CGRP (37 residues), is effective in antagonizing the action of basally-released CGRP in vitro from neurons in brainstem slices (Meng et al., 2009). This antagonist also can alleviate pain in vivo (Bird et al., MOL, PAIN 2, 31, 2006) by binding to the CGRP receptor 1 present on sensory ganglion and nociceptive presynaptic nerve terminals (Hay et al., BR J PHARMACOL 140, 477-86, 2003; Sams-Nielsen et al., BR J PHARMACOL 132, 1145-53, 2001; Zhang et al., J NEUROSCI 27, 2693-703, 2007).

The use of TLs comprising, consisting essentially of, or consisting of $\alpha CGRP_{8-37}$ (or derivatives thereof) to achieve targeted delivery of BoNT-derived core therapeutics into sensory neurons offers multiple advantages. For example, the resultant inhibition of CGRP release negates the vasodilation and mast cell degranulation associated with the activity of CGRP. Notably, the prevention of mast cell degranulation decreases the release of inflammatory affectors such as cytokines, including, without limitation, TNFα and IL-Iβ, that can act on sensory neurons. These factors, which induce the up-regulation of CGRP synthesis via MAPKs (mitogen-activated protein kinases) (Durham, P. L.; Russo, A. F. J NEUROSCI 23, 807-15, 2003), are thus involved in a feedback-regulated signaling cascade. The use of inhibitors of CGRP secretion in the present invention thus interrupts this expression and release cascade.

CGRP has been shown to be taken up by perivascular nociceptive nerve terminals, and this is efficiently reduced by $CGRP_{8-37}$, suggesting that receptor-mediated endocytosis of CGRP occurs (Sams-Nielsen et al., BR J PHARMACOL 132, 1145-53, 2001). The use of the biotherapeutics of the present invention, comprising an CGRP-binding TL should therefore successfully deliver the analgesic biologics of the invention into target cells (e.g., presynaptic nerve and mast cells). In Example 3 of this specification a synthetic DNA sequence encoding human $CGRP_{8-37}$ has been ligated to the 3' end of an embodiment of an expressible open coding region for the synthesis of a CGRP receptor-targeted analgesic biological therapeutic.

The interleukin-1 receptor antagonist (IL-1RA), a naturally-occurring receptor antagonist, binds to IL-1 receptor expressed on various cells e.g. macrophages, monocytes, synoviocytes, mast cells and neutrophils (Pou J et al., BIOCHIM BIOPHYS ACTA. 1811:556-63, 2011; Chin et al, J CLIN INVEST. 82:420-6, 1988; McColl et al., J EXP MED. 176:593-8, 1992). The antagonist IL-1RA competitively inhibits the binding of both IL-1α and IL-1β to the IL-1 receptor without inducing any detectable intracellular responses (Arend et al., ANNU. REV. IMMUNOL. 16:27-55, 1998).

According to the present invention, the targeted delivery of BoNT/X-derived therapeutics into inflammatory-mediating cells via IL-1RA binding to its receptor are expected to reduce the secretion of cytokines by cleaving the SNAREs which are essential for the release of these cytokines. As noted above, SNAP-23 and VAMP 3 were found to be essential for TNF-α and 21-6 release from human synovial cells (FIG. 8).

Although not necessarily limiting for the broadest embodiments, all of the constructs exemplifying the invention shown herein contain short sequences encoding amino acid residues, such as a "loop" region, situated between HC and LC of BONT/X (and located within (between) the cysteine residues involved in the di-sulfide bond bridging the LC and HC). The loop region is altered to contain a protease recognition amino acid sequence selectively or specifically recognized by an exogenous so the single-chain (SC) proteins expressed can be easily converted in vitro to the activated di-chain (DC) form by reaction with such an exogenous protease (for example, thrombin), for example in solution, or by using a column or batch reagent in which the exogenous protease is immobilized. Those of skill in the art are aware that any suitable exogenous protease may be used so long as it does not cleave the protein at undesired positions within the heavy or light chain regions.

The nucleic acid constructs of the present invention are constructed recombinantly, so as to permit the incorporation of alternations of the naturally-occurring BoNT/X sequences to provide therapeutic proteins for the treatment of chronic pain or inflammation when expressed in a suitable vector and host cell system. Examples of host cells which can be used for the expression of exogenous genes include, without limitation, insect cells, mammalian cells and cell lines, yeast cells, and bacterial cells, particularly the Gram-positive bacterium *Escherichia coli* (*E. coli*). Currently the Applicants prefer to use *E. coli* as a host cell expression system.

The therapeutic proteins expressed and/or made from the gene constructs described above offer several major advantages over the use of previously described agents for the treatment of pain, including previous Clostridial neurotoxin-based therapeutics. These advantages include, (a) directed and selective targeting to sensory neurons or inflammatory cells via an attached TL; (b) intra-cellular delivery and subsequent inhibition of the exocytosis of pain-stimulating peptides or cytokines, without substantially affecting other cells, such as motor and autonomic neurons, and (c) highly desirable and greatly extended life-time of the biotherapeutics (comparable to BoNT/A), which is a huge advantage decreasing the frequency of treatment or necessity for repeated treatment of chronic pain and inflammatory conditions.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

DETAILED DESCRIPTION OF THE INVENTION

EXAMPLE 1

Construction of $rA^-HC_N$ and Characterization of the Purified Recombinant Protein Recombinant nucleic acid $rA^-HC_N$ was created using "rA", a single chain construct of the synthetic BoNT/A nucleotide sequence in which the codons are optimized for expression in *E. coli*. The rA sequence is also engineered to possess one thrombin cleavage site in the loop region between the putative heavy chain and light chain regions of the toxin (LC-HC loop), and additional amino acids comprising a second thrombin cleavage site engineered near the carboxy terminus of the single chain toxin between the toxin sequences and a C-terminal $His_6$ (SEQ ID NO: 19) to permit cleavage of the $His_6$ (SEQ ID NO: 19) region and nicking of the inter-disulfide loop following purification. The rA sequence is cloned into *E. coli* expression vector pET29a(+) for propagation; pET29a(+) is a commercially available pBR322-derived plasmid vector containing a pBR322 plasmid origin, a bacteriophage f1 viral origin of replication, the T7 bacteriophage promoter, an N-terminal S-tag, a C-terminal $His_6$ tag (SEQ ID NO: 19) for purification of the gene product, a multiple cloning sequence (MCS) and the lac1 repressor gene. The vector can be obtained from, e.g., EMD4 Biosciences, Inc.

The nucleic acid sequence region encoding the $H_{CN}$ region (that is, encoding amino acids: $I_{874}$-$Q_{1091}$) is removed from the pET29a-rA vector (Wang et al 2011, J. BIOL, CHEM) by reverse PCR, using suitable primers complementary to each nucleic acid strand followed by self-ligation of the expression vector. As part of this portion of the engineering of the coding nucleic acid, two additional amino acid residues (Gly-Gly) were introduced in place of the $H_{CN}$ region between the $H_N$ and $H_{CC}$ domains of the heavy chain. The resulting DNA construct inherits the two thrombin cleavage sites from rA. FIG. 2A shows schematic diagrams of the single chain rA and rA$^-$H$_{CN}$ proteins showing the thrombin cleavage sites and the location of the inter-chain disulfide linkage.

After verification of the DNA sequences of the resulting rA$^-$HC$_N$ insert, vector containing the single chain (SC) gene was transformed into *E. coli* strain BL21(DE3), and expression was elicited by auto-induction (Wang et al., 2008). Cells were then pelleted by centrifuge, washed, and lysed using lysozyme and several freeze/thaw cycles. Insoluble material was removed by centrifugation and the supernatant used for subsequent steps. The SC was separated from the remainder of the supernatant by IMAC on TALON™ chromatography resin, and eluted with 500 mM imidazole. FIG. 2B shows an SDS-PAGE gel in which the left lane shows molecular weight markers and, from left to right, the cleared lysate (1), the column flow-through (2), the column pre-elution wash (3), the eluted fractions (4-9). The eluted rA$^-$HC$_N$ protein is then buffer exchanged into storage buffer (20 mM Hepes, 150 mM NaCl, pH 7.4), and incubated with thrombin (1 unit/mg toxin) at 22° C. for 1 hour for nicking the toxin. In some cases, the IMAC eluates were further purified by ion-exchange chromatography following the established protocol. For example, IMAC purified samples are buffer exchanged into 50 mM Tris-HCl buffer (pH 8.1) and loaded onto a resource Q column, and after washing with 30 mM NaCl, a stepwise gradient up to 1 M NaCl in 50 mM Tris-HCl buffer is applied. Pure samples are eluted by 70 mM NaCl (Wang et al 2008 and 2011).

FIG. 2C shows reducing and non-reducing SDS-PAGE gels of the purified toxin before (SC) and after nicking with thrombin (DC). Reduction was performed using dithiothreitol (DTT) to reduce and break the disulfide bonds linking the LC and HC. The DC lanes demonstrate that without reduction (−) the DC molecule migrates as a molecule of a single molecular weight (indicating that the disulfide bonds are intact); upon reduction (+) the gel demonstrates that the toxin derivative is nicked.

The IMAC-purified SC form of rA$^-$H$_{CN}$ was converted to the double chain (DC) form by incubation with thrombin. The DC toxin derivative displayed the ability to bind a recombinant fragment of the intra-luminal loop of SV2C (the BoNT/A protein receptor), by a pull-down assay and Western blotting (see FIG. 3A).

An example of such an assay is conducted as follows: The IMAC-purified SC form of rA$^-$H$_{CN}$ is converted to the double chain (DC) form by incubation with thrombin as above. Additionally, DC rA and rE proteins are also added to the assay as a control. GST-tagged, recombinantly expressed intra-luminal fragments of an acceptor for BoNT/A (GST-rat SV2C (454-579))are expressed and purified as disclosed in Wang, et al., J. BIOL. CHEM. 283:16993-17002 (2008). About 100 μg of this protein is immobilized using 100 μl of a slurry of glutathione SEPHAROSE®-4B Fast Flow chromatography resin (GE Healthcare) and incubated with 100 nM of rA, rE or the rA$^-$H$_{CN}$ toxin derivative in a total volume of 100 μl of binding buffer (50 mM Tris, 150 mM NaCl, 0.5% TRITON® X-100 surfactant, pH 7.6). In each case the resin beads are then collected by centrifugation and washed five times with >10 bed volumes of the same buffer for 15 min at 4° C.

Bound proteins are eluted from the washed beads by adding SDS-PAGE non-reducing sample buffer. Toxins are detected by Western blotting as shown in FIG. 3A. The left two Western blots are samples of rA, rA($^-$H$_{CN}$) and rE without performing the pull-down assay to confirm the specificity of antibodies used. This pair of Western blots show SDS-PAGE non-reducing gels with the lanes, from left to right, pre-stained molecular weight standards, rA, rA$^-$H$_{CN}$ and rE. The far left hand Western blot is developed using antibody selective to the light chain of BoNT/A (LC/A), and the right hand Western blot of this pair is developed using an antibody to the light chain of BoNT/E (LC/E). As expected, the anti-LC/A antibody detected both rA and rA$^-$H$_{CN}$, while not detecting rE. Similarly, the anti-LC/E antibody only detected rE, and not rA or rA$^-$H$_{CN}$.

The right hand pair of Western blots shows the results of the binding assays against immobilized SV2C acceptor component, and are run on the final column eluate. The Western blots are developed in the same manner, and the SDS-PAGE run in the same manner with the same lane order as in the left hand pair described above. The results show that rE was not bound by the immobilized SV2C acceptor component (see last lane, far right hand Western blot). However, the left hand Western blot of the pair shows that both rA and rA$^-$H$_{CN}$ bound the acceptor component and were successfully eluted, with the molecular weights of these polypeptides being identical to that of the species detected in the positive control.

The DC toxin derivative displayed the ability to bind a recombinant fragment of the intra-luminal loop of SV2C acceptor component by a pull-down assay and Western blotting. As a control, a purified form of rE (recombinant BoNT/E toxin in double chain form), which naturally binds glycosylated forms of the related protein receptors SV2A and SV2B, was incubated with the SV2C fragment under identical conditions, and did not bind this fragment. Thus, the interaction of rA$^-$H$_{CN}$ with SV2C is selective and does not occur with rE.

When rA$^-$H$_{CN}$ was added in serial dilutions to cultures of rat cerebellar granule neurons (CGNs), the toxin derivative substantially failed to cleave SNAP-25. FIG. 3B shows an experiment in which rat CGNs were incubated with ten-fold serial dilutions of rA or rA$^-$H$_{CN}$ (from 1000 pM to 0.01 pM, and with a negative control containing 0 pM) in culture medium at 37° C. for 24 hours. The cells were harvested and washed, then lysed in SDS-PAGE sample buffer; Western blots were developed using an antibody selective for the intact SNAP-25 and reactive with the SNAP-25 cleavage product of digestion with BoNT/A. The results showed that upon treatment of rat CGNs with the rA toxin intracellular SNAP-25 is cleaved at toxin concentrations at and above about 0.01 pM of the toxin, while SNAP-25 remains largely intact upon treatment of the CGN cells with rA⁻H$_{CN}$ of less than about 1000 pM. Since both proteins contain LC/A protease with similar activity towards recombinant substrates, the data suggest that the deletion of H$_{CN}$ from the rA⁻H$_{CN}$ derivative deprives and/or attenuates the toxin derivative of the ability to undergo internalization and/or translocation of LC within the CGN cells. Additionally, as shown in FIG. 3B, neither rA nor rA⁻H$_{CN}$ cleaved the SNARE protein syntaxin-1, which was added to the SDS-PAGE gels as a negative control.

Consistent with this hypothesis, intraperitoneal injection of each toxin into mice, in a mouse lethality assay, also showed the disproportional toxicity of the toxins. As shown in FIG. 3C, upon calculation of the mLD$_{50}$/mg (the mLD$_{50}$ is defined as the lowest dose of toxin effective to kill 50% of a group of 4 mice within 4 days), the deleted rA⁻H$_{CN}$ variant displayed approximately a $6.7 \times 10^4$-fold decrease in toxicity relative to rA.

These new findings suggested that the presence of the H$_{CN}$ portion of the heavy chain may be important for cell intoxication by BoNT/A (including rA) and its derivatives. Moreover, this experiment appears to dissect one or more elements of the multi-phasic intoxication mechanism of Clostridial neurotoxin (selective cell surface binding, internalization and translocation of LC to the cytosol and cleavage of the SNARE).

EXAMPLE 2

Construction of Toxin Derivatives LC.H$_N$.H$_{CN}$/A-PT-1 and LC.H$_N$/A-PT-1

The data disclosed in Example 1 show that it is possible to alter the specificity of BoNT/A (and, thus, of many or all other Clostridial neurotoxins) without altering the LC endopeptidase by removing the H$_{CC}$ region of the heavy chain binding region. Additionally, Applicants postulate that similar results would occur if the H$_{CC}$ region were mutated to rather than removed to eliminate the capability of the toxin to bind the protein receptor.

Figure 4:
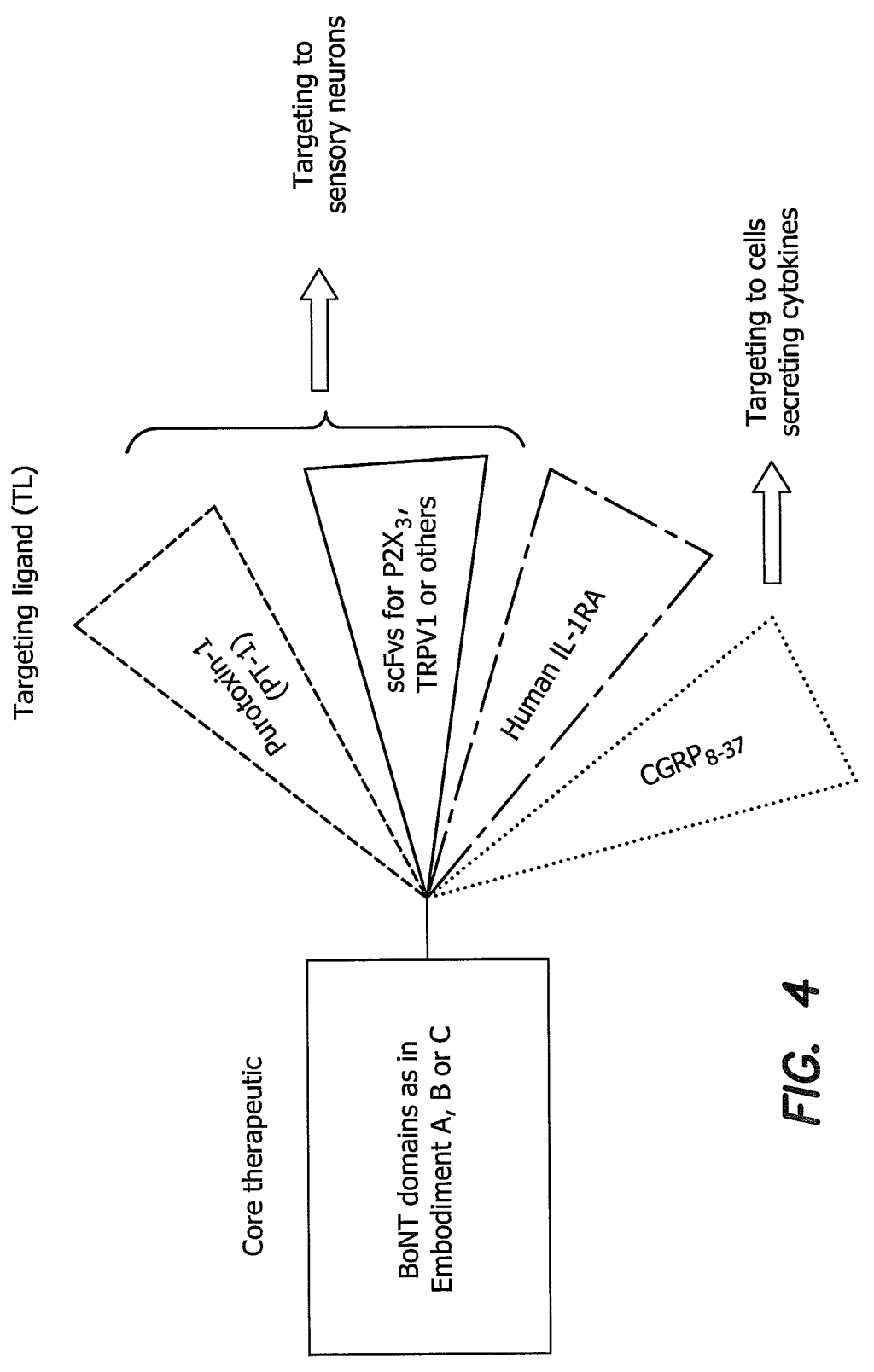

Applicants desired to investigate whether the altered toxin can be retargeted to selectively bind another cell type. As shown in FIG. 4, Applicants considered that such H$_{CC}$-lacking or H$_{CC}$-inactive neurotoxin variants can be linked to carefully chosen targeting ligands (TLs), for example targeted to purinergic receptors. In preferred embodiments, the purinergic receptor may be P2X3, and the ligand may be selected from peptides such as PT-1 and receptor P2X3-binding derivatives thereof and scFv fragments selective for P2X3. Additionally, the TL may be targeted to TRPV1 or other sensory neuron-selective cell surface antigens.

For generating LC.H$_N$.H$_{CN}$/A-PT-1 (FIG. 5A), a PCR product encoding a synthetic LC.H$_N$.H$_{CN}$/A gene was obtained, using the pET29a-BoNT/A construct as template and a pair of primers (T7 forward primer and a specific reverse primer with a designed Sac I restriction site). This was digested using endonucleases Xba I and Sac I and cloned into the pET29a(+) vector using these two restriction sites. The resultant construct was digested by Sac I and Xho I before ligation with a nucleic acid comprising an endonuclease Sac I- and Sal I-digested synthetic purotoxin-1 gene fragment (abbreviated "PT-1": shown as nucleotide sequence SEQ ID NO: 11 and amino acid sequence SEQ ID NO: 12) to generate a targeted LC.H$_N$.H$_{CN}$/A-PT-1 construct. Similarly, LC.H$_N$/A-PT-1 was created except the nucleotide sequence encoding LC.H$_N$ of BoNT/A was fused directly to PT-1 without the intervening H$_{CN}$ nucleotide sequences (FIG. 5A).

The nucleotide sequence of the resulting construct was verified by sequence analysis, then each of the above expression vector constructs were transformed into the Origami™ 2(DE3) E. coli host strain; this strain is a K-12 derivative that has mutations in both the thioredoxin reductase (trxB) and glutathione reductase (gor) genes, which greatly enhance disulfide bond formation in the E. coli cytoplasm. Plasmid protein expression was induced using auto-induction medium (Wang et al., JBC, 2008).

The expressed proteins were purified by IMAC as above, followed by SDS-PAGE analysis of LC.H$_N$.H$_{CN}$/A-PT-1 (FIG. 5B) and LC.H$_N$/A-PT-1 (FIG. 5C) on reducing and non-reducing gels, substantially as outlined in Example 1. Cells were then pelleted, washed, and lysed using lysozyme and several freeze/thaw cycles; insoluble material was removed by centrifugation. The proteins were trapped by IMAC on TALON™ chromatography resin, eluted with 500 mM imidazole, In each of FIG. 5B and 5C, lane 1 corresponds to the cleared lysate, 2 to the flow-through fraction, 3 to the wash fraction, and fractions 4-8 to the eluate fractions. The unlabeled lane on each gel comprises molecular weight standards.

As can be seen, unlike the experiments using expressed rA⁻H$_{CN}$, both of LC.H$_N$.H$_{CN}$/A-PT-1 and LC.H$_N$/A-PT-1 were expressed largely in the DC form, as reflected by the appearance under reducing conditions of LC and H$_N$.H$_{CN}$/A-PT-1 or H$_N$/A-PT-1 in SDS-PAGE (FIG. 5B and FIG. 5C). This fact suggests that in this experiment the intra-loop thrombin site in each construct was cleaved after expression or during purification without the need for an in vitro cleavage step. The presents of discrete LC and "HC" species was confirmed using Western blotting; FIG. 6A shows that anti-LC/A antibody detects the disulfide-linked double chain LC.H$_N$.H$_{CN}$/A-PT-1 in non-reducing gels, but only the LC in reducing gels. Similarly, anti-His6 antibody ("His6" disclosed as SEQ ID NO: 19) detects the disulfide-linked double chain LC.H$_N$.H$_{CN}$/A-PT-1 in non-reducing gels, but only the H$_N$.H$_{CN}$/A-PT-1 under reducing conditions. Coomassie blue staining of the gel shows both chains to be present under reducing conditions. FIG. 6B shows the same experiment using the purified LC.H$_N$/A-PT-1, with similar results.

Incubation of 1.6 nM LC.H$_N$.H$_{CN}$/A-PT-1 or LC.H$_N$/A-PT-1 with sensory neurons from rat trigeminal ganglia was conducted as described above. As shown in FIG. 6C, only the cells incubated with LC.H$_N$.H$_{CN}$/A-PT-1 showed detectable cleavage of SNAP-25 using this concentration of protein. In contrast, LC.H$_N$/A-PT-1 failed to cleave SNAP-25 within the rat trigeminal ganglia cells despite carrying the same LC. The result is shown quantitatively in FIG. 6D. These findings suggest than H$_{CN}$ plays an important role in permitting the LC.H$_N$.H$_{CN}$/A-PT-1 polypeptide to enter sensory neurons and cleave its intracellular target; the lack of H$_{CN}$ results in a greatly attenuated or absent ability for the protein to enter the cell. Thus, Applicants have found the presence of H$_{CN}$ to be very important for permitting Clostridial toxin-based therapeutics (even those like LC.H$_N$/A-PT-1 that bear a TL selective for a protein receptor displayed by the target cell) to enter the parent cell.

In this specification (unless indicated otherwise) all amino acid sequences are shown in the direction from the amino terminus to the carboxy terminus, and the nucleotide sequences are shown in the direction 5' to 3'.

Figure 7B:
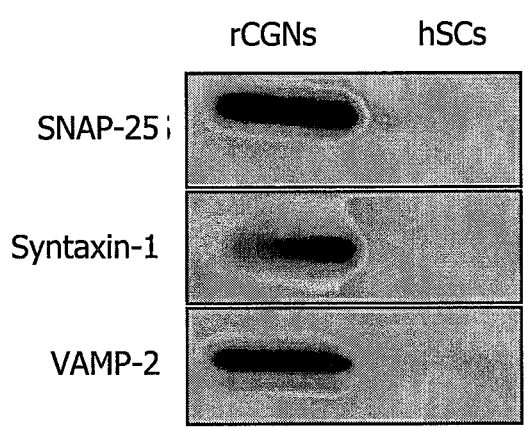
FIG. 7B shows Western blots of SDS-PAGE gels from lysates of: human synovial cell line (hSC) and rat cerebellar ganglia neurons (rCGNs), which contain the SNARE proteins SNAP-25, syntaxin 1, and VAMP 2. In each case, Western blots were developed using antibodies directed against in the indicated SNARE proteins.

Synthetic Purotoxin-1 Nucleic Acid Fragment (with Stop Codons) and its Encoded Amino Acids SEQ ID NO: 9 and 10 are the nucleotide sequence and the amino acid sequence, respectively, of the synthetic purotoxin-1 nucleic acid fragment and its encoded amino acids, including additional linker regions. The following shows an alignment of these sequences with relevant restriction endonuclease sites shown, as follows: Nucleotides 1-18 comprise restriction sites for Sal I, Sac I and EcoRV; nucleotides 19-63: three iterations of nucleotides encoding the amino acid sequence Gly$_4$Ser (SEQ ID NO: 20) (a non-structured linker); nucleotides 64-171 (shown underlined and in bold): the purotoxin-1 fragment, including a stop codon (*); nucleotides 172-177: the restriction site for endonuclease Xho I.

nantly contain SNAP-23, VAMP 3 and syntaxin 2, 3 and 4. As shown in FIG. 7, the SNAREs SNAP-25, syntaxin 1 and VAMP 2 were not detected to an appreciable degree in hSC cells. Similarly, in a macrophage cell line RAW264.9 (mMC) SNAP-23, VAMP 3, syntaxin 2, syntaxin 3 and syntaxin 4 are detected.

Additional cell types analyzed for SNARE proteins included rat cerebellar granule neurons (rCGNs). As shown in FIG. 7, which contained SNAP-25, VAMP 2 and syntaxin 1.

```
     V   D    E   L    D   I    G   G   G   G   S   G   G   G   G   S   G   G   G   G   S   G   Y   C   A   E   K
  1GTCGAC GAGCTC GATATC GGTGGTGGTGGTAGCGGTGGTGGCGGTTCAGGTGGTGGTGGCAGTGGTTATTGTGCAGAAAA  80
    SalI    Sac I  EcoRV

G   I   R   C   D   D   I   H   C   C   T   G   L   K   C   K   C   N   A   S   G   Y   N   C   V   C
 81AGGTATTCGCTGTGATGATATTCATTGTTGCACCGGTCTGAAATGTAAATGTAATGCCAGCGGTTATAATTGCGTGTGCC          160

R   K   K    *   L   E              (SEQ ID NO: 10)
161GCAAAAGTAA CTCGAG    177  (SEQ ID NO: 9)
                XhoI
```

Synthetic Purotoxin-1 Nucleic Acid Fragment
(without Stop Codons) and its Encoded Amino Acids SEQ ID NO: 11 and 12 are the nucleotide sequence and the amino acid sequence, respectively, of the synthetic purotoxin-1 nucleic acid fragment and its encoded amino acids, including additional linker regions. The following shows an alignment of these sequences with relevant restriction endonuclease sites shown, as follows: Nucleotides 1-18 comprise restriction sites for Sal I, Sac I and EcoRV; nucleotides 19-63: three iterations of nucleotides encoding the amino acid sequence Gly$_4$Ser (SEQ ID NO: 20) (a non-structured linker); nucleotides 64-168 (shown underlined and in bold): the purotoxin-1 fragment (without a stop codon); nucleotides 169-174: the restriction site for endonuclease Sal I.

As shown in FIG. 8A-8D, hSC cells were incubated for 7-10 days with shRNA (small hairpin RNA) lentivirus carrying nucleotide sequences specifically targeting the down-regulation of SNAP-23 expression. The cells were then incubated overnight with IL-1β (100 ng/ml) in culture medium to induce secretion of TNF-α and IL-6. After collecting the supernatant, lysates from these cells were subjected to SDS-PAGE and proteins detected by Western blot analysis using antibodies directed to SNAP-23, VAMP 3 or the untargeted control protein β-tubulin. KD stands for shRNA-induced "knock down" or inhibition of expression. The gel results (FIGS. 8A and 8C) show that expression of SNAP-23 and VAMP 3 is diminished substantially in cells treated with the shRNA as compared to untreated cells (control). Additionally, in FIGS. 8B and 8D the levels of tissue necrosis factor

```
     V   D    E   L    D   I    G   G   G   G   S   G   G   G   G   S   G   G   G   G   S   G   Y   C   A   E   K
  1GTCGAC GAGCTC GATATC GGTGGTGGTGGTAGCGGTGGTGGCGGTTCAGGTGGTGGTGGCAGTGGTTATTGTGCAGAAAA  80
    Sal I   SacI  EcoRV

G   I   R   C   D   D   I   H   C   C   T   G   L   K   C   K   C   N   A   S   G   I   N   C   V   C
 81AGGTATTCGCTGTGATGATATTCATTGTTGCACCGGTCTGAAATGTAAATGTAATGCCAGCGGTTATAATTGCGTGTGCC          160

R   K   K    V   D               (SEQ ID NO: 12)
161GCAAAAAG GTCGAC      174  (SEQ ID NO: 11)
              Sal I
```

EXAMPLE 3

Targeting BoNT-derived Inhibitors of Exocytosis to Cells Secreting Inflammatory Affectors The release of cytokines and other mediators of inflammation is associated with several types of chronic pain. The release of many of these mediators involves SNARE-dependent exocytosis (Stow et al., NATURE REVIEWS Immunol. 6, 919-29, 2006). In another embodiment of the present invention, Clostridial toxin-derived therapeutics may be targeted to cells involved in the release of these actors by attaching TLs having an selective affinity for such cells, such as the peptides IL-1RA or CGRP antagonist (see above), which bind to their requisite receptors on the surface of non-neuronal cells secreting pain and/or inflammatory mediators. Such cells may be neurons or non-neurons.

Figure 8B:
FIG. 8B is a graphical representation of the inhibition of expression (expressed as percentage "knock down" or KD) of SNAP-23 in the experiment shown in FIG. 8A. Also shown is the percent inhibition of secretion of TNF-α and IL-6 from these cells before lysis, relative to supernatant from a control cell culture not treated with the lentivirus vector. Note, the quantification of secreted TNF-α and IL-6 was performed using enzyme-linked immunosorbent assay (ELISA) according to a protocol provided by Mabtech AB (Sweden).
Figure 8D:
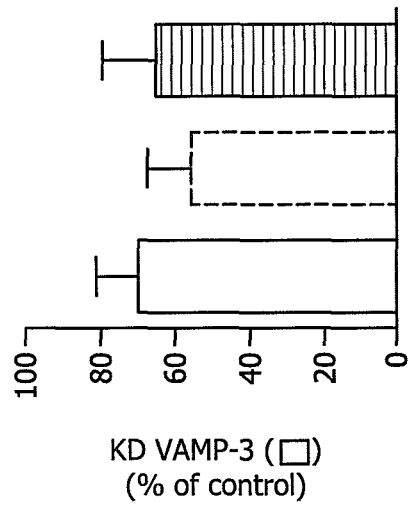
FIG. 8D is a graphical representation of the inhibition of expression (expressed as percentage "knock down" or KD) of VAMP 3 in the experiment shown in FIG. 8C. Also shown is the percent inhibition of secretion of TNF-α and IL-6 (quantified by ELISA as described in FIG. 8B) from these cells before lysis, relative to supernatant from a control cell culture not treated with the lentivirus vector.
Figure 8A:
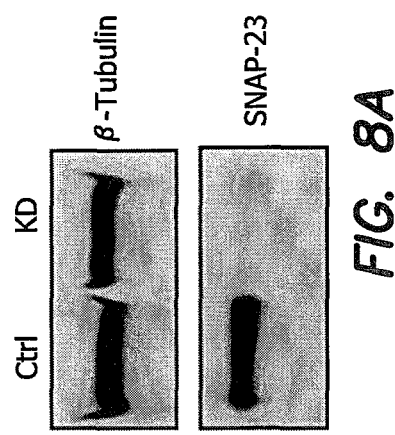
FIG. 8A is a Western blot showing the results of an experiment in which hSC cells were incubated for 7-10 days with shRNA (small hairpin RNA) lentivirus carrying nucleotide sequences specifically targeting SNAP-23. The cells were then incubated overnight with IL-Iβ (100 ng/ml) in complete culture medium to induce secretion of TNF-α and IL-6. After collecting the supernatant, lysates from these cells were subjected to SDS-PAGE and proteins detected using antibodies directed to SNAP-23 or the untargeted control protein β-tubulin. KD stands for shRNA-induced "knock down" or inhibition of expression.
Figure 8C:
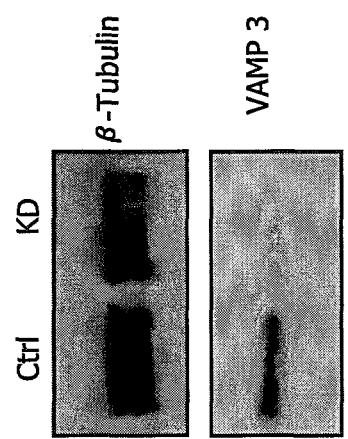
FIG. 8C is a Western blot showing the results of an experiment in which hSC cells were incubated for 7-10 days with shRNA (small hairpin RNA) lentivirus carrying nucleotide sequences specifically targeting VAMP 3. The cells were then incubated overnight with IL-Iβ (100 ng/ml) in complete culture medium to induce secretion of TNF-α and IL-6. After collecting the supernatant, lysates from these cells were subjected to SDS-PAGE and proteins detected using antibodies directed to VAMP 3 or the untargeted control protein β-tubulin. KD stands for shRNA-induced "knock down" or inhibition of expression.

Towards this end, a human synovial cell line (hSC) was analyzed for SNARE protein species and found to predomialpha (TNF-α) and interleukin-6 (IL-6) quantified by ELISA in shRNA-treated cells are compared with the levels in untreated cells, and the reduction expressed as percentage inhibition relative to control; FIG. 8B also shows the percent knock-down) of SNAP-23 and FIG. 8D the percent knock-down of VAMP 3, relative to untreated cells. These observations provide evidence for VAMP 3 and SNAP-23 being required in exocytosis of both of these cytokines tested. The levels of SNAP-23 or VAMP 3 in shRNA-treated cells relative to an internal reference protein (β-Tubulin) were compared with that in untreated cells, and the reduction expressed as percentage KD relative to control.

Thus, as illustrated by these findings, certain embodiments of the present invention involves compositions and methods for inhibiting the release of cytokines using a BoNT-derived analgesic therapeutic targeted to these cells via an joined TL such as IL-1RA or a CGRP antagonist; see FIG. 4.

For example, the cleavage of VAMP 3 in cells secreting inflammatory factors may be accomplished by ligating a prepared synthetic nucleic acid segment encoding the VAMP 3-cleaving protease LC/D in a therapeutic construct such as BoNT/D($^-$H$_{CC}$), to a synthetic nucleic acid encoding a binding-capable polypeptide (IL-1RA) having selective affinity for human IL-1 receptor (the entire sequence is shown herein as SEQ ID NO: 13 with the translated amino acid sequence shown as SEQ ID NO: 14).

As an alternative TL to prevent the secretion of inflammatory factors from cells, use of an antagonist to the CGRP receptor 1 provides a similar means of targeting non-neuronal cells and sensory neurons. Disclosed herein, a synthetic nucleic acid encoding a binding portion of the coding sequence of human CGRP antagonist (CGRP$_{8-37}$); this sequence is shown as SEQ ID NO: 15, and its translated amino acid sequence is provided as SEQ ID NO: 16. The nucleic acid fragment was fused via restriction endonuclease digestion and ligation to BoNT/D($^-$H$_{CC}$) to generate a fusion gene, BoNT/D(-H$_{CC}$)-CGRP$_{8-37}$. The sequence of the (SEQ ID NO: 17, and its translated amino acid sequence is provided as SEQ ID NO: 18).

These two hybrid nucleic acids are separately cloned into expression vector pET29a(+) and expressed in *E. coli* strain BL 21(DE3). An additional or alternative strategy for inhibiting cytokine release may rely on inactivating SNAP-23; in this approach, an LC/E moiety, capable of cleaving SNAP-23, may be attached to BoNT/A$^-$H$_{CC}$-IL-1RA or BoNT/X (PrR$^-$)-IL-1RA. For example, mutating residue of Lys224 in LC/E moiety to Asp significantly increased its cleavage of human SNAP-23 (Chen and Barbieri, Proc. Nat. Acad. Sci. USA, 106:9180-9184, 2009). This mutant LC/E may be attached to BoNT/B (Lys$^{1192}$→Glu and/or Ala$^{1196}$→Lys: PrR$^-$)-IL-1RA (see earlier text about PrP$^-$). These constructs may be used in conjunction with biotherapeutics having the ability to cleave other SNARE proteins to provide a stronger therapeutic effect. Furthermore, since the IL-1 receptor also reside on macrophages which also possess BoNT-susceptible SNAREs (see FIG. 7), a similar approach as outlined above for the hSC may be adopted to target these cells.

All of these constructs comprise BoNT/X-TL hybrids (or nucleic acids encoding such hybrids) either lacking the H$_{CC}$ region, or having an inactive H$_{CC}$ region. The polypeptides preferably are constructed to contain short loop inter-chain sequences possessing a protease-liable, selective cleavage site situated between HC and LC of BoNT so the expressed single-chain proteins can be converted in vitro to the activated di-chain form as necessary.

In the following nucleotide sequences, SEQ ID NO: 13, SEQ ID NO: 15 and SEQ ID NO: 17 and their respective amino acid sequences, SEQ ID NO: 14, SEQ ID NO: 16 and SEQ ID NO: 18), the amino acids are identified using the single letter amino acid designations, with the amino acid sequence shown in the direction from the amino terminus to the carboxy terminus, and the nucleotide sequence shown in the direction 5' to 3'.

```
Synthetic BoNT/D(⁻H_CC)- human IL-1RA gene sequence and its encoded amino acids (SEQ ID NO: 13 AND 14)

M  T  W  P  V  K  D  F  N  Y  S  D  P  V  N  D  N  D  I  L  Y  L  R  I  P  Q  N
  1       ATGACCTGGCCGGTGAAAGACTTTAACTATAGCGATCCGGTGAACGATAACGATATTCTGTATCTGCGTATCCCGCAGAA        80

K  L  I  T  T  P  V  K  A  F  M  I  T  Q  N  I  W  V  I  P  E  R  F  S  S  D
  81      CAAACTGATTACCACCCCGGTGAAAGCGTTCATGATTACCCAGAACATTTGGGTGATTCCGGAACGTTTTAGCAGCGATA       160

T  N  P  S  L  S  K  P  P  R  P  T  S  K  Y  Q  S  Y  Y  D  P  S  Y  L  S  T  D
  161     CCAATCCGAGCCTGAGCAAACCGCCGCGTCCGACCAGCAAATATCAGAGCTATTACGATCCGAGCTATCTGAGCACCGAT       240

E  Q  K  D  T  F  L  K  G  I  I  K  L  F  K  R  I  N  E  R  D  I  G  K  K  L  I
  241     GAACAGAAAGATACCTTCCTGAAAGGCATCATCAAACTGTTCAAACGCATTAACGAACGCGATATTGGCAAAAAACTGAT       320

N  Y  L  V  V  G  S  P  F  M  G  D  S  S  T  P  E  D  T  F  D  F  T  R  H  T
  321     CAACTATCTGGTGGTGGGCAGCCCGTTTATGGGCGATAGCAGCACCCCGGAAGATACCTTTGATTTTACCCGICATACCA       400

T  N  I  A  V  E  K  F  E  N  G  S  W  K  V  T  N  I  I  T  P  S  V  L  I  F  G
  401     CGAACATTGCGGTGGAAAAATTTGAAAACGGCAGCTGGAAAGTGACCAACATTATTACCCCGAGCGTGCTGATTTTTGGC        480

P  L  P  N  I  L  D  Y  T  A  S  L  T  L  Q  G  Q  Q  S  N  P  S  F  E  G  F  G
  481     CCGCTGCCGAACATTCTGGATTATACCGCGAGCCTGACGCTGCAAGGCCAGCAGAGCAATCCGAGCTTTGAAGGCTTTGG       560

T  L  S  I  L  K  V  A  P  E  F  L  L  T  F  S  D  V  T  S  N  Q  S  S  A  V
  561     CACCCTGAGCATTCTGAAAGTGGCGCCGGAATTTCTGCTGACCTTTAGCGATGTGACCAGCAACCAGAGCAGCGCGGTGC       640

L  G  K  S  I  F  C  M  D  P  V  I  A  L  M  H  E  L  T  H  S  L  H  Q  L  Y  G
  641     TGGGCAAAAGCATTTTTTGCATGGATCCGGTGATTGCGCTGATGCATGAACTGACCCATAGCCTGCATCAGCTGTATGGC       720

I  N  I  P  S  D  K  R  I  R  P  Q  V  S  E  G  F  F  S  Q  D  G  P  N  V  Q  F
  721     ATTAACATTCCGAGCGATAAACGTATTCGTCCGCAGGTGAGCGAAGGCTTTTTTAGCCAGGATGGCCCGAACGTGCAGTT       800

E  E  L  Y  T  F  G  G  L  D  V  E  I  I  P  Q  I  E  R  S  Q  L  R  E  K  A
```

| | Synthetic BoNT/D($^-$H$_{CC}$)- human IL-1RA gene sequence and its encoded amino acids (SEQ ID NO: 13 AND 14) | |
|---|---|---|
| 801 | TGAAGAACTGTATACCTTTGGCGGCCTGGATGTGGAAATTATTCCGCAGATTAACGTAGCCAGCTGCGTGAAAAAGCGC | 880 |
| | L G H Y K D I A K R L N N I N K T I P S S W I S N I D | |
| 881 | TGGGCCACTATAAAGATATTGCGAAACGCCTGAACAACATCAACAAACCATTCCGAGCAGCTGGATTAGCAACATCGAT | 960 |
| | K Y K K I F S E K Y N F D K D N T G N F V V N I D K F | |
| 961 | AAATACAAAAAAATCTTCAGCGAAAAATATAACTTCGATAAAGATAACACCGGCAACTTCGTGGTGAACATTGATAAATT | 1040 |
| | N S L Y S D L T N V M S E V V Y S S Q Y N V K N R T | |
| 1041 | CAACAGCCTGTATAGCGATCTGACCAACGTGATGAGCGAAGTGGTGTATAGCAGCCAGTATAACGTGAAAAACCGCACCC | 1120 |
| | H Y F S R H Y L P V F A N I L D D N I Y T I R D G F N | |
| 1121 | ATTATTTCAGCCGTCATTATCTGCCGGTGTTTGCGAATATTCTGGATGATAACATCTATACCATCCGTGATGGCTTTAAC | 1200 |
| | L T N K G F N I E N S G Q N I E R N P A L Q K L S S E | |
| 1201 | CTGACCAACAAAGGCTTTAACATTGAAAACAGCGGCCAGAACATTGAACGTAATCCGGCGCTGCAGAAACTGTCTAGCGA | 1280 |
| |                                     Thrombin cleavage site<br>S V V D L F T K V C L R L T L V P R ↓ G S T C I K V K | |
| 1281 | AAGCGTGGTGGACCTGTTTACCAAAGTGTGCCTGCGTCTGACCCTGGTGCCACGCGGTAGCACCTGCATCAAAGTGAAAA | 1360 |
| | N N R L P Y V A D K D S I S Q E I F E N K I I T D E T | |
| 1361 | ACAACCGTCTGCCGTATGTGGCGGATAAAGATAGCATTAGCCAGGAAATCTTCGAAAACAAAATCATCACCGATGAAACC | 1440 |
| | N V Q N Y S D K F S L D E S I L D G Q V P I N P E I V | |
| 1441 | AACGTGCAGAACTACAGCGATAAATTCAGCCTGGATGAAAGCATTCTGGATGGCCAGGTGCCGATTAATCCGGAAATTGT | 1520 |
| | D P L L P N V N M E P L N L P G E E I V F Y D D I T | |
| 1521 | GGATCCGCTGCTGCCGAACGTGAACATGGAACCGCTGAACCTGCCGGGCGAAGAAATTGTGTTCTATGATGATATTACCA | 1600 |
| | K Y V D Y L N S Y Y Y L E S Q K L S N N V E N I T L T | |
| 1601 | AATATGTGGATTATCTGAACAGCTACTACTATCTGGAAAGCCAGAAACTGAGCAACAACGTGGAAAACATTACCCTGACC | 1680 |
| | T S V E E A L G Y S N K I Y T F L P S L A E K V N K G | |
| 1681 | ACCTCTGTGGAAGAAGCGCTGGGTTATAGCAACAAAATCTACACCTTTCTGCCGAGCCTGGCCGAAAAAGTGAACAAAGG | 1760 |
| | V Q A G L F L N W A N E V V E D F T T N I M K K D T | |
| 1761 | CGTGCAGGCGGGCCTGTTTCTGAACTGGGCGAACGAAGTGGTGGAAGATTTTACCACCAATATCATGAAAAAAGATACCC | 1840 |
| | L D K I S D V S V I I P Y I G P A L N I G N S A L R G | |
| 1841 | TGGATAAAATCAGCGATGTGAGCGTGATTATTCCGTATATTGGTCCGGCGCTGAACATTGGCAACAGCGCCCTGCGTGGC | 1920 |
| | N F N Q A F A T A G V A F L L E G F P E F T I P A L G | |
| 1921 | AACTTTAACCAGGCGTTTGCGACCGCGGGTGTGGCGTTTCTGCTGGAAGGCTTTCCGGAATTCACCATTCCGGCGCTGGG | 2000 |
| | V F T F Y S S I Q E R E K I I K T I E N C L E Q R V | |
| 2001 | CGTGTTTACCTTTTATAGCAGCATTCAGGAACGCGAAAAAATCATCAAAACCATCGAAAACTGCCTGGAACAGCGTGTGA | 2080 |
| | K R W K D S Y Q W M V S N W L S R I T T Q F N H I N Y | |
| 2081 | AACGTTGGAAAGATAGCTATCAGTGGATGGTGAGCAACTGGCTGTCTCGTATTACCACCCAGTTTAACCACATCAACTAT | 2160 |
| | Q M Y D S L S Y Q A D A I K A K I D L E Y K K Y S G S | |
| 2161 | CAGATGTATGACAGCCTGAGCTATCAGGCGGATGCGATTAAAGCGAAAATCGATCTGGAATACAAAAAATACAGCGGCAG | 2240 |
| | D K E N I K S Q V E N L K N S L D V K I S E A M N N | |
| 2241 | CGATAAGAAAACATCAAAAGCCAGGTGGAAAACCTGAAAAACAGCCTGGATGTGAAAATTAGCGAAGCCATGAATAACA | 2320 |
| | I N K F I R E C S V T Y L F K N M L P K V I D E L N K | |

-continued

Synthetic BoNT/D(⁻H_CC)- human IL-1RA gene sequence and its encoded amino acids (SEQ ID NO: 13 AND 14)

```
2321  TCAACAAATTCATCCGTGAATGCAGCGTGACCTACCTGTTTAAAAACATGCTGCCGAAAGTGATTGATGAACTGAACAAA  2400
        F  D  L  R  T  K  T  E  L  I  N  L  I  D  S  H  N  I  I  L  V  G  E  V  D  R  L
2401  TTTGATCTGCGCACCAAAACCGAACTGATTAACCTGATCGATAGCCATAACATTATTCTGGTGGGCGAAGTGGATCGTCT  2980
         K  A  K  V  N  E  S  F  E  N  T  M  P  F  N  I  F  S  Y  T  N  N  S  L  L  K
2481  GAAAGCGAAAGTGAACGAAAGCTTCGAAAACACCATGCCGTTTAACATCTTCAGCTACACCAACAACAGCCTGCTGAAAG  2560
        D  I  I  N  E  Y  F  N  S  I  N  D  S  K  I  L  S  L  Q  N  K  K  N  A  L  V  D
2561  ATATTATCAACGAATATTTTAACAGCATCAACGATAGCAAAATTCTGAGCCTGCAGAACAAAAAAAACGCGCTGGTTGAT  2640
         T  S  G  Y  N  A  E  V  R  V  G  D  N  V  Q  L  N  T  I  Y  T  N  D  F  K  L  S
2641  ACCAGCGGCTATAACGCGGAAGTGCGTGTGGGCGATAACGTGCAGCTGAACACCATTTATACCAACGATTTCAAACTGAG  2720
          S  S  G  D  K  I  I  V  N  L  N  N  N  I  L  Y  S  A  I  Y  E  N  S  S  V  S
2721  CAGCAGCGGCGATAAAATTATTGTGAACCTGAATAACAACATTCTGTACAGCGCGATTTATGAAAACAGCAGCGTGAGCT  2800
         F  W  I  K  I  S  K  D  L  T  N  S  H  N  E  Y  T  I  I  N  S  T  E  Q  N  S  G
2801  TTTGGATCAAAATCAGCAAAGATCTGACCAACAGCCATAACGAATACACCATCATCAACAGCATTGAACAGAACAGCGGC  2880
          W  K  L  C  I  R  N  G  N  I  E  W  I  L  Q  D  V  N  R  K  Y  K  S  L  I  F  D
2881  TGGAAACTGTGCATTCGTAACGGCAACATTGAATGGATTCTGCAGGATGTGAACCGCAAATATAAAAGCCTGATCTTCGA  2960
         Y  S  E  S  L  S  H  T  G  Y  T  N  K  W  F  F  V  T  I  T  N  N  I  M  G  Y
2961  TTATAGCGAAAGCCTGAGCCATACCGGCTATACCAACAAATGGTTCTTTGTGACCATCACCAACAACATTATGGGCTATA  3040
         M  K  L  Y  I  N  G  E  L  K  Q  S  Q  K  I  E  D  L  D  E  V  K  L  D  K  T  I
3041  TGAAACTGTATATCAACGGCGAACTGAAACAGAGCCAGAAAATCGAAGATCTGGATGAAGTGAAACTGGATAAAACCATC  3120
          V  F  G  I  D  E  N  I  D  E  N  Q  M  L  W  I  R  D  F  N  I  F  S  K  E  L  S
3121  GTGTTTGGCATCGATGAAAACATTGATGAAAACCAGATGCTGTGGATTCGCGATTTTAACATCTTTAGCAAAGAACTGAG  3200
           N  E  D  I  N  I  V  Y  E  G  Q  I  E  L  G  G  G  G  S  G  G  G  G  S  R  P
3201  CAACGAAGATATTAACATCGTGTACGAAGGCCAGATTGAGCTCGGTGGTGGTGGTAGCGGTGGTGGCGGTAGT<u>CGTCCGA</u>  3280
        S  G  R  K  S  S  K  M  Q  A  F  R  I  W  D  V  N  Q  K  T  F  Y  L  R  N  N  Q
3281  <u>GCGGTCGTAAAAGCAGCAAAATGCAGGCATTTCGTATTTGGGATGTGAATCAGAAAACCTTTTATCTGCGCAACAATCAG</u>  3360
           L  V  A  G  Y  L  Q  G  P  N  V  N  L  E  E  K  I  D  V  V  P  I  E  P  H  A  L
3361  <u>CTGGTTGCAGGTTATCTGCAGGGTCCGAATGTTAATCTGGAAGAAAAAATTGATGTGGTGCCGATTGAACCGCATGCACT</u>  3440
         F  L  G  I  H  G  G  K  M  C  L  S  C  V  K  S  G  D  E  T  R  L  Q  L  E  A
3441  <u>GTTTCTGGGTATTCATGGTGGTAAAATGTGTCTGAGCTGTGTTAAAAGCGGTGATGAAACCCGTCTGCAGCTGGAAGCAG</u>  3520
           V  N  I  T  D  L  S  E  N  R  K  Q  D  K  R  F  A  F  I  R  S  D  S  G  P  T  T
3521  <u>TGAATATCACCGATCTGAGCGAAAATCGTAAACAGGATAAACGCTTTGCCTTTATTCGTAGCGATAGCGGTCCGACCACC</u>  3600
          S  F  E  S  A  A  C  P  G  W  F  L  C  T  A  M  E  A  D  Q  P  V  S  L  T  N  M
3601  <u>AGTTTTGAAAGCGCAGCATGTCCGGGTTGGTTTCTGTGTACCGCAATGGAAGCAGATCAGCCGGTTAGCCTGACCAATAT</u>  3680
                                                           Thrombin cleavage site
                                                                    ↓
           P  D  E  G  V  M  V  T  K  F  Y  F  Q  E  D  E  V  D  L  V  P  R  G  S  K  L
3681  <u>GCCGGATGAAGGTGTTATGGTGACCAAATTCTATTTTCAGGAAGATGAAGTCGACCTGGTGCCACGCGGTAGCAAGCTTG</u>  3760
            A  A  A  L  E  H  H  H  H  H  H  *
3761  CGGCCGCACTCGAGCACCACCACCACCACCACTGA  3795
```

The synthetic nucleotide sequence provided above contains the following regions, respectively (identified with respect to the nucleotide residues and the peptides encoded therein) residues 1-3237: LC.H$_N$.H$_{CN}$/D; residues 3274-3729 (underlined), human IL-1RA. DNA sequences between these areas (for example, the sequence comprising nucleotides 3238-3273) are introduced as a linker between the TL and the remainder of the construct and ensures the proper reading frame. The amino acid sequences are displayed in alignment above the corresponding nucleotides. A thrombin protease recognition sequence is shown engineered into the loop between LC/D and H$_N$/D; similarly, another thrombin site was engineered to have a cleavage sequence to the carboxy site of the human IL-1RA gene for simultaneous nicking and removal of C-terminal His$_6$ (SEQ ID NO: 19); the arrows indicate cleavage sites.

```
        Synthetic CGRP antagonist (CGRP8-37) fragment and its encoded amino acids
                                                           (SEQ ID NO: 15 and SEQ ID NO: 16)
            E  L  D  I  G  G  G  G  S  G  G  G  G  S  G  G  G  G  S  V  T  H  R  L  A  G  L
          1 GAGCTCGATATCGGTGGTGGTGGTAGCGGTGGTGGCGGTTCAGGTGGTGGTGGCAGCGTTACCCATCGTCTGGCTGGTCT     80
            SacI    EcoRV L  S  R  S  G  G  V  V  K  N  N  F  V  P  T  N  V  G  S  K  A  F  *
         81 GCTGTCTCGTAGCGGTGGTGTTGTGAAAAACAATTTTGTGCCGACAAATGTTGGTAGCAAAGCATTTTAA CTCGAG         156
                                                                                Xho I
```

The synthetic nucleotide sequence provided above contains the following regions, respectively (identified with respect to the nucleotide residues—residues 1-12: restriction sites for Sac I and EcoRV; residues 13-57: (Gly4Ser)×3 (SEQ ID NO: 21) non-structured linker; residues 58-150 (underlined and bold): the CGRP$_{8-37}$ binding fragment including a stop codon; residues 151-156: restriction site for Xho I. Deduced amino acid sequences are aligned above the corresponding nucleotides.

```
        BoNT/D(-H_CC) - CGRP8-37 gene sequence and its encoded amino acids (SEQ ID NO: 17 AND 18)
            M  T  W  P  V  K  D  F  N  Y  S  D  P  V  N  D  N  D  I  L  Y  L  R  I  P  Q  N
          1 ATGACCTGGCCGGTGAAAGACTTTAACTATAGCGATCCGGTGAACGATAACGATATTCTGTATCTGCGTATCCCGCAGAA      80

K  L  I  T  T  P  V  K  A  F  M  I  T  Q  N  I  W  V  I  P  E  R  F  S  S  D
         81 CAAACTGATTACCACCCCGGTGAAAGCGTTCATGATTACCCAGAACATTTGGGTGATTCCGGAACGTTTTAGCAGCGATA     160

T  N  P  S  L  S  K  P  P  R  P  T  S  K  Y  Q  S  Y  Y  D  P  S  Y  L  S  T  D
        161 CCAATCCGAGCCTGAGCAAACCGCCGCGTCCGACCAGCAAATATCAGAGCTATTACGATCCGAGCTATCTGAGCACCGAT     240

E  Q  K  D  T  F  L  K  G  I  I  K  L  F  K  R  I  N  E  R  D  I  G  K  K  L  I
        241 GAACAGAAAGATACCTTCCTGAAAGGCATCATCAAACTGTTCAAACGCATTAACGAACGCGATATTGGCAAAAAACTGAT     320

N  Y  L  V  V  G  S  P  F  M  G  D  S  S  T  P  E  D  T  F  D  F  T  R  H  T
        321 CAACTATCTGGTGGTGGGCAGCCCGTTTATGGGCGATAGCAGCACCCCGGAAGATACCTTTGATTTTACCCGICATACCA     400

T  N  I  A  V  E  K  F  E  N  G  S  W  K  V  T  N  I  I  T  P  S  V  L  I  F  G
        401 CGAACATTGCGGTGGAAAAATTTGAAAACGGCAGCTGGAAAGTGACCAACATTATTACCCCGAGCGTGCTGATTTTTGGC     480

P  L  P  N  I  L  D  Y  T  A  S  L  T  L  Q  G  Q  Q  S  N  P  S  F  E  G  F  G
        481 CCGCTGCCGAACATTCTGGATTATACCGCGAGCCTGACGCTGCAAGGCCAGCAGAGCAATCCGAGCTTTGAAGGCTTTGG     560

T  L  S  I  L  K  V  A  P  E  F  L  L  T  F  S  D  V  T  S  N  Q  S  S  A  V
        561 CACCCTGAGCATTCTGAAAGTGGCGCCGGAATTTCTGCTGACCTTTAGCGATGTGACCAGCAACCAGAGCAGCGCGGTGC     640

L  G  K  S  I  F  C  M  D  P  V  I  A  L  M  H  E  L  T  H  S  L  H  Q  L  Y  G
        641 TGGGCAAAAGCATTTTTTGCATGGATCCGGTGATTGCGCTGATGCATGAACTGACCCATAGCCTGCATCAGCTGTATGGC     720

I  N  I  P  S  D  K  R  I  R  P  Q  V  S  E  G  F  F  S  Q  D  G  P  N  V  Q  F
        721 ATTAACATTCCGAGCGATAAACGTATTCGTCCGCAGGTGAGCGAAGGCTTTTTTAGCCAGGATGGCCCGAACGTGCAGTT     800

E  E  L  Y  T  F  G  G  L  D  V  E  I  I  P  Q  I  E  R  S  Q  L  R  E  K  A
```

| BoNT/D(⁻H_CC) - CGRP₈₋₃₇ gene sequence and its encoded amino acids (SEQ ID NO: 17 AND 18) |
|---|

```
801  TGAAGAACTGTATACCTTTGGCGGCCTGGATGTGGAAATTATTCCGCAGATTAACGTAGCCAGCTGCGTGAAAAAGCGC  880
      L  G  H  Y  K  D  I  A  K  R  L  N  N  I  N  K  T  I  P  S  S  W  I  S  N  I  D

881  TGGGCCACTATAAAGATATTGCGAAACGCCTGAACAACATCAACAAACCATTCCGAGCAGCTGGATTAGCAACATCGAT  960
       K  Y  K  K  I  F  S  E  K  Y  N  F  D  K  D  N  T  G  N  F  V  V  N  I  D  K  F

961  AAATACAAAAAAATCTTCAGCGAAAAATATAACTTCGATAAAGATAACACCGGCAACTTCGTGGTGAACATTGATAAATT  1040
       N  S  L  Y  S  D  L  T  N  V  M  S  E  V  V  Y  S  S  Q  Y  N  V  K  N  R  T

1041 CAACAGCCTGTATAGCGATCTGACCAACGTGATGAGCGAAGTGGTGTATAGCAGCCAGTATAACGTGAAAAACCGCACCC  1120
       H  Y  F  S  R  H  Y  L  P  V  F  A  N  I  L  D  D  N  I  Y  T  I  R  D  G  F  N

1121 ATTATTTCAGCCGTCATTATCTGCCGGTGTTTGCGAATATTCTGGATGATAACATCTATACCATCCGTGATGGCTTTAAC  1200
      L  T  N  K  G  F  N  I  E  N  S  G  Q  N  I  E  R  N  P  A  L  Q  K  L  S  S  E

1201 CTGACCAACAAAGGCTTTAACATTGAAAACAGCGGCCAGAACATTGAACGTAATCCGGCGCTGCAGAAACTGTCTAGCGA  1280
                                                                Thrombin cleavage site
                                                                         ↓
      S  V  V  D  L  F  T  K  V  C  L  R  L  T  L  V  P  R  G  S  T  C  I  K  V  K 1281 AAGCGTGGTGGACCTGTTTACCAAAGTGTGCCTGCGTCTGACCCTGGTGCCACGCGGTAGCACCTGCATCAAAGTGAAAA  1360
       N  N  R  L  P  Y  V  A  D  K  D  S  I  S  Q  E  I  F  E  N  K  I  I  T  D  E  T 1361 ACAACCGTCTGCCGTATGTGGCGGATAAAGATAGCATTAGCCAGGAAATCTTCGAAAACAAAATCATCACCGATGAAACC  1440
       N  V  Q  N  Y  S  D  K  F  S  L  D  E  S  I  L  D  G  Q  V  P  I  N  P  E  I  V 1441 AACGTGCAGAACTACAGCGATAAATTCAGCCTGGATGAAAGCATTCTGGATGGCCAGGTGCCGATTAATCCGGAAATTGT  1520
       D  P  L  L  P  N  V  N  M  E  P  L  N  L  P  G  E  E  I  V  F  Y  D  D  I  T 1521 GGATCCGCTGCTGCCGAACGTGAACATGGAACCGCTGAACCTGCCGGGCGAAGAAATTGTGTTCTATGATGATATTACCA  1600
       K  Y  V  D  Y  L  N  S  Y  Y  Y  L  E  S  Q  K  L  S  N  N  V  E  N  I  T  L  T 1601 AATATGTGGATTATCTGAACAGCTACTACTATCTGGAAAAGCCAGAAACTGAGCAACAACGTGGAAAACATTACCCTGACC  1680
       T  S  V  E  E  A  L  G  Y  S  N  K  I  Y  T  F  L  P  S  L  A  E  K  V  N  K  G 1681 ACCTCTGTGGAAGAAGCGCTGGGTTATAGCAACAAAATCTACACCTTTCTGCCGAGCCTGGCCGAAAAAGTGAACAAAGG  1760
       V  Q  A  G  L  F  L  N  W  A  N  E  V  V  E  D  F  T  T  N  I  M  K  K  D  T 1761 CGTGCAGGCGGGCCTGTTTCTGAACTGGGCGAACGAAGTGGTGGAAGATTTTACCACCAATATCATGAAAAAAGATACCC  1840
       L  D  K  I  S  D  V  S  V  I  I  P  Y  I  G  P  A  L  N  I  G  N  S  A  L  R  G 1841 TGGATAAAATCAGCGATGTGAGCGTGATTATTCCGTATATTGGTCCGGCGCTGAACATTGGCAACAGCGCCCTGCGTGGC  1920
       N  F  N  Q  A  F  A  T  A  G  V  A  F  L  L  E  G  F  P  E  F  T  I  P  A  L  G 1921 AACTTTAACCAGGCGTTTGCGACCGCGGGTGTGGCGTTTCTGCTGGAAGGCTTTCCGGAATTCACCATTCCGGCGCTGGG  2000
       V  F  T  F  Y  S  S  I  Q  E  R  E  K  I  I  K  T  I  E  N  C  L  E  Q  R  V 2001 CGTGTTTACCTTTTATAGCAGCATTCAGGAACGCGAAAAAATCATCAAAACCATCGAAAACTGCCTGGAACAGCGTGTGA  2080
       K  R  W  K  D  S  Y  Q  W  M  V  S  N  W  L  S  R  I  T  T  Q  F  N  H  I  N  Y 2081 AACGTTGGAAAGATAGCTATCAGTGGATGGTGAGCAACTGGCTGTCTCGTATTACCACCCAGTTTAACCACATCAACTAT  2160
       Q  M  Y  D  S  L  S  Y  Q  A  D  A  I  K  A  K  I  D  L  E  Y  K  K  Y  S  G  S 2161 CAGATGTATGACAGCCTGAGCTATCAGGCGGATGCGATTAAAGCGAAAATCGATCTGGAATACAAAAAATACAGCGGCAG  2240
       D  K  E  N  I  K  S  Q  V  E  N  L  K  N  S  L  D  V  K  I  S  E  A  M  N  N 2241 CGATAAAGAAAACATCAAAAGCCAGGTGGAAAACCTGAAAAACAGCCTGGATGTGAAAATTAGCGAAGCCATGAATAACA  2320
       I  N  K  F  I  R  E  C  S  V  T  Y  L  F  K  N  M  L  P  K  V  I  D  E  L  N  K
```

BoNT/D($^-$H$_{CC}$)- CGRP$_{8-37}$ gene sequence and its encoded amino acids (SEQ ID NO: 17 AND 18)

```
2321    TCAACAAATTCATCCGTGAATGCAGCGTGACCTACCTGTTTAAAAACATGCTGCCGAAAGTGATTGATGAACTGAACAAA                    2400
         F  D  L  R  T  K  T  E  L  I  N  L  I  D  S  H  N  I  I  L  V  G  E  V  D  R  L

2401    TTTGATCTGCGCACCAAAACCGAACTGATTAACCTGATCGATAGCCATAACATTATTCTGGTGGGCGAAGTGGATCGTCT                    2980
          K  A  K  V  N  E  S  F  E  N  T  M  P  F  N  I  F  S  Y  T  N  N  S  L  L  K

2481    GAAAGCGAAAGTGAACGAAAGCTTCGAAAACACCATGCCGTTTAACATCTTCAGCTACACCAACAACAGCCTGCTGAAAG                    2560
         D  I  I  N  E  Y  F  N  S  I  N  D  S  K  I  L  S  L  Q  N  K  K  N  A  L  V  D

2561    ATATTATCAACGAATATTTTAACAGCATCAACGATAGCAAAATTCTGAGCCTGCAGAACAAAAAAAACGCGCTGGTTGAT                    2640
          T  S  G  Y  N  A  E  V  R  V  G  D  N  V  Q  L  N  T  I  Y  T  N  D  F  K  L  S

2641    ACCAGCGGCTATAACGCGGAAGTGCGTGTGGGCGATAACGTGCAGCTGAACACCATTTATACCAACGATTTCAAACTGAG                    2720
           S  S  G  D  K  I  I  V  N  L  N  N  N  I  L  Y  S  A  I  Y  E  N  S  S  V  S

2721    CAGCAGCGGCGATAAAATTATTGTGAACCTGAATAACAACATTCTGTACAGCGCGATTTATGAAAACAGCAGCGTGAGCT                    2800
          F  W  I  K  I  S  K  D  L  T  N  S  H  N  E  Y  T  I  I  N  S  T  E  Q  N  S  G

2801    TTTGGATCAAAATCAGCAAAGATCTGACCAACAGCCATAACGAATACACCATCATCAACAGCATTGAACAGAACAGCGGC                    2880
           W  K  L  C  I  R  N  G  N  I  E  W  I  L  Q  D  V  N  R  K  Y  K  S  L  I  F  D

2881    TGGAAACTGTGCATTCGTAACGGCAACATTGAATGGATTCTGCAGGATGTGAACCGCAAATATAAAAGCCTGATCTTCGA                    2960
          Y  S  E  S  L  S  H  T  G  Y  T  N  K  W  F  F  V  T  I  T  N  N  I  M  G  Y

2961    TTATAGCGAAAGCCTGAGCCATACCGGCTATACCAACAAATGGTTCTTTGTGACCATCACCAACAACATTATGGGCTATA                    3040
          M  K  L  Y  I  N  G  E  L  K  Q  S  Q  K  I  E  D  L  D  E  V  K  L  D  K  T  I

3041    TGAAACTGTATATCAACGGCGAACTGAAACAGAGCCAGAAAATCGAAGATCTGGATGAAGTGAAACTGGATAAAACCATC                    3120
           V  F  G  I  D  E  N  I  D  E  N  Q  M  L  W  I  R  D  F  N  I  F  S  K  E  L  S

3121    GTGTTTGGCATCGATGAAAACATTGATGAAAACCAGATGCTGTGGATTCGCGATTTTAACATCTTTAGCAAAGAACTGAG                    3200
            N  E  D  I  N  I  V  Y  E  G  Q  I  E  L  G  G  G  G  S  G  G  G  G  S  G  G

3201    CAACGAAGATATTAACATCGTGTACGAAGGCCAGATTGATATCGGTGGTGGTGGTAGCGGTGGTGGCGGTTCAGGTGGTG                    3280
            G  G  S  V  T  H  R  L  A  G  L  L  S  R  S  G  G  V  V  K  N  N  F  V  P  T  N

3281    GTGGCAGCGTTACCCATCGTCTGGCTGGTCTGCTGTCTCGTAGCGGTGGTGTTGTGAAAAACAATTTTGTGCCGACAAAT                    3360
            V  G  S  K  A  F  *

3361    GTTGGTAGCAAAGCATTTTAA CTCGAG                                                                         3387
```

The synthetic nucleotide sequence provided above contains the following regions, respectively (identified with respect to the nucleotide residues—residues 1-3237 LC.H$_N$.H$_{CN}$/D; residues 3289-3381 (underlined and in bold), CGRP antagonist (CGRP$_{8-37}$). The DNA sequence comprising nucleotides 3238-3288) is introduced as a linker and ensures the proper reading frame. The aligned amino acid sequences are displayed above the corresponding nucleotides. A thrombin recognition sequence is engineered into the interchain loop region between LC/D and H$_N$/D; the arrow indicates this cleavage site.

It will be understood that each and every nucleotide sequence (including SEQ ID NOs. 13 and 17) encoding the amino acid sequence (including SEQ ID NOs. 14 and 18) is, and is intended to be, specifically and individually described as part of this patent application. It will also be understood by those of ordinary skill in the art that specific nucleic acid constructs described in Sequence ID No. 13 and 17 and their encoded respective amino acid sequences in Sequence ID No. 14 and 18 of this specification are exemplary, and that conservatively modified variations from these nucleotide and amino acid sequences may be made without departing from the scope of the invention disclosed herein. Thus, a nucleic acid construct having 95% or more, or 90% or more, or 85% or more, or 80% or more, or 75% or more, or 70% or more, or 60% or more homology to, for example and without limitation, SEQ ID Nos: 13 and 17 having the selective therapeutic activity indicated herein are intended to fall within the spirit of the present invention. Moreover, all nucleic acid constructs encoding the amino acid sequences disclosed in this specification are included within the scope of this invention.

Likewise, it will also be understood by those of ordinary skill in the art that amino acid sequences having 95% or more, or 90% or more, or 85% or more, or 80% or more, or 75% or more, or 70% or more, or 60% or more homology to Sequence ID No. 14 and 18 fall within the spirit of this embodiment of the invention.

It will also be understood that other analgesic bio-therapeutics with particularly valuable application to chronic pain may be generated using gene constructs similar to those described above, having one or more TL moiety encoding antibody-based single chain variable fragments (scFVs) or Fabs which bind membrane-exposed domains of antigens such as TRPV1 and/or $P2X_3$. Such constructs may have these TL moieties, either in place of the CGRP antagonist, PT-1 or IL-1RA TL moieties such as those described above, or may be inserted in addition to such a TL. All of the nucleic acids encoding such hybrid biotherapeutic proteins may be expressed in $E.\ coli$, mammalian or insect cells (or another suitable host cell/vector pair selected and utilized), and the resultant recombinant proteins purified by any suitable means, such as affinity and ion-exchange chromatography. Their specificities and potencies can then be evaluated in various models such as in cultured neurons, animal models of chronic neuropathic (e.g. spinal nerve injury) and inflammatory pain, and in in vitro systems, including, for example, the models and systems described herein.

EXAMPLE 4

Treatment of Chronic Pain Using a BoNT/D($^-H_{CC}$)-TL Clostridial Neurotoxin Derivative A 42-year-old woman presents complaining with chronic irritable bowel syndrome (IBS). Clinical examination reveals significant abdominal distention, and chronic frequent diarrhoea, accompanied by localized abdominal pain, scored by the patient as an 8 on a scale of 1 to 10.

The patient is injected directly in the intestinal sensory nerves with a therapeutic amount of the analgesic biotherapeutic BoNT/D($H_{CC}$)-TL, in which the TL is PT-1.

The patient is observed one week later, and examination reveals that the acute, chronic pain associated with IBS has been alleviated to a substantial amount, from a pain score of "8" to a pain score of "3" on a scale of 1 to 10.

The patient is again observed three weeks after the injection, and the analgesic activity of the biotherapeutic BoNT/D($^-H_{CC}$)-TL remains high, with the patient reporting a pain score of "4" after three weeks.

EXAMPLE 5

Treatment of Chronic Pain Associated with Esophageal Cancer Using a BoNT/C1($^-H_{CC}$)-(TRPV1 scFV) TL Clostridial Neurotoxin Derivative A 55 year-old man with a history of alcoholism presents with Stage 3 esophageal cancer, nausea, severe chronic pain in his throat radiating to the base of the skull, and the inability to take oral nourishment.

The patient is administered the Clostridial neurotoxin derivative BoNT/C1(-$H_{CC}$)-TRPV1 scFvs in an effective dose by injection directly into both the vagal nodose ganglion and the jugular ganglion. The gene construct is made similarly as reported above for construction of the BoNT/D($^-H_{CC}$)-$CGRP_{8-37}$ construct, and is expressed in $E.\ coli$. The Clostridial toxin derivative is affinity purified using the $His_6$ tag (SEQ ID NO: 19), and by ion exchange chromatography before use.

Within 48 hours, there is notable improvement in the extent and acuteness of pain, and within one week the patient is able to take oral nourishment. The patient is again observed three weeks after the injection, and the analgesic activity of the biotherapeutic BoNT/C1($^-$HCC)-(TRPV1 scFvs) remains high, with the patient reporting a pain score of "4" after three weeks.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

EXAMPLE 6

Treatment of Chronic Pain Associated with Rheumatoid Arthritis Using a BoNT/D$^-H_{CC}$-IL-1RA Clostridial Neurotoxin Derivative A 42 year-old woman presents with severe chronic joint pain in the left hip, and has difficulty walking. Following examination, the patient is diagnosed with rheumatoid arthritis of the acetabulofemoral (hip) joint.

The patient is administered the Clostridial neurotoxin derivative BoNT/D$^-H_{CC}$-IL-1RA in an effective dose by injection directly into both the femoral ganglion and the sciatic ganglion. The gene construct is made as described in Example 3 and expressed in $E.\ coli$. The Clostridial toxin derivative is affinity purified using the $His_6$ tag (SEQ ID NO: 19), and by ion exchange chromatography before use.

Within 48 hours, there is notable improvement in the extent and acuteness of pain, and within one week the patient is able to walk.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

Any and all patents, publications, patent applications, and nucleotide and/or amino acid sequences referred to by accession numbers cited in this specification are hereby incorporated by reference as part of this specification in its entirety. Each and every feature described herein, and each and every combination of two or more of such features, is included within the scope of the present invention provided that the features included in such a combination are not mutually inconsistent. These and other aspects of the present invention are set forth in the following claims.

The invention claimed is:

1. A composition comprising a Clostridial neurotoxin derivative, said composition comprising:
   a) a first active Clostridial toxin-derived endopeptidase domain which cleaves a SNARE protein under physiological conditions;
   b) a Clostridial toxin-derived translocation domain which facilitates the movement of said first and second endopeptidase domains across a cellular membrane into the cytosol under physiological conditions;
   c) a non-Clostridial toxin derived binding domain comprising a first targeting ligand (TL) selectively binding, under physiological conditions, to a first cell surface receptor displayed by a target cell, said target cell selected from the group consisting of:
      i) a sensory neuron, and
      ii) a cell that secretes at least one inflammatory
      iii) cytokine,
      said cell surface receptor being substantially absent from motor or autonomic neurons; and
   d) a Clostridial toxin-derived functional $H_{CN}$ domain;
   wherein said light chain protease of said Clostridial neurotoxin derivative is internalized by said target cell upon binding of said TL to the target cell, and wherein an $H_{cc}$ targeting domain is either absent or mutated to impede binding of the HCC domain to its natural protein receptor.

2. The composition of claim 1 wherein the neurotoxin derivative lacks a Clostridial neurotoxin-derived $H_{CC}$ targeting domain.

3. The composition of claim 1 wherein the neurotoxin derivative contains a Clostridial neurotoxin-derived $H_{CC}$ domain mutated to impede binding of the $H_{CC}$ domain to its natural protein receptor.

4. The composition of claim 3 wherein said mutated $H_{CC}$ domain comprises a glutamic acid residue at a position corresponding to amino acid 1192 of BoNT/B.

5. The composition of claim 3 wherein said mutated $H_{CC}$ domain comprises a lysine residue at a position corresponding to amino acid 1196 of BoNT/B.

6. The composition of claim 5 wherein said mutated $H_{CC}$ domain also comprises a glutamic acid residue at a position corresponding to amino acid 1192 of BoNT/B.

7. The composition of claim 3 wherein said mutated $H_{CC}$ domain is derived from BoNT/B.

8. The composition of claim 4 wherein said mutated $H_{CC}$ domain is derived from BoNT/B.

9. The composition of claim 5 wherein said mutated $H_{CC}$ domain is derived from BoNT/B.

10. The composition of claim 6 wherein said mutated Hcc domain is derived from BoNT/B.

11. The composition of claim 1 wherein said neurotoxin derivative comprises a second Clostridial toxin-derived endopeptidase domain containing a mutation rendering it substantially proteolytically inactive.

12. The composition of claim 1 wherein said neurotoxin derivative comprises a second, different, Clostridial toxin-derived endopeptidase domain.

13. The composition of claim 12 wherein the second Clostridial toxin-derived endopeptidase domain is derived from BoNT/A.

14. The composition of claim 1 wherein the first Clostridial toxin-derived endopeptidase domain comprises a endopeptidase derived from BoNT/E.

15. The composition of claim 1 wherein the Clostridial toxin-derived translocation domain is derived from a BoNT/X subtype selected from the group consisting of BoNT/A, BoNT/C1, BoNT/D, BoNT/G and BoNT/E.

16. The composition of claim 12 wherein the Clostridial toxin-derived translocation domain is derived from a BoNT/X subtype selected from the group consisting of BoNt/A, BoNT/C1, BoNT/D, BoNT/G and BoNT/E.

17. The composition of claim 1 wherein the TL comprises a targeting component selected from the group consisting of a CGRP receptor antagonist, a CGRP receptor-selective or CGRP receptor-specific antibody or selective fragment thereof, a TRPV1 antagonist, a TRPV1-selective or TRPV1-specific antibody or fragment thereof, an interleukin 1 agonist or an interleukin 1 receptor antagonist, an IL-1 receptor selective or IL-1 receptor specific antibody or fragment thereof, a P2X3 antagonist, or a P2X3-selective or P2X3-specific antibody or fragment thereof.

18. The composition of claim 11 wherein the TL comprises a targeting component selected from the group consisting of a CGRP receptor antagonist, a CGRP receptor-selective or CGRP receptor-specific antibody or selective fragment thereof, a TRPVI antagonist, a TRPVI-selective or TRPV1-specific antibody or fragment thereof, an interleukin 1 agonist or an interleukin 1 receptor antagonist, an IL-1 receptor selective or IL-1 receptor specific antibody or fragment thereof, a P2X3 antagonist, or a P2X3-selective or P2X3-specific antibody or fragment thereof.

19. The composition of claim 1 comprising a polypeptide comprising an active Clostridial toxin-derived endopeptidase domain derived from BoNT/E, a Clostridial toxin-derived translocation domain derived from BoNT/A, and a TL domain.

20. The composition of claim 12 wherein the TL comprises a targeting component comprising a CGRP receptor antagonist.

21. The neurotoxin derivative of claim 1 in which said Clostridial toxin-derived endopeptidase domain comprises an endopeptidase having an enzymatic half-life of 10 days or greater when injected into mouse gastrocnemius muscle under substantially physiological conditions.

22. The neurotoxin derivative of claim 12 in which said first or second Clostridial toxin-derived endopeptidase domain comprises an endopeptidase having an enzymatic half-life of 10 days or greater when injected into mouse gastrocnemius muscle under substantially physiological conditions.

23. The neurotoxin derivative of claim 1 comprising a BoNT/D light chain, a BoNT/D translocation domain, and a targeting ligand comprising $CGRP_{8-37}$, and lacking a functional $H_{CC}$ domain.

24. The neurotoxin derivative of claim 23 wherein the neurotoxin derivative contains a Clostridial neurotoxin-derived $H_{CC}$ domain mutated to impede binding of the $H_{CC}$ domain to its natural protein receptor.

25. The neurotoxin derivative of claim 23 comprising BoNT/D ($^-H_{CC}$)-$CGRP_{8-37}$.

26. The neurotoxin derivative of claim 1 comprising a BoNT/D light chain, a BoNT/D translocation domain, and a targeting ligand comprising human IL-1RA, and lacking a functional $H_{CC}$ domain.

27. The neurotoxin derivative of claim 26 wherein the neurotoxin derivative contains a Clostridial neurotoxin-derived $H_{CC}$ domain mutated to impede binding of the $H_{cc}$ domain to its natural protein receptor.

28. The neurotoxin derivative of claim 26 comprising BoNT/D ($^-H_{CC}$)-human IL-1RA.

29. The neurotoxin derivative of claim 1 comprising a BoNT/A light chain, a BoNT/A translocation domain, and a targeting ligand comprising a purinergic receptor ligand, and lacking a functional $H_{CC}$ domain.

30. The neurotoxin derivative of claim 29 wherein the targeting ligand is a P2X3 receptor ligand.

31. The neurotoxin derivative of claim 30 wherein the targeting ligand comprises a purotoxin 1 or a selectively binding fragment thereof.

32. The neurotoxin derivative of claim 31 comprising $LC.H_N.H_{CN}$/A-PT-1.

33. The neurotoxin derivative of claim 1 in which the TL specifically binds, under physiological conditions, to a first cell surface receptor displayed by a sensory neuron in preference to motor or autonomic neurons.

34. The neurotoxin derivative of claim 33 comprising at least two TL domains.

35. The neurotoxin derivative of claim 1 wherein the Clostridial neurotoxin translocation domain is selected from the group consisting of a) a BoNT-A translocation domain;
b) a BoNT-B translocation domain;
c) a BoNT-C1 translocation domain;
d) a BoNT-D translocation domain;
e) a BoNT-E translocation domain;
f) a BoNT-F translocation domain;
g) a BoNT-G translocation domain, and
h) conservatively modified variants and isoforms of any of the above.

36. An analgesic Clostridial neurotoxin derivative comprising:
a) A first active Clostridial toxin-derived endopeptidase domain which cleaves a SNARE protein under physiological conditions and having an enzymatic half-life of 10 days or greater when injected into mouse gastrocnemius muscle under substantially physiological conditions;
b) a Clostridial toxin-derived translocation domain which facilitates the movement of said first endopeptidase domain across a cellular membrane into the cytosol under physiological conditions;
c) a binding domain comprising a first targeting ligand (TL) selectively binding, under physiological conditions, to a first cell surface receptor displayed by a target cell, said target cell selected from the group consisting of:
i) sensory neurons, and
ii) cytokine secreting cells
in preference to a non-target cell type selected from the group consisting of motor neurons and autonomic neurons; and
d) a Clostridial toxin-derived functional $H_{CN}$ domain;
wherein said neurotoxin derivative lacks a functional Clostridial toxin $H_{CC}$ domain and wherein a target cell internalizes the endopeptidase domain of said Clostridial neurotoxin derivative upon binding of said TL to the target cell.

37. The neurotoxin derivative of claim 36 wherein the neurotoxin derivative contains a Clostridial neurotoxin-derived $H_{CC}$ domain mutated to impede binding of the $H_{CC}$ domain to its natural protein receptor.

38. The neurotoxin derivative of claim 37 comprising an active $H_{CN}$ domain.

39. The neurotoxin derivative of claim 38 wherein said first active Clostridial toxin-derived endopeptidase domain is derived from a toxin serotype selected from the group consisting of BoNT/A, BoNT/E, BoNT/C1, BoNT/G and BoNT/D.

40. The neurotoxin derivative of claim 38 wherein the Clostridial neurotoxin translocation domain is selected from the group consisting of
a) a BoNT-A translocation domain;
b) a BoNT-B translocation domain;
c) a BoNT-C1 translocation domain;
d) a BoNT-D translocation domain;
e) a BoNT-E translocation domain;
f) a BoNT-F translocation domain;
g) a BoNT-G translocation domain, and
h) conservatively modified variants and isoforms of any of the above.

41. The neurotoxin derivative of claim 38 in which the translocation domain and the first active endopeptidase domain are both derived from the same BoNT serotype.

42. The neurotoxin derivative of claim 36 comprising a second Clostridial toxin-derived endopeptidase domain.

43. The neurotoxin derivative of claim 42 in which the second Clostridial toxin-derived endopeptidase domain lacks endopeptidase protease activity effective to substantially cleave a population of SNARE proteins under physiological conditions.

44. The neurotoxin derivative of claim 36 in which the TL comprises a targeting component selected from the group consisting of a CGRP receptor antagonist, a CGRP receptor-selective or CGRP receptor-specific antibody or selective fragment thereof, a TRPV1 antagonist, a TRPV1-selective or TRPV1-specific antibody or fragment thereof, an interleukin 1 agonist or an interleukin 1 receptor antagonist, an IL-1 receptor selective or IL-1 receptor specific antibody or fragment thereof, a P2X3 -selective or P2X3-specific antibody or fragment thereof, and conservatively modified variants and isoforms of any of the above.

45. The neurotoxin derivative of claim 36 comprising at least two TL domains.

46. The neurotoxin derivative of claim 36 in which said first endopeptidase domain and said translocation domain are both derived from BoNT/D.

47. The neurotoxin derivative of claim 36 in which said first endopeptidase domain and said translocation domain are both derived from BoNT/A.

48. The neurotoxin derivative of claim 46 in which the TL comprises a targeting component selected from the group consisting of a CGRP receptor antagonist, a CGRP receptor-selective or CGRP receptor-specific antibody or selective fragment thereof, a TRPV1 antagonist, a TRPV1-selective or TRPV1-specific antibody or fragment thereof, an interleukin 1 agonist or an interleukin 1 receptor antagonist, an IL-1 receptor selective or IL-1 specific antibody or fragment thereof, a P2X3 antagonist, or a P2X3-selective or P2X3-specific antibody or fragment thereof, and conservatively modified variants and isoforms of any of the above.

49. The neurotoxin derivative of claim 47 in which the TL comprises a targeting component selected from the group consisting of a CGRP receptor antagonist, a CGRP receptor-selective or CGRP receptor-specific antibody or selective fragment thereof, a TRPV1 antagonist, a TRPV1-selective or TRPV1-specific antibody or fragment thereof, an interleukin 1 agonist or an interleukin 1 receptor antagonist, an IL-1 receptor selective or IL-1 specific antibody or fragment thereof, a P2X3 antagonist, or a P2X3-selective or P2X3-specific antibody or fragment thereof, and conservatively modified variants and isoforms of any of the above.

50. The neurotoxin derivative of claim 36 in which said first endopeptidase domain and said translocation domain are both derived from BoNT/C1.

51. The neurotoxin derivative of claim 50 in which the TL comprises a targeting component selected from the group consisting of a CGRP receptor antagonist, a CGRP receptor-selective or CGRP receptor-specific antibody or selective fragment thereof, a TRPV1 antagonist, a TRPV1-selective or TRPV1-specific antibody or fragment thereof, an interleukin 1 agonist or an interleukin 1 receptor antagonist, an IL-1 receptor selective or IL-1 specific antibody or fragment thereof, a P2X3 antagonist, or a P2X3-selective or P2X3-specific antibody or fragment thereof, and conservatively modified variants and isoforms of any of the above.

52. The composition of claim 1 wherein said neurotoxin derivative comprises a second active Clostrial neurotoxin-derived endopeptidase domain.

53. The neurotoxin derivative of claim 1 wherein said target cell is a cell that secretes at least one inflammatory cytokine, wherein said cell is selected from the group consisting of a macrophage, a monocyte, a synoviocyte, a mast cells and a neutrophil.

54. The neurotoxin derivative of claim 3 wherein said $H_{CC}$ targeting domain is mutated to comprise one or both of: a glutamic acid residue at a position corresponding to amino acid 1192 of BoNT/B, and a lysine residue at a position corresponding to amino acid 1196 of BoNT/B.

55. The composition of claim 36 wherein said neurotoxin derivative comprises a second active Clostrial neurotoxin-derived endopeptidase domain.

56. The neurotoxin derivative of claim 36 wherein said target cell is a cell that secretes at least one inflammatory cytokine, wherein said cell is selected from the group consisting of a macrophage, a monocyte, a synoviocyte, a mast cells and a neutrophil.

57. The neurotoxin derivative of claim 37 wherein said $H_{CC}$ targeting domain is mutated to comprise one or both of: a glutamic acid residue at a position corresponding to amino acid 1192 of BoNT/B, and a lysine residue at a position corresponding to amino acid 1196 of BoNT/B.

58. An analgesic formulation comprising the composition of claim 1 for the treatment of chronic pain selected from the group consisting of cancer pain, post-operative pain, neuropathic pain, allodynia, post-herpetic neuralgia, irritable bowel syndrome, and other visceral pain, arthritis pain, bone pain, peripheral neuropathy, circulatory system-affiliated pain, and headache pain.

59. An analgesic formulation comprising the composition of claim 36 for the treatment of chronic pain selected from the group consisting of cancer pain, post-operative pain, neuropathic pain, allodynia, post-herpetic neuralgia, irritable bowel syndrome, and other visceral pain, arthritis pain, bone pain, peripheral neuropathy, circulatory system-affiliated pain, and headache pain.

* * * * *

SEQUENCE LISTING

<160> NUMBER OF SEQ ID NOS: 21

<210> SEQ ID NO 1
<211> LENGTH: 1296
<212> TYPE: PRT
<213> ORGANISM: Clostridium botulinum

```
<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65              70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
```

-continued

```
                405                 410                 415
Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
                530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Met Phe Leu Gly Trp Val Glu
                595                 600                 605

Gln Leu Val Tyr Asp Phe Thr Asp Glu Thr Ser Glu Val Ser Thr Thr
                610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
                690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
                770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830
```

-continued

```
Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Asn Ala Ile Val Tyr Asn Ser Met Tyr Glu Asn Phe Ser Thr Ser
        930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
        980                 985                 990

Ile Lys Gln Arg Val Val Phe Lys  Tyr Ser Gln Met Ile  Asn Ile Ser
        995                 1000                1005

Asp Tyr  Ile Asn Arg Trp Ile  Phe Val Thr Ile  Thr Asn Asn Arg
    1010                1015                1020

Leu Asn  Asn Ser Lys Ile Tyr  Ile Asn Gly Arg Leu  Ile Asp Gln
    1025                1030                1035

Lys Pro  Ile Ser Asn Leu Gly  Asn Ile His Ala Ser  Asn Asn Ile
    1040                1045                1050

Met Phe  Lys Leu Asp Gly Cys  Arg Asp Thr His Arg  Tyr Ile Trp
    1055                1060                1065

Ile Lys  Tyr Phe Asn Leu Phe  Asp Lys Glu Leu Asn  Glu Lys Glu
    1070                1075                1080

Ile Lys  Asp Leu Tyr Asp Asn  Gln Ser Asn Ser Gly  Ile Leu Lys
    1085                1090                1095

Asp Phe  Trp Gly Asp Tyr Leu  Gln Tyr Asp Lys Pro  Tyr Tyr Met
    1100                1105                1110

Leu Asn  Leu Tyr Asp Pro Asn  Lys Tyr Val Asp Val  Asn Asn Val
    1115                1120                1125

Gly Ile  Arg Gly Tyr Met Tyr  Leu Lys Gly Pro Arg  Gly Ser Val
    1130                1135                1140

Met Thr  Thr Asn Ile Tyr Leu  Asn Ser Ser Leu Tyr  Arg Gly Thr
    1145                1150                1155

Lys Phe  Ile Ile Lys Lys Tyr  Ala Ser Gly Asn Lys  Asp Asn Ile
    1160                1165                1170

Val Arg  Asn Asn Asp Arg Val  Tyr Ile Asn Val Val  Val Lys Asn
    1175                1180                1185

Lys Glu  Tyr Arg Leu Ala Thr  Asn Ala Ser Gln Ala  Gly Val Glu
    1190                1195                1200

Lys Ile  Leu Ser Ala Leu Glu  Ile Pro Asp Val Gly  Asn Leu Ser
    1205                1210                1215

Gln Val  Val Val Met Lys Ser  Lys Asn Asp Gln Gly  Ile Thr Asn
    1220                1225                1230
```

-continued

```
Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 2
<211> LENGTH: 1291
<212> TYPE: PRT
<213> ORGANISM: Clostridium botulinum

<400> SEQUENCE: 2

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300
```

-continued

```
Lys Val Leu Val Cys Ile Ser Asp Pro Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720
```

-continued

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
                835                 840                 845

Leu Ile Glu Met Phe Asn Lys Tyr Asn Ser Glu Ile Leu Asn Asn Ile
                850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
                900                 905                 910

Gln Asn Gln Asn Ile Ile Phe Asn Ser Val Phe Leu Asp Phe Ser Val
                915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
            995                 1000                1005

Asn Asn Leu Asn Asn Ala Lys Ile Tyr Ile Asn Gly Lys Leu Glu
            1010                1015                1020

Ser Asn Thr Asp Ile Lys Asp Ile Arg Glu Val Ile Ala Asn Gly
            1025                1030                1035

Glu Ile Ile Phe Lys Leu Asp Gly Asp Ile Asp Arg Thr Gln Phe
            1040                1045                1050

Ile Trp Met Lys Tyr Phe Ser Ile Phe Asn Thr Glu Leu Ser Gln
            1055                1060                1065

Ser Asn Ile Glu Glu Arg Tyr Lys Ile Gln Ser Tyr Ser Glu Tyr
            1070                1075                1080

Leu Lys Asp Phe Trp Gly Asn Pro Leu Met Tyr Asn Lys Glu Tyr
            1085                1090                1095

Tyr Met Phe Asn Ala Gly Asn Lys Asn Ser Tyr Ile Lys Leu Lys
            1100                1105                1110

Lys Asp Ser Pro Val Gly Glu Ile Leu Thr Arg Ser Lys Tyr Asn
            1115                1120                1125

Gln Asn Ser Lys Tyr Ile Asn Tyr Arg Asp Leu Tyr Ile Gly Glu

```
            1130                1135                1140
Lys Phe Ile Ile Arg Arg Lys Ser Asn Ser Gln Ser Ile Asn Asp
            1145                1150                1155

Asp Ile Val Arg Lys Glu Asp Tyr Ile Tyr Leu Asp Phe Phe Asn
            1160                1165                1170

Leu Asn Gln Glu Trp Arg Val Tyr Thr Tyr Lys Tyr Phe Lys Lys
            1175                1180                1185

Glu Glu Glu Lys Leu Phe Leu Ala Pro Ile Ser Asp Ser Asp Glu
            1190                1195                1200

Phe Tyr Asn Thr Ile Gln Ile Lys Glu Tyr Asp Glu Gln Pro Thr
            1205                1210                1215

Tyr Ser Cys Gln Leu Leu Phe Lys Lys Asp Glu Glu Ser Thr Asp
            1220                1225                1230

Glu Ile Gly Leu Ile Gly Ile His Arg Phe Tyr Glu Ser Gly Ile
            1235                1240                1245

Val Phe Glu Glu Tyr Lys Asp Tyr Phe Cys Ile Ser Lys Trp Tyr
            1250                1255                1260

Leu Lys Glu Val Lys Arg Lys Pro Tyr Asn Leu Lys Leu Gly Cys
            1265                1270                1275

Asn Trp Gln Phe Ile Pro Lys Asp Glu Gly Trp Thr Glu
            1280                1285                1290

<210> SEQ ID NO 3
<211> LENGTH: 1291
<212> TYPE: PRT
<213> ORGANISM: Clostridium botulinum

<400> SEQUENCE: 3

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205
```

```
Val Gly Glu Gly Arg Phe Ser Lys Ser Glu Phe Cys Met Asp Pro Ile
210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
            245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
            435                 440                 445

Lys Thr Leu Asp Cys Arg Glu Leu Leu Val Lys Asn Thr Asp Leu Pro
450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
            515                 520                 525

Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
```

-continued

```
            625                 630                 635                 640
Ser Val Arg Arg Gly Asn Phe Thr Glu Ala Phe Ala Val Thr Gly Val
                    645                 650                 655

Thr Ile Leu Leu Glu Ala Phe Pro Glu Phe Thr Ile Pro Ala Leu Gly
                660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
            690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                    725                 730                 735

Ala Ile Lys Ala Lys Ile Asp Leu Glu Tyr Lys Lys Tyr Ser Gly Ser
                740                 745                 750

Asp Lys Glu Asn Ile Lys Ser Gln Val Glu Asn Leu Lys Asn Ser Leu
            755                 760                 765

Asp Val Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                    805                 810                 815

Leu Ile Asp Ser His Asn Ile Ile Leu Val Gly Glu Val Asp Lys Leu
                820                 825                 830

Lys Ala Lys Val Asn Asn Ser Phe Gln Asn Thr Ile Pro Phe Asn Ile
            835                 840                 845

Phe Ser Tyr Thr Asn Asn Ser Leu Leu Lys Asp Ile Ile Asn Glu Tyr
            850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                    885                 890                 895

Gly Asp Val Gln Leu Asn Pro Ile Phe Pro Phe Asp Phe Lys Leu Gly
                900                 905                 910

Ser Ser Gly Glu Asp Arg Gly Lys Val Ile Val Thr Gln Asn Glu Asn
            915                 920                 925

Ile Val Tyr Asn Ser Met Tyr Glu Ser Phe Ser Ile Ser Phe Trp Ile
            930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                    965                 970                 975

Leu Val Phe Thr Leu Lys Gln Asn Glu Asp Ser Glu Gln Ser Ile Asn
                980                 985                 990

Phe Ser Tyr Asp Ile Ser Asn Asn Ala Pro Gly Tyr Asn Lys Trp Phe
            995                 1000                1005

Phe Val Thr Val Thr Asn Asn Met Met Gly Asn Met Lys Ile Tyr
            1010                1015                1020

Ile Asn Gly Lys Leu Ile Asp Thr Ile Lys Val Lys Glu Leu Thr
            1025                1030                1035

Gly Ile Asn Phe Ser Lys Thr Ile Thr Phe Glu Ile Asn Lys Ile
            1040                1045                1050
```

```
Pro Asp Thr Gly Leu Ile Thr Ser Asp Ser Asp Asn Ile Asn Met
    1055                1060                1065

Trp Ile Arg Asp Phe Tyr Ile Phe Ala Lys Glu Leu Asp Gly Lys
    1070                1075                1080

Asp Ile Asn Ile Leu Phe Asn Ser Leu Gln Tyr Thr Asn Val Val
    1085                1090                1095

Lys Asp Tyr Trp Gly Asn Asp Leu Arg Tyr Asn Lys Glu Tyr Tyr
    1100                1105                1110

Met Val Asn Ile Asp Tyr Leu Asn Arg Tyr Met Tyr Ala Asn Ser
    1115                1120                1125

Arg Gln Ile Val Phe Asn Thr Arg Arg Asn Asn Asn Asp Phe Asn
    1130                1135                1140

Glu Gly Tyr Lys Ile Ile Ile Lys Arg Ile Arg Gly Asn Thr Asn
    1145                1150                1155

Asp Thr Arg Val Arg Gly Gly Asp Ile Leu Tyr Phe Asp Met Thr
    1160                1165                1170

Ile Asn Asn Lys Ala Tyr Asn Leu Phe Met Lys Asn Glu Thr Met
    1175                1180                1185

Tyr Ala Asp Asn His Ser Thr Glu Asp Ile Tyr Ala Ile Gly Leu
    1190                1195                1200

Arg Glu Gln Thr Lys Asp Ile Asn Asp Asn Ile Ile Phe Gln Ile
    1205                1210                1215

Gln Pro Met Asn Asn Thr Tyr Tyr Tyr Ala Ser Gln Ile Phe Lys
    1220                1225                1230

Ser Asn Phe Asn Gly Glu Asn Ile Ser Gly Ile Cys Ser Ile Gly
    1235                1240                1245

Thr Tyr Arg Phe Arg Leu Gly Gly Asp Trp Tyr Arg His Asn Tyr
    1250                1255                1260

Leu Val Pro Thr Val Lys Gln Gly Asn Tyr Ala Ser Leu Leu Glu
    1265                1270                1275

Ser Thr Ser Thr His Trp Gly Phe Val Pro Val Ser Glu
    1280                1285                1290

<210> SEQ ID NO 4
<211> LENGTH: 1276
<212> TYPE: PRT
<213> ORGANISM: Clostridium botulinum

<400> SEQUENCE: 4

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
```

-continued

```
                115                 120                 125
Phe Thr Arg His Thr Thr Asn Ile Ala Val Glu Lys Phe Glu Asn Gly
130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
        515                 520                 525

Phe Tyr Asp Asp Ile Thr Lys Tyr Val Asp Tyr Leu Asn Ser Tyr Tyr
    530                 535                 540
```

-continued

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
            565                 570                 575

Phe Leu Pro Ser Leu Ala Glu Lys Val Asn Lys Gly Val Gln Ala Gly
        580                 585                 590

Leu Phe Leu Asn Trp Ala Asn Glu Val Val Glu Asp Phe Thr Thr Asn
    595                 600                 605

Ile Met Lys Lys Asp Thr Leu Asp Lys Ile Ser Asp Val Ser Val Ile
610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
            645                 650                 655

Glu Gly Phe Pro Glu Phe Thr Ile Pro Ala Leu Gly Val Phe Thr Phe
        660                 665                 670

Tyr Ser Ser Ile Gln Glu Arg Glu Lys Ile Ile Lys Thr Ile Glu Asn
    675                 680                 685

Cys Leu Glu Gln Arg Val Lys Arg Trp Lys Asp Ser Tyr Gln Trp Met
690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
            725                 730                 735

Lys Ile Asp Leu Glu Tyr Lys Lys Tyr Ser Gly Ser Asp Lys Glu Asn
        740                 745                 750

Ile Lys Ser Gln Val Glu Asn Leu Lys Asn Ser Leu Asp Val Lys Ile
    755                 760                 765

Ser Glu Ala Met Asn Asn Ile Asn Lys Phe Ile Arg Glu Cys Ser Val
770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
            805                 810                 815

His Asn Ile Ile Leu Val Gly Glu Val Asp Arg Leu Lys Ala Lys Val
        820                 825                 830

Asn Glu Ser Phe Glu Asn Thr Met Pro Phe Asn Ile Phe Ser Tyr Thr
    835                 840                 845

Asn Asn Ser Leu Leu Lys Asp Ile Ile Asn Glu Tyr Phe Asn Ser Ile
850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
            885                 890                 895

Leu Asn Thr Ile Tyr Thr Asn Asp Phe Lys Leu Ser Ser Ser Gly Asp
        900                 905                 910

Lys Ile Ile Val Asn Leu Asn Asn Asn Ile Leu Tyr Ser Ala Ile Tyr
    915                 920                 925

Glu Asn Ser Ser Val Ser Phe Trp Ile Lys Ile Ser Lys Asp Leu Thr
930                 935                 940

Asn Ser His Asn Glu Tyr Thr Ile Ile Asn Ser Ile Glu Gln Asn Ser
945                 950                 955                 960

```
Gly Trp Lys Leu Cys Ile Arg Asn Gly Asn Ile Glu Trp Ile Leu Gln
                965                 970                 975
Asp Val Asn Arg Lys Tyr Lys Ser Leu Ile Phe Asp Tyr Ser Glu Ser
            980                 985                 990
Leu Ser His Thr Gly Tyr Thr Asn Lys Trp Phe Phe Val Thr Ile Thr
        995                 1000                1005
Asn Asn Ile Met Gly Tyr Met Lys Leu Tyr Ile Asn Gly Glu Leu
    1010                1015                1020
Lys Gln Ser Gln Lys Ile Glu Asp Leu Asp Glu Val Lys Leu Asp
    1025                1030                1035
Lys Thr Ile Val Phe Gly Ile Asp Glu Asn Ile Asp Glu Asn Gln
    1040                1045                1050
Met Leu Trp Ile Arg Asp Phe Asn Ile Phe Ser Lys Glu Leu Ser
    1055                1060                1065
Asn Glu Asp Ile Asn Ile Val Tyr Glu Gly Gln Ile Leu Arg Asn
    1070                1075                1080
Val Ile Lys Asp Tyr Trp Gly Asn Pro Leu Lys Phe Asp Thr Glu
    1085                1090                1095
Tyr Tyr Ile Ile Asn Asp Asn Tyr Ile Asp Arg Tyr Ile Ala Pro
    1100                1105                1110
Glu Ser Asn Val Leu Val Leu Val Gln Tyr Pro Asp Arg Ser Lys
    1115                1120                1125
Leu Tyr Thr Gly Asn Pro Ile Thr Ile Lys Ser Val Ser Asp Lys
    1130                1135                1140
Asn Pro Tyr Ser Arg Ile Leu Asn Gly Asp Asn Ile Ile Leu His
    1145                1150                1155
Met Leu Tyr Asn Ser Arg Lys Tyr Met Ile Ile Arg Asp Thr Asp
    1160                1165                1170
Thr Ile Tyr Ala Thr Gln Gly Gly Glu Cys Ser Gln Asn Cys Val
    1175                1180                1185
Tyr Ala Leu Lys Leu Gln Ser Asn Leu Gly Asn Tyr Gly Ile Gly
    1190                1195                1200
Ile Phe Ser Ile Lys Asn Ile Val Ser Lys Asn Lys Tyr Cys Ser
    1205                1210                1215
Gln Ile Phe Ser Ser Phe Arg Glu Asn Thr Met Leu Leu Ala Asp
    1220                1225                1230
Ile Tyr Lys Pro Trp Arg Phe Ser Phe Lys Asn Ala Tyr Thr Pro
    1235                1240                1245
Val Ala Val Thr Asn Tyr Glu Thr Lys Leu Leu Ser Thr Ser Ser
    1250                1255                1260
Phe Trp Lys Phe Ile Ser Arg Asp Pro Gly Trp Val Glu
    1265                1270                1275

<210> SEQ ID NO 5
<211> LENGTH: 1252
<212> TYPE: PRT
<213> ORGANISM: Clostridium botulinum

<400> SEQUENCE: 5

Met Pro Lys Ile Asn Ser Phe Asn Tyr Asn Asp Pro Val Asn Asp Arg
1               5                   10                  15
Thr Ile Leu Tyr Ile Lys Pro Gly Gly Cys Gln Glu Phe Tyr Lys Ser
            20                  25                  30
Phe Asn Ile Met Lys Asn Ile Trp Ile Ile Pro Glu Arg Asn Val Ile
        35                  40                  45
```

```
Gly Thr Thr Pro Gln Asp Phe His Pro Pro Thr Ser Leu Lys Asn Gly
 50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                 85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
450                 455                 460
```

```
Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
            530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
            565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
            595                 600                 605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
            725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
770                 775                 780

Tyr Asp Glu Asn Val Lys Thr Tyr Leu Leu Asn Tyr Ile Ile Gln His
            785                 790                 795                 800

Gly Ser Ile Leu Gly Glu Ser Gln Gln Glu Leu Asn Ser Met Val Thr
            805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
            850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
```

```
                885                 890                 895
Glu Val Asn Ile Ser Gln Asn Asp Tyr Ile Ile Tyr Asp Asn Lys Tyr
                900                 905                 910
Lys Asn Phe Ser Ile Ser Phe Trp Val Arg Ile Pro Asn Tyr Asp Asn
                915                 920                 925
Lys Ile Val Asn Val Asn Asn Glu Tyr Thr Ile Ile Asn Cys Met Arg
                930                 935                 940
Asp Asn Asn Ser Gly Trp Lys Val Ser Leu Asn His Asn Glu Ile Ile
945                 950                 955                 960
Trp Thr Leu Gln Asp Asn Ala Gly Ile Asn Gln Lys Leu Ala Phe Asn
                965                 970                 975
Tyr Gly Asn Ala Asn Gly Ile Ser Asp Tyr Ile Asn Lys Trp Ile Phe
                980                 985                 990
Val Thr Ile Thr Asn Asp Arg Leu Gly Asp Ser Lys Leu Tyr Ile Asn
                995                1000                1005
Gly Asn Leu Ile Asp Gln Lys Ser Ile Leu Asn Leu Gly Asn Ile
                1010                1015                1020
His Val Ser Asp Asn Ile Leu Phe Lys Ile Val Asn Cys Ser Tyr
                1025                1030                1035
Thr Arg Tyr Ile Gly Ile Arg Tyr Phe Asn Ile Phe Asp Lys Glu
                1040                1045                1050
Leu Asp Glu Thr Glu Ile Gln Thr Leu Tyr Ser Asn Glu Pro Asn
                1055                1060                1065
Thr Asn Ile Leu Lys Asp Phe Trp Gly Asn Tyr Leu Leu Tyr Asp
                1070                1075                1080
Lys Glu Tyr Tyr Leu Leu Asn Val Leu Lys Pro Asn Asn Phe Ile
                1085                1090                1095
Asp Arg Arg Lys Asp Ser Thr Leu Ser Ile Asn Asn Ile Arg Ser
                1100                1105                1110
Thr Ile Leu Leu Ala Asn Arg Leu Tyr Ser Gly Ile Lys Val Lys
                1115                1120                1125
Ile Gln Arg Val Asn Asn Ser Ser Thr Asn Asp Asn Leu Val Arg
                1130                1135                1140
Lys Asn Asp Gln Val Tyr Ile Asn Phe Val Ala Ser Lys Thr His
                1145                1150                1155
Leu Phe Pro Leu Tyr Ala Asp Thr Ala Thr Thr Asn Lys Glu Lys
                1160                1165                1170
Thr Ile Lys Ile Ser Ser Ser Gly Asn Arg Phe Asn Gln Val Val
                1175                1180                1185
Val Met Asn Ser Val Gly Asn Cys Thr Met Asn Phe Lys Asn
                1190                1195                1200
Asn Asn Gly Asn Asn Ile Gly Leu Leu Gly Phe Lys Ala Asp Thr
                1205                1210                1215
Val Val Ala Ser Thr Trp Tyr Tyr Thr His Met Arg Asp His Thr
                1220                1225                1230
Asn Ser Asn Gly Cys Phe Trp Asn Phe Ile Ser Glu Glu His Gly
                1235                1240                1245
Trp Gln Glu Lys
                1250

<210> SEQ ID NO 6
<211> LENGTH: 1274
<212> TYPE: PRT
<213> ORGANISM: Clostridium botulinum
```

<400> SEQUENCE: 6

```
Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
                100                 105                 110

Tyr Ala Lys Pro Tyr Leu Gly Asn Asp His Thr Pro Ile Asp Glu Phe
            115                 120                 125

Ser Pro Val Thr Arg Thr Thr Ser Val Asn Ile Lys Leu Ser Thr Asn
130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Glu Val
        290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
```

```
                  405                 410                 415
Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Ser Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575

Phe Ile Asp Thr Ile Asn Lys Pro Val Asn Ala Ala Leu Phe Ile Asp
            580                 585                 590

Trp Ile Ser Lys Val Ile Arg Asp Phe Thr Thr Glu Ala Thr Gln Lys
        595                 600                 605

Ser Thr Val Asp Lys Ile Ala Asp Ile Ser Leu Ile Val Pro Tyr Val
    610                 615                 620

Gly Leu Ala Leu Asn Ile Ile Glu Ala Glu Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
            660                 665                 670

Asp Ser Tyr Glu Asn Lys Asn Lys Ala Ile Lys Ala Ile Asn Asn Ser
        675                 680                 685

Leu Ile Glu Arg Glu Ala Lys Trp Lys Glu Ile Tyr Ser Trp Ile Val
    690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
            740                 745                 750

Glu Ser Glu Tyr Asn Ile Asn Asn Ile Glu Glu Glu Leu Asn Lys Lys
        755                 760                 765

Val Ser Leu Ala Met Lys Asn Ile Glu Arg Phe Met Thr Glu Ser Ser
    770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
            820                 825                 830
```

-continued

Val Thr Ser Thr Leu Asn Ser Ser Ile Pro Phe Glu Leu Ser Ser Tyr
          835                 840                 845

Thr Asn Asp Lys Ile Leu Ile Ile Tyr Phe Asn Arg Leu Tyr Lys Lys
    850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
                885                 890                 895

Tyr Ile Tyr Ser Thr Asn Arg Asn Gln Phe Gly Ile Tyr Asn Ser Arg
            900                 905                 910

Leu Ser Glu Val Asn Ile Ala Gln Asn Asn Asp Ile Ile Tyr Asn Ser
                915                 920                 925

Arg Tyr Gln Asn Phe Ser Ile Ser Phe Trp Val Arg Ile Pro Lys His
    930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
                965                 970                 975

Cys Glu Ile Ile Trp Thr Leu Gln Asp Thr Ser Gly Asn Lys Glu Asn
            980                 985                 990

Leu Ile Phe Arg Tyr Glu Glu Leu Asn Arg Ile Ser Asn Tyr Ile Asn
            995                 1000                1005

Lys Trp Ile Phe Val Thr Ile Thr Asn Asn Arg Leu Gly Asn Ser
    1010                1015                1020

Arg Ile Tyr Ile Asn Gly Asn Leu Ile Val Glu Lys Ser Ile Ser
    1025                1030                1035

Asn Leu Gly Asp Ile His Val Ser Asp Asn Ile Leu Phe Lys Ile
    1040                1045                1050

Val Gly Cys Asp Asp Glu Thr Tyr Val Gly Ile Arg Tyr Phe Lys
    1055                1060                1065

Val Phe Asn Thr Glu Leu Asp Lys Thr Glu Ile Glu Thr Leu Tyr
    1070                1075                1080

Ser Asn Glu Pro Asp Pro Ser Ile Leu Lys Asn Tyr Trp Gly Asn
    1085                1090                1095

Tyr Leu Leu Tyr Asn Lys Lys Tyr Tyr Leu Phe Asn Leu Leu Arg
    1100                1105                1110

Lys Asp Lys Tyr Ile Thr Leu Asn Ser Gly Ile Leu Asn Ile Asn
    1115                1120                1125

Gln Gln Arg Gly Val Thr Glu Gly Ser Val Phe Leu Asn Tyr Lys
    1130                1135                1140

Leu Tyr Glu Gly Val Glu Val Ile Ile Arg Lys Asn Gly Pro Ile
    1145                1150                1155

Asp Ile Ser Asn Thr Asp Asn Phe Val Arg Lys Asn Asp Leu Ala
    1160                1165                1170

Tyr Ile Asn Val Val Asp Arg Gly Val Glu Tyr Arg Leu Tyr Ala
    1175                1180                1185

Asp Thr Lys Ser Glu Lys Glu Lys Ile Ile Arg Thr Ser Asn Leu
    1190                1195                1200

Asn Asp Ser Leu Gly Gln Ile Ile Val Met Asp Ser Ile Gly Asn
    1205                1210                1215

Asn Cys Thr Met Asn Phe Gln Asn Asn Asn Gly Ser Asn Ile Gly
    1220                1225                1230

-continued

```
Leu Leu Gly Phe His Ser Asn Asn Leu Val Ala Ser Ser Trp Tyr
    1235                1240                1245

Tyr Asn Asn Ile Arg Arg Asn Thr Ser Ser Asn Gly Cys Phe Trp
    1250                1255                1260

Ser Ser Ile Ser Lys Glu Asn Gly Trp Lys Glu
    1265                1270

<210> SEQ ID NO 7
<211> LENGTH: 1297
<212> TYPE: PRT
<213> ORGANISM: Clostridium botulinum

<400> SEQUENCE: 7

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
                20                  25                  30

Tyr Tyr Lys Ala Phe Arg Ile Ile Asp Arg Ile Trp Ile Val Pro Glu
            35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335
```

```
Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
            355                 360                 365

Arg Tyr Ser Tyr Phe Ser Glu Tyr Leu Pro Pro Ile Lys Thr Glu Lys
            370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
                420                 425                 430

Ile Ala Met Cys Lys Pro Val Met Tyr Lys Asn Thr Gly Lys Ser Glu
                435                 440                 445

Gln Cys Ile Ile Val Asn Asn Glu Asp Leu Phe Phe Ile Ala Asn Lys
            450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
            515                 520                 525

Gln Ser Ala Leu Lys Lys Ile Phe Val Asp Gly Asp Ser Leu Phe Glu
            530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
            595                 600                 605

Glu Ser Thr Gln Lys Ser Thr Ile Asp Lys Val Ser Asp Val Ser Ile
            610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
            675                 680                 685

Asn Ala Leu Lys Lys Arg Asp Gln Lys Trp Thr Asp Met Tyr Gly Leu
            690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
                740                 745                 750
```

```
Asn Ile Asn Ile Asp Phe Asn Asp Ile Asp Phe Lys Leu Asn Gln Ser
        755                 760                 765
Ile Asn Leu Ala Ile Asn Ile Asp Asp Phe Ile Asn Gln Cys Ser
770                 775                 780
Ile Ser Tyr Leu Met Asn Arg Met Ile Pro Leu Ala Val Lys Lys Leu
785                 790                 795                 800
Lys Asp Phe Asp Asp Asn Leu Lys Arg Asp Leu Leu Glu Tyr Ile Asp
                805                 810                 815
Thr Asn Glu Leu Tyr Leu Leu Asp Glu Val Asn Ile Leu Lys Ser Lys
            820                 825                 830
Val Asn Arg His Leu Lys Asp Ser Ile Pro Phe Asp Leu Ser Leu Tyr
        835                 840                 845
Thr Lys Asp Thr Ile Leu Ile Gln Val Phe Asn Asn Tyr Ile Ser Asn
850                 855                 860
Ile Ser Ser Asn Ala Ile Leu Ser Leu Ser Tyr Arg Gly Gly Arg Leu
865                 870                 875                 880
Ile Asp Ser Ser Gly Tyr Gly Ala Thr Met Asn Val Gly Ser Asp Val
                885                 890                 895
Ile Phe Asn Asp Ile Gly Asn Gly Gln Phe Lys Leu Asn Asn Ser Glu
        900                 905                 910
Asn Ser Asn Ile Thr Ala His Gln Ser Lys Phe Val Val Tyr Asp Ser
        915                 920                 925
Met Phe Asp Asn Phe Ser Ile Asn Phe Trp Val Arg Thr Pro Lys Tyr
        930                 935                 940
Asn Asn Asn Asp Ile Gln Thr Tyr Leu Gln Asn Glu Tyr Thr Ile Ile
945                 950                 955                 960
Ser Cys Ile Lys Asn Asp Ser Gly Trp Lys Val Ser Ile Lys Gly Asn
                965                 970                 975
Arg Ile Ile Trp Thr Leu Ile Asp Val Asn Ala Lys Ser Lys Ser Ile
            980                 985                 990
Phe Phe Glu Tyr Ser Ile Lys Asp Asn Ile Ser Asp Tyr Ile Asn Lys
            995                 1000                1005
Trp Phe Ser Ile Thr Ile Thr Asn Asp Arg Leu Gly Asn Ala Asn
    1010                1015                1020
Ile Tyr Ile Asn Gly Ser Leu Lys Lys Ser Glu Lys Ile Leu Asn
    1025                1030                1035
Leu Asp Arg Ile Asn Ser Ser Asn Asp Ile Asp Phe Lys Leu Ile
1040                    1045                1050
Asn Cys Thr Asp Thr Thr Lys Phe Val Trp Ile Lys Asp Phe Asn
    1055                1060                1065
Ile Phe Gly Arg Glu Leu Asn Ala Thr Glu Val Ser Ser Leu Tyr
    1070                1075                1080
Trp Ile Gln Ser Ser Thr Asn Thr Leu Lys Asp Phe Trp Gly Asn
    1085                1090                1095
Pro Leu Arg Tyr Asp Thr Gln Tyr Tyr Leu Phe Asn Gln Gly Met
    1100                1105                1110
Gln Asn Ile Tyr Ile Lys Tyr Phe Ser Lys Ala Ser Met Gly Glu
    1115                1120                1125
Thr Ala Pro Arg Thr Asn Phe Asn Asn Ala Ala Ile Asn Tyr Gln
    1130                1135                1140
Asn Leu Tyr Leu Gly Leu Arg Phe Ile Ile Lys Lys Ala Ser Asn
    1145                1150                1155
Ser Arg Asn Ile Asn Asn Asp Asn Ile Val Arg Glu Gly Asp Tyr
```

-continued

```
    1160                1165                1170

Ile Tyr  Leu Asn Ile Asp Asn  Ile Ser Asp Glu Ser  Tyr Arg Val
    1175                1180                1185

Tyr Val  Leu Val Asn Ser Lys  Glu Ile Gln Thr Gln  Leu Phe Leu
    1190                1195                1200

Ala Pro  Ile Asn Asp Asp Pro  Thr Phe Tyr Asp Val  Leu Gln Ile
    1205                1210                1215

Lys Lys  Tyr Tyr Glu Lys Thr  Thr Tyr Asn Cys Gln  Ile Leu Cys
    1220                1225                1230

Glu Lys  Asp Thr Lys Thr Phe  Gly Leu Phe Gly Ile  Gly Lys Phe
    1235                1240                1245

Val Lys  Asp Tyr Gly Tyr Val  Trp Asp Thr Tyr Asp  Asn Tyr Phe
    1250                1255                1260

Cys Ile  Ser Gln Trp Tyr Leu  Arg Arg Ile Ser Glu  Asn Ile Asn
    1265                1270                1275

Lys Leu  Arg Leu Gly Cys Asn  Trp Gln Phe Ile Pro  Val Asp Glu
    1280                1285                1290

Gly Trp  Thr Glu
    1295

<210> SEQ ID NO 8
<211> LENGTH: 1315
<212> TYPE: PRT
<213> ORGANISM: Clostridium tetani

<400> SEQUENCE: 8

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220
```

```
Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
            245                 250                 255

Gln Glu Ile Tyr Met Gln His Thr Tyr Pro Ile Ser Ala Glu Glu Leu
        260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
        290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
```

-continued

```
            645                 650                 655
Tyr Glu Gly Asn Phe Ile Gly Ala Leu Glu Thr Thr Gly Val Val Leu
            660                 665                 670
Leu Leu Glu Tyr Ile Pro Glu Ile Thr Leu Pro Val Ile Ala Ala Leu
            675                 680                 685
Ser Ile Ala Glu Ser Ser Thr Gln Lys Glu Lys Ile Ile Lys Thr Ile
            690                 695                 700
Asp Asn Phe Leu Glu Lys Arg Tyr Glu Lys Trp Ile Glu Val Tyr Lys
705                 710                 715                 720
Leu Val Lys Ala Lys Trp Leu Gly Thr Val Asn Thr Gln Phe Gln Lys
            725                 730                 735
Arg Ser Tyr Gln Met Tyr Arg Ser Leu Glu Tyr Gln Val Asp Ala Ile
            740                 745                 750
Lys Lys Ile Ile Asp Tyr Glu Tyr Lys Ile Tyr Ser Gly Pro Asp Lys
            755                 760                 765
Glu Gln Ile Ala Asp Glu Ile Asn Asn Leu Lys Asn Lys Leu Glu Glu
            770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
            805                 810                 815
Leu Leu Glu Phe Asp Thr Gln Ser Lys Asn Ile Leu Met Gln Tyr Ile
            820                 825                 830
Lys Ala Asn Ser Lys Phe Ile Gly Ile Thr Glu Leu Lys Lys Leu Glu
            835                 840                 845
Ser Lys Ile Asn Lys Val Phe Ser Thr Pro Ile Pro Phe Ser Tyr Ser
850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
            885                 890                 895
Ser Asp Ile Ser Gly Phe Asn Ser Ser Val Ile Thr Tyr Pro Asp Ala
            900                 905                 910
Gln Leu Val Pro Gly Ile Asn Gly Lys Ala Ile His Leu Val Asn Asn
            915                 920                 925
Glu Ser Ser Glu Val Ile Val His Lys Ala Met Asp Ile Glu Tyr Asn
            930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
            965                 970                 975
Ile Ser Ser Met Lys Lys His Ser Leu Ser Ile Gly Ser Gly Trp Ser
            980                 985                 990
Val Ser Leu Lys Gly Asn Asn Leu Ile Trp Thr Leu Lys Asp Ser Ala
            995                 1000                1005
Gly Glu Val Arg Gln Ile Thr Phe Arg Asp Leu Pro Asp Lys Phe
        1010            1015            1020
Asn Ala Tyr Leu Ala Asn Lys Trp Val Phe Ile Thr Ile Thr Asn
        1025            1030            1035
Asp Arg Leu Ser Ser Ala Asn Leu Tyr Ile Asn Gly Val Leu Met
        1040            1045            1050
Gly Ser Ala Glu Ile Thr Gly Leu Gly Ala Ile Arg Glu Asp Asn
        1055            1060            1065
```

```
Asn Ile Thr Leu Lys Leu Asp Arg Cys Asn Asn Asn Gln Tyr
    1070            1075                1080

Val Ser Ile Asp Lys Phe Arg Ile Phe Cys Lys Ala Leu Asn Pro
    1085            1090                1095

Lys Glu Ile Glu Lys Leu Tyr Thr Ser Tyr Leu Ser Ile Thr Phe
    1100            1105                1110

Leu Arg Asp Phe Trp Gly Asn Pro Leu Arg Tyr Asp Thr Glu Tyr
    1115            1120                1125

Tyr Leu Ile Pro Val Ala Ser Ser Lys Asp Val Gln Leu Lys
    1130            1135                1140

Asn Ile Thr Asp Tyr Met Tyr Leu Thr Asn Ala Pro Ser Tyr Thr
    1145            1150                1155

Asn Gly Lys Leu Asn Ile Tyr Tyr Arg Arg Leu Tyr Asn Gly Leu
    1160            1165                1170

Lys Phe Ile Ile Lys Arg Tyr Thr Pro Asn Asn Glu Ile Asp Ser
    1175            1180                1185

Phe Val Lys Ser Gly Asp Phe Ile Lys Leu Tyr Val Ser Tyr Asn
    1190            1195                1200

Asn Asn Glu His Ile Val Gly Tyr Pro Lys Asp Gly Asn Ala Phe
    1205            1210                1215

Asn Asn Leu Asp Arg Ile Leu Arg Val Gly Tyr Asn Ala Pro Gly
    1220            1225                1230

Ile Pro Leu Tyr Lys Lys Met Glu Ala Val Lys Leu Arg Asp Leu
    1235            1240                1245

Lys Thr Tyr Ser Val Gln Leu Lys Leu Tyr Asp Asp Lys Asn Ala
    1250            1255                1260

Ser Leu Gly Leu Val Gly Thr His Asn Gly Gln Ile Gly Asn Asp
    1265            1270                1275

Pro Asn Arg Asp Ile Leu Ile Ala Ser Asn Trp Tyr Phe Asn His
    1280            1285                1290

Leu Lys Asp Lys Ile Leu Gly Cys Asp Trp Tyr Phe Val Pro Thr
    1295            1300                1305

Asp Glu Gly Trp Thr Asn Asp
    1310            1315

<210> SEQ ID NO 9
<211> LENGTH: 177
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(168)

<400> SEQUENCE: 9 gtc gac gag ctc gat atc ggt ggt ggt ggt agc ggt ggt ggc ggt tca      48
Val Asp Glu Leu Asp Ile Gly Gly Gly Gly Ser Gly Gly Gly Gly Ser
1               5                   10                  15 ggt ggt ggt ggc agt ggt tat tgt gca gaa aaa ggt att cgc tgt gat      96
Gly Gly Gly Gly Ser Gly Tyr Cys Ala Glu Lys Gly Ile Arg Cys Asp
                20                  25                  30 gat att cat tgt tgc acc ggt ctg aaa tgt aaa tgt aat gcc agc ggt     144
Asp Ile His Cys Cys Thr Gly Leu Lys Cys Lys Cys Asn Ala Ser Gly
            35                  40                  45 tat aat tgc gtg tgc cgc aaa aag taactcgag                           177
```

Tyr Asn Cys Val Cys Arg Lys Lys
    50                  55

<210> SEQ ID NO 10
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Val Asp Glu Leu Asp Ile Gly Gly Gly Gly Ser Gly Gly Gly Gly Ser
1               5                   10                  15

Gly Gly Gly Gly Ser Gly Tyr Cys Ala Glu Lys Gly Ile Arg Cys Asp
            20                  25                  30

Asp Ile His Cys Cys Thr Gly Leu Lys Cys Lys Cys Asn Ala Ser Gly
        35                  40                  45

Tyr Asn Cys Val Cys Arg Lys Lys
    50                  55

<210> SEQ ID NO 11
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(174)

<400> SEQUENCE: 11 gtc gac gag ctc gat atc ggt ggt ggt ggt agc ggt ggt ggc ggt tca        48
Val Asp Glu Leu Asp Ile Gly Gly Gly Gly Ser Gly Gly Gly Gly Ser
1               5                   10                  15 ggt ggt ggt ggc agt ggt tat tgt gca gaa aaa ggt att cgc tgt gat        96
Gly Gly Gly Gly Ser Gly Tyr Cys Ala Glu Lys Gly Ile Arg Cys Asp
            20                  25                  30 gat att cat tgt tgc acc ggt ctg aaa tgt aaa tgt aat gcc agc ggt       144
Asp Ile His Cys Cys Thr Gly Leu Lys Cys Lys Cys Asn Ala Ser Gly
        35                  40                  45 tat aat tgc gtg tgc cgc aaa aag gtc gac                               174
Tyr Asn Cys Val Cys Arg Lys Lys Val Asp
    50                  55

<210> SEQ ID NO 12
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Asp Glu Leu Asp Ile Gly Gly Gly Gly Ser Gly Gly Gly Gly Ser
1               5                   10                  15

Gly Gly Gly Gly Ser Gly Tyr Cys Ala Glu Lys Gly Ile Arg Cys Asp
            20                  25                  30

Asp Ile His Cys Cys Thr Gly Leu Lys Cys Lys Cys Asn Ala Ser Gly
        35                  40                  45

Tyr Asn Cys Val Cys Arg Lys Lys Val Asp
    50                  55

```
<210> SEQ ID NO 13
<211> LENGTH: 3795
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(3792)

<400> SEQUENCE: 13 atg acc tgg ccg gtg aaa gac ttt aac tat agc gat ccg gtg aac gat        48
Met Thr Trp Pro Val Lys Asp Phe Asn Tyr Ser Asp Pro Val Asn Asp
1               5                   10                  15 aac gat att ctg tat ctg cgt atc ccg cag aac aaa ctg att acc acc        96
Asn Asp Ile Leu Tyr Leu Arg Ile Pro Gln Asn Lys Leu Ile Thr Thr
            20                  25                  30 ccg gtg aaa gcg ttc atg att acc cag aac att tgg gtg att ccg gaa       144
Pro Val Lys Ala Phe Met Ile Thr Gln Asn Ile Trp Val Ile Pro Glu
        35                  40                  45 cgt ttt agc agc gat acc aat ccg agc ctg agc aaa ccg ccg cgt ccg       192
Arg Phe Ser Ser Asp Thr Asn Pro Ser Leu Ser Lys Pro Pro Arg Pro
    50                  55                  60 acc agc aaa tat cag agc tat tac gat ccg agc tat ctg agc acc gat       240
Thr Ser Lys Tyr Gln Ser Tyr Tyr Asp Pro Ser Tyr Leu Ser Thr Asp
65                  70                  75                  80 gaa cag aaa gat acc ttc ctg aaa ggc atc atc aaa ctg ttc aaa cgc       288
Glu Gln Lys Asp Thr Phe Leu Lys Gly Ile Ile Lys Leu Phe Lys Arg
                85                  90                  95 att aac gaa cgc gat att ggc aaa aaa ctg atc aac tat ctg gtg gtg       336
Ile Asn Glu Arg Asp Ile Gly Lys Lys Leu Ile Asn Tyr Leu Val Val
            100                 105                 110 ggc agc ccg ttt atg ggc gat agc agc acc ccg gaa gat acc ttt gat       384
Gly Ser Pro Phe Met Gly Asp Ser Ser Thr Pro Glu Asp Thr Phe Asp
        115                 120                 125 ttt acc cgt cat acc acg aac att gcg gtg gaa aaa ttt gaa aac ggc       432
Phe Thr Arg His Thr Thr Asn Ile Ala Val Glu Lys Phe Glu Asn Gly
    130                 135                 140 agc tgg aaa gtg acc aac att att acc ccg agc gtg ctg att ttt ggc       480
Ser Trp Lys Val Thr Asn Ile Ile Thr Pro Ser Val Leu Ile Phe Gly
145                 150                 155                 160 ccg ctg ccg aac att ctg gat tat acc gcg agc ctg acg ctg caa ggc       528
Pro Leu Pro Asn Ile Leu Asp Tyr Thr Ala Ser Leu Thr Leu Gln Gly
                165                 170                 175 cag cag agc aat ccg agc ttt gaa ggc ttt ggc acc ctg agc att ctg       576
Gln Gln Ser Asn Pro Ser Phe Glu Gly Phe Gly Thr Leu Ser Ile Leu
            180                 185                 190 aaa gtg gcg ccg gaa ttt ctg ctg acc ttt agc gat gtg acc agc aac       624
Lys Val Ala Pro Glu Phe Leu Leu Thr Phe Ser Asp Val Thr Ser Asn
        195                 200                 205 cag agc agc gcg gtg ctg ggc aaa agc att ttt tgc atg gat ccg gtg       672
Gln Ser Ser Ala Val Leu Gly Lys Ser Ile Phe Cys Met Asp Pro Val
    210                 215                 220 att gcg ctg atg cat gaa ctg acc cat agc ctg cat cag ctg tat ggc       720
Ile Ala Leu Met His Glu Leu Thr His Ser Leu His Gln Leu Tyr Gly
225                 230                 235                 240 att aac att ccg agc gat aaa cgt att cgt ccg cag gtg agc gaa ggc       768
Ile Asn Ile Pro Ser Asp Lys Arg Ile Arg Pro Gln Val Ser Glu Gly
                245                 250                 255 ttt ttt agc cag gat ggc ccg aac gtg cag ttt gaa gaa ctg tat acc       816
```

```
Phe Phe Ser Gln Asp Gly Pro Asn Val Gln Phe Glu Glu Leu Tyr Thr
            260                 265                 270 ttt ggc ggc ctg gat gtg gaa att att ccg cag att gaa cgt agc cag      864
Phe Gly Gly Leu Asp Val Glu Ile Ile Pro Gln Ile Glu Arg Ser Gln
        275                 280                 285 ctg cgt gaa aaa gcg ctg ggc cac tat aaa gat att gcg aaa cgc ctg      912
Leu Arg Glu Lys Ala Leu Gly His Tyr Lys Asp Ile Ala Lys Arg Leu
    290                 295                 300 aac aac atc aac aaa acc att ccg agc agc tgg att agc aac atc gat      960
Asn Asn Ile Asn Lys Thr Ile Pro Ser Ser Trp Ile Ser Asn Ile Asp
305                 310                 315                 320 aaa tac aaa aaa atc ttc agc gaa aaa tat aac ttc gat aaa gat aac     1008
Lys Tyr Lys Lys Ile Phe Ser Glu Lys Tyr Asn Phe Asp Lys Asp Asn
            325                 330                 335 acc ggc aac ttc gtg gtg aac att gat aaa ttc aac agc ctg tat agc     1056
Thr Gly Asn Phe Val Val Asn Ile Asp Lys Phe Asn Ser Leu Tyr Ser
        340                 345                 350 gat ctg acc aac gtg atg agc gaa gtg gtg tat agc agc cag tat aac     1104
Asp Leu Thr Asn Val Met Ser Glu Val Val Tyr Ser Ser Gln Tyr Asn
    355                 360                 365 gtg aaa aac cgc acc cat tat ttc agc cgt cat tat ctg ccg gtg ttt     1152
Val Lys Asn Arg Thr His Tyr Phe Ser Arg His Tyr Leu Pro Val Phe
370                 375                 380 gcg aat att ctg gat gat aac atc tat acc atc cgt gat ggc ttt aac     1200
Ala Asn Ile Leu Asp Asp Asn Ile Tyr Thr Ile Arg Asp Gly Phe Asn
385                 390                 395                 400 ctg acc aac aaa ggc ttt aac att gaa aac agc ggc cag aac att gaa     1248
Leu Thr Asn Lys Gly Phe Asn Ile Glu Asn Ser Gly Gln Asn Ile Glu
            405                 410                 415 cgt aat ccg gcg ctg cag aaa ctg tct agc gaa agc gtg gtg gac ctg     1296
Arg Asn Pro Ala Leu Gln Lys Leu Ser Ser Glu Ser Val Val Asp Leu
        420                 425                 430 ttt acc aaa gtg tgc ctg cgt ctg acc ctg gtg cca cgc ggt agc acc     1344
Phe Thr Lys Val Cys Leu Arg Leu Thr Leu Val Pro Arg Gly Ser Thr
    435                 440                 445 tgc atc aaa gtg aaa aac aac cgt ctg ccg tat gtg gcg gat aaa gat     1392
Cys Ile Lys Val Lys Asn Asn Arg Leu Pro Tyr Val Ala Asp Lys Asp
450                 455                 460 agc att agc cag gaa atc ttc gaa aac aaa atc atc acc gat gaa acc     1440
Ser Ile Ser Gln Glu Ile Phe Glu Asn Lys Ile Ile Thr Asp Glu Thr
465                 470                 475                 480 aac gtg cag aac tac agc gat aaa ttc agc ctg gat gaa agc att ctg     1488
Asn Val Gln Asn Tyr Ser Asp Lys Phe Ser Leu Asp Glu Ser Ile Leu
            485                 490                 495 gat ggc cag gtg ccg att aat ccg gaa att gtg gat ccg ctg ctg ccg     1536
Asp Gly Gln Val Pro Ile Asn Pro Glu Ile Val Asp Pro Leu Leu Pro
        500                 505                 510 aac gtg aac atg gaa ccg ctg aac ctg ccg ggc gaa gaa att gtg ttc     1584
Asn Val Asn Met Glu Pro Leu Asn Leu Pro Gly Glu Glu Ile Val Phe
    515                 520                 525 tat gat gat att acc aaa tat gtg gat tat ctg aac agc tac tac tat     1632
Tyr Asp Asp Ile Thr Lys Tyr Val Asp Tyr Leu Asn Ser Tyr Tyr Tyr
530                 535                 540 ctg gaa agc cag aaa ctg agc aac aac gtg gaa aac att acc ctg acc     1680
Leu Glu Ser Gln Lys Leu Ser Asn Asn Val Glu Asn Ile Thr Leu Thr
545                 550                 555                 560 acc tct gtg gaa gaa gcg ctg ggt tat agc aac aaa atc tac acc ttt     1728
Thr Ser Val Glu Glu Ala Leu Gly Tyr Ser Asn Lys Ile Tyr Thr Phe
            565                 570                 575
```

-continued

| | | |
|---|---|---|
| ctg ccg agc ctg gcc gaa aaa gtg aac aaa ggc gtg cag gcg ggc ctg<br>Leu Pro Ser Leu Ala Glu Lys Val Asn Lys Gly Val Gln Ala Gly Leu<br>580 585 590 | | 1776 |
| ttt ctg aac tgg gcg aac gaa gtg gtg gaa gat ttt acc acc aat atc<br>Phe Leu Asn Trp Ala Asn Glu Val Val Glu Asp Phe Thr Thr Asn Ile<br>595 600 605 | | 1824 |
| atg aaa aaa gat acc ctg gat aaa atc agc gat gtg agc gtg att att<br>Met Lys Lys Asp Thr Leu Asp Lys Ile Ser Asp Val Ser Val Ile Ile<br>610 615 620 | | 1872 |
| ccg tat att ggt ccg gcg ctg aac att ggc aac agc gcc ctg cgt ggc<br>Pro Tyr Ile Gly Pro Ala Leu Asn Ile Gly Asn Ser Ala Leu Arg Gly<br>625 630 635 640 | | 1920 |
| aac ttt aac cag gcg ttt gcg acc gcg ggt gtg gcg ttt ctg ctg gaa<br>Asn Phe Asn Gln Ala Phe Ala Thr Ala Gly Val Ala Phe Leu Leu Glu<br>645 650 655 | | 1968 |
| ggc ttt ccg gaa ttc acc att ccg gcg ctg ggc gtg ttt acc ttt tat<br>Gly Phe Pro Glu Phe Thr Ile Pro Ala Leu Gly Val Phe Thr Phe Tyr<br>660 665 670 | | 2016 |
| agc agc att cag gaa cgc gaa aaa atc atc aaa acc atc gaa aac tgc<br>Ser Ser Ile Gln Glu Arg Glu Lys Ile Ile Lys Thr Ile Glu Asn Cys<br>675 680 685 | | 2064 |
| ctg gaa cag cgt gtg aaa cgt tgg aaa gat agc tat cag tgg atg gtg<br>Leu Glu Gln Arg Val Lys Arg Trp Lys Asp Ser Tyr Gln Trp Met Val<br>690 695 700 | | 2112 |
| agc aac tgg ctg tct cgt att acc acc cag ttt aac cac atc aac tat<br>Ser Asn Trp Leu Ser Arg Ile Thr Thr Gln Phe Asn His Ile Asn Tyr<br>705 710 715 720 | | 2160 |
| cag atg tat gac agc ctg agc tat cag gcg gat gcg att aaa gcg aaa<br>Gln Met Tyr Asp Ser Leu Ser Tyr Gln Ala Asp Ala Ile Lys Ala Lys<br>725 730 735 | | 2208 |
| atc gat ctg gaa tac aaa aaa tac agc ggc agc gat aaa gaa aac atc<br>Ile Asp Leu Glu Tyr Lys Lys Tyr Ser Gly Ser Asp Lys Glu Asn Ile<br>740 745 750 | | 2256 |
| aaa agc cag gtg gaa aac ctg aaa aac agc ctg gat gtg aaa att agc<br>Lys Ser Gln Val Glu Asn Leu Lys Asn Ser Leu Asp Val Lys Ile Ser<br>755 760 765 | | 2304 |
| gaa gcc atg aat aac atc aac aaa ttc atc cgt gaa tgc agc gtg acc<br>Glu Ala Met Asn Asn Ile Asn Lys Phe Ile Arg Glu Cys Ser Val Thr<br>770 775 780 | | 2352 |
| tac ctg ttt aaa aac atg ctg ccg aaa gtg att gat gaa ctg aac aaa<br>Tyr Leu Phe Lys Asn Met Leu Pro Lys Val Ile Asp Glu Leu Asn Lys<br>785 790 795 800 | | 2400 |
| ttt gat ctg cgc acc aaa acc gaa ctg att aac ctg atc gat agc cat<br>Phe Asp Leu Arg Thr Lys Thr Glu Leu Ile Asn Leu Ile Asp Ser His<br>805 810 815 | | 2448 |
| aac att att ctg gtg ggc gaa gtg gat cgt ctg aaa gcg aaa gtg aac<br>Asn Ile Ile Leu Val Gly Glu Val Asp Arg Leu Lys Ala Lys Val Asn<br>820 825 830 | | 2496 |
| gaa agc ttc gaa aac acc atg ccg ttt aac atc ttc agc tac acc aac<br>Glu Ser Phe Glu Asn Thr Met Pro Phe Asn Ile Phe Ser Tyr Thr Asn<br>835 840 845 | | 2544 |
| aac agc ctg ctg aaa gat att atc aac gaa tat ttt aac agc atc aac<br>Asn Ser Leu Leu Lys Asp Ile Ile Asn Glu Tyr Phe Asn Ser Ile Asn<br>850 855 860 | | 2592 |
| gat agc aaa att ctg agc ctg cag aac aaa aaa aac gcg ctg gtt gat<br>Asp Ser Lys Ile Leu Ser Leu Gln Asn Lys Lys Asn Ala Leu Val Asp<br>865 870 875 880 | | 2640 |
| acc agc ggc tat aac gcg gaa gtg cgt gtg ggc gat aac gtg cag ctg<br>Thr Ser Gly Tyr Asn Ala Glu Val Arg Val Gly Asp Asn Val Gln Leu<br>885 890 895 | | 2688 |

-continued

```
aac acc att tat acc aac gat ttc aaa ctg agc agc agc ggc gat aaa    2736
Asn Thr Ile Tyr Thr Asn Asp Phe Lys Leu Ser Ser Ser Gly Asp Lys
        900                 905                 910 att att gtg aac ctg aat aac aac att ctg tac agc gcg att tat gaa    2784
Ile Ile Val Asn Leu Asn Asn Asn Ile Leu Tyr Ser Ala Ile Tyr Glu
        915                 920                 925 aac agc agc gtg agc ttt tgg atc aaa atc agc aaa gat ctg acc aac    2832
Asn Ser Ser Val Ser Phe Trp Ile Lys Ile Ser Lys Asp Leu Thr Asn
930                 935                 940 agc cat aac gaa tac acc atc atc aac agc att gaa cag aac agc ggc    2880
Ser His Asn Glu Tyr Thr Ile Ile Asn Ser Ile Glu Gln Asn Ser Gly
945                 950                 955                 960 tgg aaa ctg tgc att cgt aac ggc aac att gaa tgg att ctg cag gat    2928
Trp Lys Leu Cys Ile Arg Asn Gly Asn Ile Glu Trp Ile Leu Gln Asp
                965                 970                 975 gtg aac cgc aaa tat aaa agc ctg atc ttc gat tat agc gaa agc ctg    2976
Val Asn Arg Lys Tyr Lys Ser Leu Ile Phe Asp Tyr Ser Glu Ser Leu
            980                 985                 990 agc cat acc ggc tat acc aac aaa tgg ttc ttt gtg acc atc acc aac    3024
Ser His Thr Gly Tyr Thr Asn Lys Trp Phe Phe Val Thr Ile Thr Asn
        995                 1000                1005 aac att atg ggc tat atg aaa ctg tat atc aac ggc gaa ctg aaa        3069
Asn Ile Met Gly Tyr Met Lys Leu Tyr Ile Asn Gly Glu Leu Lys
    1010                1015                1020 cag agc cag aaa atc gaa gat ctg gat gaa gtg aaa ctg gat aaa        3114
Gln Ser Gln Lys Ile Glu Asp Leu Asp Glu Val Lys Leu Asp Lys
1025                1030                1035 acc atc gtg ttt ggc atc gat gaa aac att gat gaa aac cag atg        3159
Thr Ile Val Phe Gly Ile Asp Glu Asn Ile Asp Glu Asn Gln Met
    1040                1045                1050 ctg tgg att cgc gat ttt aac atc ttt agc aaa gaa ctg agc aac        3204
Leu Trp Ile Arg Asp Phe Asn Ile Phe Ser Lys Glu Leu Ser Asn
    1055                1060                1065 gaa gat att aac atc gtg tac gaa ggc cag att gag ctc ggt ggt        3249
Glu Asp Ile Asn Ile Val Tyr Glu Gly Gln Ile Glu Leu Gly Gly
1070                1075                1080 ggt ggt agc ggt ggt ggc ggt agt cgt ccg agc ggt cgt aaa agc        3294
Gly Gly Ser Gly Gly Gly Gly Ser Arg Pro Ser Gly Arg Lys Ser
1085                1090                1095 agc aaa atg cag gca ttt cgt att tgg gat gtg aat cag aaa acc        3339
Ser Lys Met Gln Ala Phe Arg Ile Trp Asp Val Asn Gln Lys Thr
1100                1105                1110 ttt tat ctg cgc aac aat cag ctg gtt gca ggt tat ctg cag ggt        3384
Phe Tyr Leu Arg Asn Asn Gln Leu Val Ala Gly Tyr Leu Gln Gly
    1115                1120                1125 ccg aat gtt aat ctg gaa gaa aaa att gat gtg gtg ccg att gaa        3429
Pro Asn Val Asn Leu Glu Glu Lys Ile Asp Val Val Pro Ile Glu
    1130                1135                1140 ccg cat gca ctg ttt ctg ggt att cat ggt ggt aaa atg tgt ctg        3474
Pro His Ala Leu Phe Leu Gly Ile His Gly Gly Lys Met Cys Leu
1145                1150                1155 agc tgt gtt aaa agc ggt gat gaa acc cgt ctg cag ctg gaa gca        3519
Ser Cys Val Lys Ser Gly Asp Glu Thr Arg Leu Gln Leu Glu Ala
1160                1165                1170 gtg aat atc acc gat ctg agc gaa aat cgt aaa cag gat aaa cgc        3564
Val Asn Ile Thr Asp Leu Ser Glu Asn Arg Lys Gln Asp Lys Arg
    1175                1180                1185 ttt gcc ttt att cgt agc gat agc ggt ccg acc acc agt ttt gaa        3609
Phe Ala Phe Ile Arg Ser Asp Ser Gly Pro Thr Thr Ser Phe Glu
```

```
                    1190                1195                1200
agc  gca  gca  tgt  ccg  ggt  tgg  ttt  ctg  tgt  acc  gca  atg  gaa  gca        3654
Ser  Ala  Ala  Cys  Pro  Gly  Trp  Phe  Leu  Cys  Thr  Ala  Met  Glu  Ala
     1205                1210                1215 gat  cag  ccg  gtt  agc  ctg  acc  aat  atg  ccg  gat  gaa  ggt  gtt  atg        3699
Asp  Gln  Pro  Val  Ser  Leu  Thr  Asn  Met  Pro  Asp  Glu  Gly  Val  Met
     1220                1225                1230 gtg  acc  aaa  ttc  tat  ttt  cag  gaa  gat  gaa  gtc  gac  ctg  gtg  cca        3744
Val  Thr  Lys  Phe  Tyr  Phe  Gln  Glu  Asp  Glu  Val  Asp  Leu  Val  Pro
     1235                1240                1245 cgc  ggt  agc  aag  ctt  gcg  gcc  gca  ctc  gag  cac  cac  cac  cac  cac        3789
Arg  Gly  Ser  Lys  Leu  Ala  Ala  Ala  Leu  Glu  His  His  His  His  His
     1250                1255                1260 cac  tga                                                                          3795
His
```

<210> SEQ ID NO 14
<211> LENGTH: 1264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255
```

```
Phe Phe Ser Gln Asp Gly Pro Asn Val Gln Phe Glu Leu Tyr Thr
            260                 265                 270
Phe Gly Gly Leu Asp Val Glu Ile Ile Pro Gln Ile Glu Arg Ser Gln
            275                 280                 285
Leu Arg Glu Lys Ala Leu Gly His Tyr Lys Asp Ile Ala Lys Arg Leu
290                 295                 300
Asn Asn Ile Asn Lys Thr Ile Pro Ser Ser Trp Ile Ser Asn Ile Asp
305                 310                 315                 320
Lys Tyr Lys Lys Ile Phe Ser Glu Lys Tyr Asn Phe Asp Lys Asp Asn
                325                 330                 335
Thr Gly Asn Phe Val Val Asn Ile Asp Lys Phe Asn Ser Leu Tyr Ser
            340                 345                 350
Asp Leu Thr Asn Val Met Ser Glu Val Val Tyr Ser Ser Gln Tyr Asn
            355                 360                 365
Val Lys Asn Arg Thr His Tyr Phe Ser Arg His Tyr Leu Pro Val Phe
370                 375                 380
Ala Asn Ile Leu Asp Asp Asn Ile Tyr Thr Ile Arg Asp Gly Phe Asn
385                 390                 395                 400
Leu Thr Asn Lys Gly Phe Asn Ile Glu Asn Ser Gly Gln Asn Ile Glu
                405                 410                 415
Arg Asn Pro Ala Leu Gln Lys Leu Ser Ser Glu Ser Val Val Asp Leu
            420                 425                 430
Phe Thr Lys Val Cys Leu Arg Leu Thr Leu Val Pro Arg Gly Ser Thr
            435                 440                 445
Cys Ile Lys Val Lys Asn Asn Arg Leu Pro Tyr Val Ala Asp Lys Asp
450                 455                 460
Ser Ile Ser Gln Glu Ile Phe Glu Asn Lys Ile Ile Thr Asp Glu Thr
465                 470                 475                 480
Asn Val Gln Asn Tyr Ser Asp Lys Phe Ser Leu Asp Glu Ser Ile Leu
                485                 490                 495
Asp Gly Gln Val Pro Ile Asn Pro Glu Ile Val Asp Pro Leu Leu Pro
            500                 505                 510
Asn Val Asn Met Glu Pro Leu Asn Leu Pro Gly Glu Glu Ile Val Phe
            515                 520                 525
Tyr Asp Asp Ile Thr Lys Tyr Val Asp Tyr Leu Asn Ser Tyr Tyr Tyr
530                 535                 540
Leu Glu Ser Gln Lys Leu Ser Asn Asn Val Glu Asn Ile Thr Leu Thr
545                 550                 555                 560
Thr Ser Val Glu Glu Ala Leu Gly Tyr Ser Asn Lys Ile Tyr Thr Phe
                565                 570                 575
Leu Pro Ser Leu Ala Glu Lys Val Asn Lys Gly Val Gln Ala Gly Leu
            580                 585                 590
Phe Leu Asn Trp Ala Asn Glu Val Val Glu Asp Phe Thr Thr Asn Ile
            595                 600                 605
Met Lys Lys Asp Thr Leu Asp Lys Ile Ser Asp Val Ser Val Ile Ile
            610                 615                 620
Pro Tyr Ile Gly Pro Ala Leu Asn Ile Gly Asn Ser Ala Leu Arg Gly
625                 630                 635                 640
Asn Phe Asn Gln Ala Phe Ala Thr Ala Gly Val Ala Phe Leu Leu Glu
                645                 650                 655
Gly Phe Pro Glu Phe Thr Ile Pro Ala Leu Gly Val Phe Thr Phe Tyr
            660                 665                 670
```

-continued

```
Ser Ser Ile Gln Glu Arg Glu Lys Ile Ile Lys Thr Ile Glu Asn Cys
            675                 680                 685

Leu Glu Gln Arg Val Lys Arg Trp Lys Asp Ser Tyr Gln Trp Met Val
690                 695                 700

Ser Asn Trp Leu Ser Arg Ile Thr Thr Gln Phe Asn His Ile Asn Tyr
705                 710                 715                 720

Gln Met Tyr Asp Ser Leu Ser Tyr Gln Ala Asp Ala Ile Lys Ala Lys
            725                 730                 735

Ile Asp Leu Glu Tyr Lys Lys Tyr Ser Gly Ser Asp Lys Glu Asn Ile
            740                 745                 750

Lys Ser Gln Val Glu Asn Leu Lys Asn Ser Leu Asp Val Lys Ile Ser
            755                 760                 765

Glu Ala Met Asn Asn Ile Asn Lys Phe Ile Arg Glu Cys Ser Val Thr
770                 775                 780

Tyr Leu Phe Lys Asn Met Leu Pro Lys Val Ile Asp Glu Leu Asn Lys
785                 790                 795                 800

Phe Asp Leu Arg Thr Lys Thr Glu Leu Ile Asn Leu Ile Asp Ser His
            805                 810                 815

Asn Ile Ile Leu Val Gly Glu Val Asp Arg Leu Lys Ala Lys Val Asn
            820                 825                 830

Glu Ser Phe Glu Asn Thr Met Pro Phe Asn Ile Phe Ser Tyr Thr Asn
            835                 840                 845

Asn Ser Leu Leu Lys Asp Ile Ile Asn Glu Tyr Phe Asn Ser Ile Asn
            850                 855                 860

Asp Ser Lys Ile Leu Ser Leu Gln Asn Lys Lys Asn Ala Leu Val Asp
865                 870                 875                 880

Thr Ser Gly Tyr Asn Ala Glu Val Arg Val Gly Asp Asn Val Gln Leu
            885                 890                 895

Asn Thr Ile Tyr Thr Asn Asp Phe Lys Leu Ser Ser Ser Gly Asp Lys
            900                 905                 910

Ile Ile Val Asn Leu Asn Asn Asn Ile Leu Tyr Ser Ala Ile Tyr Glu
            915                 920                 925

Asn Ser Ser Val Ser Phe Trp Ile Lys Ile Ser Lys Asp Leu Thr Asn
930                 935                 940

Ser His Asn Glu Tyr Thr Ile Ile Asn Ser Ile Glu Gln Asn Ser Gly
945                 950                 955                 960

Trp Lys Leu Cys Ile Arg Asn Gly Asn Ile Glu Trp Ile Leu Gln Asp
            965                 970                 975

Val Asn Arg Lys Tyr Lys Ser Leu Ile Phe Asp Tyr Ser Glu Ser Leu
            980                 985                 990

Ser His Thr Gly Tyr Thr Asn Lys Trp Phe Phe Val Thr Ile Thr Asn
            995                 1000                1005

Asn Ile Met Gly Tyr Met Lys Leu Tyr Ile Asn Gly Glu Leu Lys
        1010                1015                1020

Gln Ser Gln Lys Ile Glu Asp Leu Asp Glu Val Lys Leu Asp Lys
        1025                1030                1035

Thr Ile Val Phe Gly Ile Asp Glu Asn Ile Asp Glu Asn Gln Met
        1040                1045                1050

Leu Trp Ile Arg Asp Phe Asn Ile Phe Ser Lys Glu Leu Ser Asn
        1055                1060                1065

Glu Asp Ile Asn Ile Val Tyr Glu Gly Gln Ile Glu Leu Gly Gly
        1070                1075                1080

Gly Gly Ser Gly Gly Gly Gly Ser Arg Pro Ser Gly Arg Lys Ser
```

```
                    1085                1090                1095

Ser Lys Met Gln Ala Phe Arg Ile Trp Asp Val Asn Gln Lys Thr
    1100                1105                1110

Phe Tyr Leu Arg Asn Asn Gln Leu Val Ala Gly Tyr Leu Gln Gly
    1115                1120                1125

Pro Asn Val Asn Leu Glu Glu Lys Ile Asp Val Pro Ile Glu
    1130                1135                1140

Pro His Ala Leu Phe Leu Gly Ile His Gly Gly Lys Met Cys Leu
    1145                1150                1155

Ser Cys Val Lys Ser Gly Asp Glu Thr Arg Leu Gln Leu Glu Ala
    1160                1165                1170

Val Asn Ile Thr Asp Leu Ser Glu Asn Arg Lys Gln Asp Lys Arg
    1175                1180                1185

Phe Ala Phe Ile Arg Ser Asp Ser Gly Pro Thr Thr Ser Phe Glu
    1190                1195                1200

Ser Ala Ala Cys Pro Gly Trp Phe Leu Cys Thr Ala Met Glu Ala
    1205                1210                1215

Asp Gln Pro Val Ser Leu Thr Asn Met Pro Asp Glu Gly Val Met
    1220                1225                1230

Val Thr Lys Phe Tyr Phe Gln Glu Asp Glu Val Asp Leu Val Pro
    1235                1240                1245

Arg Gly Ser Lys Leu Ala Ala Ala Leu Glu His His His His His
    1250                1255                1260

His

<210> SEQ ID NO 15
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(147)

<400> SEQUENCE: 15 gag ctc gat atc ggt ggt ggt ggt agc ggt ggt ggc ggt tca ggt ggt    48
Glu Leu Asp Ile Gly Gly Gly Gly Ser Gly Gly Gly Gly Ser Gly Gly
1               5                   10                  15 ggt ggc agc gtt acc cat cgt ctg gct ggt ctg ctg tct cgt agc ggt    96
Gly Gly Ser Val Thr His Arg Leu Ala Gly Leu Leu Ser Arg Ser Gly
            20                  25                  30 ggt gtt gtg aaa aac aat ttt gtg ccg aca aat gtt ggt agc aaa gca   144
Gly Val Val Lys Asn Asn Phe Val Pro Thr Asn Val Gly Ser Lys Ala
        35                  40                  45 ttt taactcgag                                                      156
Phe

<210> SEQ ID NO 16
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Leu Asp Ile Gly Gly Gly Gly Ser Gly Gly Gly Gly Ser Gly Gly
1               5                   10                  15
```

```
Gly Gly Ser Val Thr His Arg Leu Ala Gly Leu Leu Ser Arg Ser Gly
            20                  25                  30

Gly Val Val Lys Asn Asn Phe Val Pro Thr Asn Val Gly Ser Lys Ala
        35                  40                  45

Phe

<210> SEQ ID NO 17
<211> LENGTH: 3387
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(3378)

<400> SEQUENCE: 17 atg acc tgg ccg gtg aaa gac ttt aac tat agc gat ccg gtg aac gat      48
Met Thr Trp Pro Val Lys Asp Phe Asn Tyr Ser Asp Pro Val Asn Asp
1               5                   10                  15 aac gat att ctg tat ctg cgt atc ccg cag aac aaa ctg att acc acc      96
Asn Asp Ile Leu Tyr Leu Arg Ile Pro Gln Asn Lys Leu Ile Thr Thr
            20                  25                  30 ccg gtg aaa gcg ttc atg att acc cag aac att tgg gtg att ccg gaa     144
Pro Val Lys Ala Phe Met Ile Thr Gln Asn Ile Trp Val Ile Pro Glu
        35                  40                  45 cgt ttt agc agc gat acc aat ccg agc ctg agc aaa ccg ccg cgt ccg     192
Arg Phe Ser Ser Asp Thr Asn Pro Ser Leu Ser Lys Pro Pro Arg Pro
50                  55                  60 acc agc aaa tat cag agc tat tac gat ccg agc tat ctg agc acc gat     240
Thr Ser Lys Tyr Gln Ser Tyr Tyr Asp Pro Ser Tyr Leu Ser Thr Asp
65                  70                  75                  80 gaa cag aaa gat acc ttc ctg aaa ggc atc atc aaa ctg ttc aaa cgc     288
Glu Gln Lys Asp Thr Phe Leu Lys Gly Ile Ile Lys Leu Phe Lys Arg
                85                  90                  95 att aac gaa cgc gat att ggc aaa aaa ctg atc aac tat ctg gtg gtg     336
Ile Asn Glu Arg Asp Ile Gly Lys Lys Leu Ile Asn Tyr Leu Val Val
            100                 105                 110 ggc agc ccg ttt atg ggc gat agc agc acc ccg gaa gat acc ttt gat     384
Gly Ser Pro Phe Met Gly Asp Ser Ser Thr Pro Glu Asp Thr Phe Asp
        115                 120                 125 ttt acc cgt cat acc acg aac att gcg gtg gaa aaa ttt gaa aac ggc     432
Phe Thr Arg His Thr Thr Asn Ile Ala Val Glu Lys Phe Glu Asn Gly
130                 135                 140 agc tgg aaa gtg acc aac att att acc ccg agc gtg ctg att ttt ggc     480
Ser Trp Lys Val Thr Asn Ile Ile Thr Pro Ser Val Leu Ile Phe Gly
145                 150                 155                 160 ccg ctg ccg aac att ctg gat tat acc gcg agc ctg acg ctg caa ggc     528
Pro Leu Pro Asn Ile Leu Asp Tyr Thr Ala Ser Leu Thr Leu Gln Gly
                165                 170                 175 cag cag agc aat ccg agc ttt gaa ggc ttt ggc acc ctg agc att ctg     576
Gln Gln Ser Asn Pro Ser Phe Glu Gly Phe Gly Thr Leu Ser Ile Leu
            180                 185                 190 aaa gtg gcg ccg gaa ttt ctg ctg acc ttt agc gat gtg acc agc aac     624
Lys Val Ala Pro Glu Phe Leu Leu Thr Phe Ser Asp Val Thr Ser Asn
        195                 200                 205 cag agc agc gcg gtg ctg ggc aaa agc att ttt tgc atg gat ccg gtg     672
Gln Ser Ser Ala Val Leu Gly Lys Ser Ile Phe Cys Met Asp Pro Val
210                 215                 220
```

```
att gcg ctg atg cat gaa ctg acc cat agc ctg cat cag ctg tat ggc      720
Ile Ala Leu Met His Glu Leu Thr His Ser Leu His Gln Leu Tyr Gly
225                 230                 235                 240 att aac att ccg agc gat aaa cgt att cgt ccg cag gtg agc gaa ggc      768
Ile Asn Ile Pro Ser Asp Lys Arg Ile Arg Pro Gln Val Ser Glu Gly
                245                 250                 255 ttt ttt agc cag gat ggc ccg aac gtg cag ttt gaa gaa ctg tat acc      816
Phe Phe Ser Gln Asp Gly Pro Asn Val Gln Phe Glu Glu Leu Tyr Thr
            260                 265                 270 ttt ggc ggc ctg gat gtg gaa att att ccg cag att gaa cgt agc cag      864
Phe Gly Gly Leu Asp Val Glu Ile Ile Pro Gln Ile Glu Arg Ser Gln
        275                 280                 285 ctg cgt gaa aaa gcg ctg ggc cac tat aaa gat att gcg aaa cgc ctg      912
Leu Arg Glu Lys Ala Leu Gly His Tyr Lys Asp Ile Ala Lys Arg Leu
    290                 295                 300 aac aac atc aac aaa acc att ccg agc agc tgg att agc aac atc gat      960
Asn Asn Ile Asn Lys Thr Ile Pro Ser Ser Trp Ile Ser Asn Ile Asp
305                 310                 315                 320 aaa tac aaa aaa atc ttc agc gaa aaa tat aac ttc gat aaa gat aac     1008
Lys Tyr Lys Lys Ile Phe Ser Glu Lys Tyr Asn Phe Asp Lys Asp Asn
                325                 330                 335 acc ggc aac ttc gtg gtg aac att gat aaa ttc aac agc ctg tat agc     1056
Thr Gly Asn Phe Val Val Asn Ile Asp Lys Phe Asn Ser Leu Tyr Ser
            340                 345                 350 gat ctg acc aac gtg atg agc gaa gtg gtg tat agc agc cag tat aac     1104
Asp Leu Thr Asn Val Met Ser Glu Val Val Tyr Ser Ser Gln Tyr Asn
        355                 360                 365 gtg aaa aac cgc acc cat tat ttc agc cgt cat tat ctg ccg gtg ttt     1152
Val Lys Asn Arg Thr His Tyr Phe Ser Arg His Tyr Leu Pro Val Phe
    370                 375                 380 gcg aat att ctg gat gat aac atc tat acc atc cgt gat ggc ttt aac     1200
Ala Asn Ile Leu Asp Asp Asn Ile Tyr Thr Ile Arg Asp Gly Phe Asn
385                 390                 395                 400 ctg acc aac aaa ggc ttt aac att gaa aac agc ggc cag aac att gaa     1248
Leu Thr Asn Lys Gly Phe Asn Ile Glu Asn Ser Gly Gln Asn Ile Glu
                405                 410                 415 cgt aat ccg gcg ctg cag aaa ctg tct agc gaa agc gtg gtg gac ctg     1296
Arg Asn Pro Ala Leu Gln Lys Leu Ser Ser Glu Ser Val Val Asp Leu
            420                 425                 430 ttt acc aaa gtg tgc ctg cgt ctg acc ctg gtg cca cgc ggt agc acc     1344
Phe Thr Lys Val Cys Leu Arg Leu Thr Leu Val Pro Arg Gly Ser Thr
        435                 440                 445 tgc atc aaa gtg aaa aac aac cgt ctg ccg tat gtg gcg gat aaa gat     1392
Cys Ile Lys Val Lys Asn Asn Arg Leu Pro Tyr Val Ala Asp Lys Asp
    450                 455                 460 agc att agc cag gaa atc ttc gaa aac aaa atc atc acc gat gaa acc     1440
Ser Ile Ser Gln Glu Ile Phe Glu Asn Lys Ile Ile Thr Asp Glu Thr
465                 470                 475                 480 aac gtg cag aac tac agc gat aaa ttc agc ctg gat gaa agc att ctg     1488
Asn Val Gln Asn Tyr Ser Asp Lys Phe Ser Leu Asp Glu Ser Ile Leu
                485                 490                 495 gat ggc cag gtg ccg att aat ccg gaa att gtg gat ccg ctg ctg ccg     1536
Asp Gly Gln Val Pro Ile Asn Pro Glu Ile Val Asp Pro Leu Leu Pro
            500                 505                 510 aac gtg aac atg gaa ccg ctg aac ctg ccg ggc gaa gaa att gtg ttc     1584
Asn Val Asn Met Glu Pro Leu Asn Leu Pro Gly Glu Glu Ile Val Phe
        515                 520                 525 tat gat gat att acc aaa tat gtg gat tat ctg aac agc tac tac tat     1632
Tyr Asp Asp Ile Thr Lys Tyr Val Asp Tyr Leu Asn Ser Tyr Tyr Tyr
    530                 535                 540
```

-continued

| | |
|---|---|
| ctg gaa agc cag aaa ctg agc aac aac gtg gaa aac att acc ctg acc<br>Leu Glu Ser Gln Lys Leu Ser Asn Asn Val Glu Asn Ile Thr Leu Thr<br>545             550             555             560 | 1680 |
| acc tct gtg gaa gaa gcg ctg ggt tat agc aac aaa atc tac acc ttt<br>Thr Ser Val Glu Glu Ala Leu Gly Tyr Ser Asn Lys Ile Tyr Thr Phe<br>             565             570             575 | 1728 |
| ctg ccg agc ctg gcc gaa aaa gtg aac aaa ggc gtg cag gcg ggc ctg<br>Leu Pro Ser Leu Ala Glu Lys Val Asn Lys Gly Val Gln Ala Gly Leu<br>580             585             590 | 1776 |
| ttt ctg aac tgg gcg aac gaa gtg gtg gaa gat ttt acc acc aat atc<br>Phe Leu Asn Trp Ala Asn Glu Val Val Glu Asp Phe Thr Thr Asn Ile<br>        595             600             605 | 1824 |
| atg aaa aaa gat acc ctg gat aaa atc agc gat gtg agc gtg att att<br>Met Lys Lys Asp Thr Leu Asp Lys Ile Ser Asp Val Ser Val Ile Ile<br>610             615             620 | 1872 |
| ccg tat att ggt ccg gcg ctg aac att ggc aac agc gcc ctg cgt ggc<br>Pro Tyr Ile Gly Pro Ala Leu Asn Ile Gly Asn Ser Ala Leu Arg Gly<br>625             630             635             640 | 1920 |
| aac ttt aac cag gcg ttt gcg acc gcg ggt gtg gcg ttt ctg ctg gaa<br>Asn Phe Asn Gln Ala Phe Ala Thr Ala Gly Val Ala Phe Leu Leu Glu<br>             645             650             655 | 1968 |
| ggc ttt ccg gaa ttc acc att ccg gcg ctg ggc gtg ttt acc ttt tat<br>Gly Phe Pro Glu Phe Thr Ile Pro Ala Leu Gly Val Phe Thr Phe Tyr<br>        660             665             670 | 2016 |
| agc agc att cag gaa cgc gaa aaa atc atc aaa acc atc gaa aac tgc<br>Ser Ser Ile Gln Glu Arg Glu Lys Ile Ile Lys Thr Ile Glu Asn Cys<br>675             680             685 | 2064 |
| ctg gaa cag cgt gtg aaa cgt tgg aaa gat agc tat cag tgg atg gtg<br>Leu Glu Gln Arg Val Lys Arg Trp Lys Asp Ser Tyr Gln Trp Met Val<br>690             695             700 | 2112 |
| agc aac tgg ctg tct cgt att acc acc cag ttt aac cac atc aac tat<br>Ser Asn Trp Leu Ser Arg Ile Thr Thr Gln Phe Asn His Ile Asn Tyr<br>705             710             715             720 | 2160 |
| cag atg tat gac agc ctg agc tat cag gcg gat gcg att aaa gcg aaa<br>Gln Met Tyr Asp Ser Leu Ser Tyr Gln Ala Asp Ala Ile Lys Ala Lys<br>             725             730             735 | 2208 |
| atc gat ctg gaa tac aaa aaa tac agc ggc agc gat aaa gaa aac atc<br>Ile Asp Leu Glu Tyr Lys Lys Tyr Ser Gly Ser Asp Lys Glu Asn Ile<br>        740             745             750 | 2256 |
| aaa agc cag gtg gaa aac ctg aaa aac agc ctg gat gtg aaa att agc<br>Lys Ser Gln Val Glu Asn Leu Lys Asn Ser Leu Asp Val Lys Ile Ser<br>755             760             765 | 2304 |
| gaa gcc atg aat aac atc aac aaa ttc atc cgt gaa tgc agc gtg acc<br>Glu Ala Met Asn Asn Ile Asn Lys Phe Ile Arg Glu Cys Ser Val Thr<br>770             775             780 | 2352 |
| tac ctg ttt aaa aac atg ctg ccg aaa gtg att gat gaa ctg aac aaa<br>Tyr Leu Phe Lys Asn Met Leu Pro Lys Val Ile Asp Glu Leu Asn Lys<br>785             790             795             800 | 2400 |
| ttt gat ctg cgc acc aaa acc gaa ctg att aac ctg atc gat agc cat<br>Phe Asp Leu Arg Thr Lys Thr Glu Leu Ile Asn Leu Ile Asp Ser His<br>             805             810             815 | 2448 |
| aac att att ctg gtg ggc gaa gtg gat cgt ctg aaa gcg aaa gtg aac<br>Asn Ile Ile Leu Val Gly Glu Val Asp Arg Leu Lys Ala Lys Val Asn<br>        820             825             830 | 2496 |
| gaa agc ttc gaa aac acc atg ccg ttt aac atc ttc agc tac acc aac<br>Glu Ser Phe Glu Asn Thr Met Pro Phe Asn Ile Phe Ser Tyr Thr Asn<br>835             840             845 | 2544 |
| aac agc ctg ctg aaa gat att atc aac gaa tat ttt aac agc atc aac<br>Asn Ser Leu Leu Lys Asp Ile Ile Asn Glu Tyr Phe Asn Ser Ile Asn | 2592 |

```
                   850                 855                 860
gat agc aaa att ctg agc ctg cag aac aaa aaa aac gcg ctg gtt gat       2640
Asp Ser Lys Ile Leu Ser Leu Gln Asn Lys Lys Asn Ala Leu Val Asp
865                 870                 875                 880 acc agc ggc tat aac gcg gaa gtg cgt gtg ggc gat aac gtg cag ctg       2688
Thr Ser Gly Tyr Asn Ala Glu Val Arg Val Gly Asp Asn Val Gln Leu
                885                 890                 895 aac acc att tat acc aac gat ttc aaa ctg agc agc agc ggc gat aaa       2736
Asn Thr Ile Tyr Thr Asn Asp Phe Lys Leu Ser Ser Ser Gly Asp Lys
            900                 905                 910 att att gtg aac ctg aat aac aac att ctg tac agc gcg att tat gaa       2784
Ile Ile Val Asn Leu Asn Asn Asn Ile Leu Tyr Ser Ala Ile Tyr Glu
        915                 920                 925 aac agc agc gtg agc ttt tgg atc aaa atc agc aaa gat ctg acc aac       2832
Asn Ser Ser Val Ser Phe Trp Ile Lys Ile Ser Lys Asp Leu Thr Asn
    930                 935                 940 agc cat aac gaa tac acc atc atc aac agc att gaa cag aac agc ggc       2880
Ser His Asn Glu Tyr Thr Ile Ile Asn Ser Ile Glu Gln Asn Ser Gly
945                 950                 955                 960 tgg aaa ctg tgc att cgt aac ggc aac att gaa tgg att ctg cag gat       2928
Trp Lys Leu Cys Ile Arg Asn Gly Asn Ile Glu Trp Ile Leu Gln Asp
                965                 970                 975 gtg aac cgc aaa tat aaa agc ctg atc ttc gat tat agc gaa agc ctg       2976
Val Asn Arg Lys Tyr Lys Ser Leu Ile Phe Asp Tyr Ser Glu Ser Leu
            980                 985                 990 agc cat acc ggc tat acc aac aaa tgg ttc ttt gtg acc atc acc aac       3024
Ser His Thr Gly Tyr Thr Asn Lys Trp Phe Phe Val Thr Ile Thr Asn
        995                 1000                1005 aac att atg ggc tat atg aaa ctg tat atc aac ggc gaa ctg aaa           3069
Asn Ile Met Gly Tyr Met Lys Leu Tyr Ile Asn Gly Glu Leu Lys
    1010                1015                1020 cag agc cag aaa atc gaa gat ctg gat gaa gtg aaa ctg gat aaa           3114
Gln Ser Gln Lys Ile Glu Asp Leu Asp Glu Val Lys Leu Asp Lys
1025                1030                1035 acc atc gtg ttt ggc atc gat gaa aac att gat gaa aac cag atg           3159
Thr Ile Val Phe Gly Ile Asp Glu Asn Ile Asp Glu Asn Gln Met
        1040                1045                1050 ctg tgg att cgc gat ttt aac atc ttt agc aaa gaa ctg agc aac           3204
Leu Trp Ile Arg Asp Phe Asn Ile Phe Ser Lys Glu Leu Ser Asn
    1055                1060                1065 gaa gat att aac atc gtg tac gaa ggc cag att gat atc ggt ggt           3249
Glu Asp Ile Asn Ile Val Tyr Glu Gly Gln Ile Asp Ile Gly Gly
1070                1075                1080 ggt ggt agc ggt ggt ggc ggt tca ggt ggt ggt ggc agc gtt acc           3294
Gly Gly Ser Gly Gly Gly Gly Ser Gly Gly Gly Gly Ser Val Thr
        1085                1090                1095 cat cgt ctg gct ggt ctg ctg tct cgt agc ggt ggt gtt gtg aaa           3339
His Arg Leu Ala Gly Leu Leu Ser Arg Ser Gly Gly Val Val Lys
    1100                1105                1110 aac aat ttt gtg ccg aca aat gtt ggt agc aaa gca ttt taactcgag         3387
Asn Asn Phe Val Pro Thr Asn Val Gly Ser Lys Ala Phe
1115                1120                1125

<210> SEQ ID NO 18
<211> LENGTH: 1126
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 18

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415
```

```
Arg Asn Pro Ala Leu Gln Lys Leu Ser Ser Glu Ser Val Val Asp Leu
            420                 425                 430

Phe Thr Lys Val Cys Leu Arg Leu Thr Leu Val Pro Arg Gly Ser Thr
            435                 440                 445

Cys Ile Lys Val Lys Asn Asn Arg Leu Pro Tyr Val Ala Asp Lys Asp
450                 455                 460

Ser Ile Ser Gln Glu Ile Phe Glu Asn Lys Ile Ile Thr Asp Glu Thr
465                 470                 475                 480

Asn Val Gln Asn Tyr Ser Asp Lys Phe Ser Leu Asp Glu Ser Ile Leu
                485                 490                 495

Asp Gly Gln Val Pro Ile Asn Pro Glu Ile Val Asp Pro Leu Leu Pro
            500                 505                 510

Asn Val Asn Met Glu Pro Leu Asn Leu Pro Gly Glu Glu Ile Val Phe
            515                 520                 525

Tyr Asp Asp Ile Thr Lys Tyr Val Asp Tyr Leu Asn Ser Tyr Tyr Tyr
530                 535                 540

Leu Glu Ser Gln Lys Leu Ser Asn Asn Val Glu Asn Ile Thr Leu Thr
545                 550                 555                 560

Thr Ser Val Glu Glu Ala Leu Gly Tyr Ser Asn Lys Ile Tyr Thr Phe
                565                 570                 575

Leu Pro Ser Leu Ala Glu Lys Val Asn Lys Gly Val Gln Ala Gly Leu
            580                 585                 590

Phe Leu Asn Trp Ala Asn Glu Val Val Glu Asp Phe Thr Thr Asn Ile
            595                 600                 605

Met Lys Lys Asp Thr Leu Asp Lys Ile Ser Asp Val Ser Val Ile Ile
610                 615                 620

Pro Tyr Ile Gly Pro Ala Leu Asn Ile Gly Asn Ser Ala Leu Arg Gly
625                 630                 635                 640

Asn Phe Asn Gln Ala Phe Ala Thr Ala Gly Val Ala Phe Leu Leu Glu
                645                 650                 655

Gly Phe Pro Glu Phe Thr Ile Pro Ala Leu Gly Val Phe Thr Phe Tyr
            660                 665                 670

Ser Ser Ile Gln Glu Arg Glu Lys Ile Ile Lys Thr Ile Glu Asn Cys
            675                 680                 685

Leu Glu Gln Arg Val Lys Arg Trp Lys Asp Ser Tyr Gln Trp Met Val
690                 695                 700

Ser Asn Trp Leu Ser Arg Ile Thr Thr Gln Phe Asn His Ile Asn Tyr
705                 710                 715                 720

Gln Met Tyr Asp Ser Leu Ser Tyr Gln Ala Asp Ala Ile Lys Ala Lys
                725                 730                 735

Ile Asp Leu Glu Tyr Lys Lys Tyr Ser Gly Ser Asp Lys Glu Asn Ile
            740                 745                 750

Lys Ser Gln Val Glu Asn Leu Lys Asn Ser Leu Asp Val Lys Ile Ser
            755                 760                 765

Glu Ala Met Asn Asn Ile Asn Lys Phe Ile Arg Glu Cys Ser Val Thr
770                 775                 780

Tyr Leu Phe Lys Asn Met Leu Pro Lys Val Ile Asp Glu Leu Asn Lys
785                 790                 795                 800

Phe Asp Leu Arg Thr Lys Thr Glu Leu Ile Asn Leu Ile Asp Ser His
                805                 810                 815

Asn Ile Ile Leu Val Gly Glu Val Asp Arg Leu Lys Ala Lys Val Asn
            820                 825                 830
```

-continued

```
Glu Ser Phe Glu Asn Thr Met Pro Phe Asn Ile Phe Ser Tyr Thr Asn
            835                 840                 845

Asn Ser Leu Leu Lys Asp Ile Ile Asn Glu Tyr Phe Asn Ser Ile Asn
    850                 855                 860

Asp Ser Lys Ile Leu Ser Leu Gln Asn Lys Lys Asn Ala Leu Val Asp
865                 870                 875                 880

Thr Ser Gly Tyr Asn Ala Glu Val Arg Val Gly Asp Asn Val Gln Leu
                885                 890                 895

Asn Thr Ile Tyr Thr Asn Asp Phe Lys Leu Ser Ser Gly Asp Lys
            900                 905                 910

Ile Ile Val Asn Leu Asn Asn Ile Leu Tyr Ser Ala Ile Tyr Glu
            915                 920                 925

Asn Ser Ser Val Ser Phe Trp Ile Lys Ile Ser Lys Asp Leu Thr Asn
    930                 935                 940

Ser His Asn Glu Tyr Thr Ile Ile Asn Ser Ile Glu Gln Asn Ser Gly
945                 950                 955                 960

Trp Lys Leu Cys Ile Arg Asn Gly Asn Ile Glu Trp Ile Leu Gln Asp
                965                 970                 975

Val Asn Arg Lys Tyr Lys Ser Leu Ile Phe Asp Tyr Ser Glu Ser Leu
            980                 985                 990

Ser His Thr Gly Tyr Thr Asn Lys Trp Phe Phe Val Thr Ile Thr Asn
        995                 1000                 1005

Asn Ile Met Gly Tyr Met Lys Leu Tyr Ile Asn Gly Glu Leu Lys
        1010                 1015                 1020

Gln Ser Gln Lys Ile Glu Asp Leu Asp Glu Val Lys Leu Asp Lys
        1025                 1030                 1035

Thr Ile Val Phe Gly Ile Asp Glu Asn Ile Asp Glu Asn Gln Met
        1040                 1045                 1050

Leu Trp Ile Arg Asp Phe Asn Ile Phe Ser Lys Glu Leu Ser Asn
        1055                 1060                 1065

Glu Asp Ile Asn Ile Val Tyr Glu Gly Gln Ile Asp Ile Gly Gly
        1070                 1075                 1080

Gly Gly Ser Gly Gly Gly Ser Gly Gly Gly Ser Val Thr
        1085                 1090                 1095

His Arg Leu Ala Gly Leu Leu Ser Arg Ser Gly Gly Val Val Lys
        1100                 1105                 1110

Asn Asn Phe Val Pro Thr Asn Val Gly Ser Lys Ala Phe
        1115                 1120                 1125

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

His His His His His His
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Gly Gly Gly Gly Ser
1               5

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser Gly Gly Gly Gly Ser Gly Gly Gly Gly Ser
1               5                   10                  15
```